US008092780B2

(12) United States Patent
Livingston et al.

(10) Patent No.: US 8,092,780 B2
(45) Date of Patent: *Jan. 10, 2012

(54) POLYVALENT CONJUGATE VACCINE FOR CANCER

(75) Inventors: Philip O. Livingston, New York, NY (US); Govindaswami Ragupathi, New York, NY (US); Samuel J. Danishefsky, Englewood, NJ (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 285 days.

This patent is subject to a terminal disclaimer.

(21) Appl. No.: 12/262,729

(22) Filed: Oct. 31, 2008

(65) Prior Publication Data

US 2009/0060938 A1 Mar. 5, 2009

Related U.S. Application Data

(63) Continuation of application No. 10/752,945, filed on Jan. 6, 2004, now Pat. No. 7,479,266, which is a continuation-in-part of application No. PCT/US02/21348, filed on Jul. 5, 2002.

(60) Provisional application No. 60/303,494, filed on Jul. 6, 2001, provisional application No. 60/347,231, filed on Jan. 10, 2002.

(51) Int. Cl.
| | |
|---|---|
| *A61P 35/00* | (2006.01) |
| *A61K 31/70* | (2006.01) |
| *A61K 31/715* | (2006.01) |
| *A61K 38/14* | (2006.01) |
| *A61K 39/00* | (2006.01) |
| *A61K 47/00* | (2006.01) |
| *A61K 39/385* | (2006.01) |
| *A61K 39/39* | (2006.01) |

(52) U.S. Cl. ...................... 424/1.57; 424/1.69; 424/1.73; 424/193.1; 424/277.1; 514/19.3; 514/20.9; 514/25; 514/54

(58) Field of Classification Search .......................... None
See application file for complete search history.

(56) References Cited

U.S. PATENT DOCUMENTS

| 5,371,197 | A | * | 12/1994 | Marburg et al. ............... 530/404 |
| 6,660,714 | B1 | * | 12/2003 | Danishefsky et al. ............ 514/2 |
| 2003/0108574 | A1 | | 6/2003 | Jennings et al. |
| 2004/0151733 | A1 | | 8/2004 | Livingston et al. |
| 2004/0180002 | A1 | | 9/2004 | Young et al. |

FOREIGN PATENT DOCUMENTS

| WO | WO 01/47552 | 7/2001 |
| WO | WO 03/003985 A2 | 1/2003 |
| WO | WO 2004/091507 | 10/2004 |

OTHER PUBLICATIONS

Stedman's Medical dictionary, 2000.*
Abstract of Wheeler (Salud p'ublica de M'exico, (Jul.-Aug. 1997) 39 (4) 283-7).*
Efferson et al. (Anticancer Research, 2005, vol. 25, pp. 715-724).*
Bachman et al. (Journal of Immunology, 2005, vol. 175, pp. 4677-4685).*
Sabbatini et al. (International Journal of Cancer, 2000, vol. 87, pp. 79-85).*
Gilewski et al. (PNAS, Mar. 2001, vol. 98, pp. 3270-3275).*
Musselli et al. (Journal of Cancer Research and Clinical Oncology, 2001, vol. 127, suppl. 2, pp. R20-R26).*
Allen et al. (Chem. Eur. J., 2000, vol. 6, pp. 1366-1375).*
Chapman et al. (Clinical Cancer Research, Dec. 2000, vol. 6, pp. 4658-4662).*
Abstract of Chapman et al. (Proc Am Assoc Cancer Res, 1998, vol. 39, p. 369).*
Livingston (Seminars in Oncology, 1998, vol. 25, pp. 636-645).*
Livingston et al. (Journal of Clinical Oncology, 2000, vol. 20, pp. 85-93).*
Toyokuni et al (Chemical Society Reviews, 1995, vol. 24, pp. 231-242).*
Adluri et al., "Immunogenicity of synthetic TF-KLH (keyhole limpet hemocyanin) and sTn-KLH conjugates in colorectal carcinoma patients," *Cancer Immunol. Immunother.* 41(3):185-192 (1995).
Allen et al., "Pursuit of Optimal Carbohydrate-Based Anticancer Vaccines: Preparation of a Multiantigenic Unimolecular Glycopeptide Containing the Tn, MBr1, and Lewis$^y$ Antigens," *J. Am. Chem. Soc.* 123(9):1890-1897 (2001).
Bennett et al., "Cloning of a human UDP-N-acetyl-alpha-D-Galactosamine:polypeptide N-acetylgalactosaminyltransferase that complements other GalNAc-transferases in complete O-glycosylation of the MUC1 tandem repeat," *J. Biol. Chem.* 273(46):30472-30481 (1998).
Boon, "Toward a genetic analysis of tumor rejection antigens," *Adv. Cancer Res.* 58:177-210 (1992).
Brezicka et al., "Immunohistological detection of fucosyl-GM1 ganglioside in human lung cancer and normal tissues with monoclonal antibodies," *Cancer Res.* 49(5):1300-1305 (1989).
Buskens et al., 2003, "Adenocarcinomas of the Gastro-Esophageal Junction: A Comparative Study of the Gastric Cardia and the Esophagus with Respect to Cyclooxygenase-2 Expresion," Digestive Disease Week Abstracts and Itinerary Planner, abstract No. 850.

(Continued)

*Primary Examiner* — Karen Canella
(74) *Attorney, Agent, or Firm* — Law Offices of Albert Wai-Kit Chan, PLLC

(57) ABSTRACT

This invention provides a polyvalent vaccine comprising at least two conjugated antigens selected from a group containing glycolipid antigen, polysaccharide antigen, mucin antigen, glycosylated mucin antigen and an appropriate adjuvant. This invention also provides a multivalent vaccine comprising at least two of the following: glycosylated MUC-1-32mer, Globo H, GM2, Le$^y$, Tn(c), sTN(c), and TF(c). This invention provides the vaccine above, wherein the adjuvant is saponin-based adjuvant. This invention provides a method for inducing immune response in a subject comprising administering an effective amount of the vaccine above to the subject. Finally, this invention provides a method for treating cancer in a subject comprising administering an appropriate amount of the vaccine above to the subject.

21 Claims, No Drawings

OTHER PUBLICATIONS

Caragine et al., "A tumor-expressed inhibitor of the early but not late complement lytic pathway enhances tumor growth in a rat model of human breast cancer," *Cancer Res.* 62(4):1110-1115 (2002).

Carter et al., 1981, Chemotherapy of Cancer—Second Edition, appendix C.

Cruse et al., 1995, Illustrated Dictionary of Immunology, CRC Press, p. 241.

Dickler et al., "Immunogenicity of a fucosyl-GM1-keyhole limpet hemocyanin conjugate vaccine in patients with small cell lung cancer," *Clin. Cancer Res.* 5(10):2773-2779 (1999).

Drexler et al., "Recent results on the biology of Hodgkin and Reed-Sternberg cells. II. Continuous cell lines," *Leuk. Lymphoma* 9(1-2):1-25 (1993).

Eggermont et al., "EORTC 18961: Post-operative adjuvant ganglioside GM2-KLH21 vaccination treatment vs observation in stage II (T3-T4N0M0) melanoma: 2nd interim analysis led to an early disclosure of the results," *J. Clin.Oncol.* 26(15S) (May 20 Supplement), (Abstract) (2008).

Embleton et al., "Monoclonal Antibodies and Cancer," *Immunol. Ser.* 23:181-207 (1984).

Ezzell, "Cancer 'vaccines;' An idea whose time has come?," *J. NIH Res.* 7:46-949 (1995).

Fishelson et al., "Obstacles to cancer immunotherapy: expression of membrane complement regulatory proteins (mCRPs) in tumors," *Mol. Immunol.* 40(2-4):109-123 (2003).

Fung et al., "Active specific immunotherapy of a murine mammary adenocarcinoma using a synthetic tumor-associated glycoconjugate," *Cancer Res.* 50(14):4308-4314 (1990).

Gatza and Okada, "Tumor cell lysate-pulsed dendritic cells are more effective than TCR Id protein vaccines for active immunotherapy of T cell lymphoma," *J. Immunol.* 169(9):5227-5235 (2002).

Gelboin, "Cytochrome P450 and Monoclonal Antibodies," *Pharmacol. Rev.* 45(4):413-453 (1993).

Giaccone et al., "Phase III Study of Adjuvant Vaccination With Bec2/Bacille Calmette-Guerin in Responding Patients With Limited-Disease Small-Cell Lung Cancer (European Organisation for Research and Treatment of Cancer 08971-08971B; Silva Study)," *J. Clin. Oncol.* 23(28):6854-6864 (2005).

Gura, "Systems for Identifying New Drugs Are Often Faulty," *Science* 278(5340):1041-1042 (1997).

Helling et al., "$G_{D3}$ Vaccines for Melanoma: Superior Immunogenicity of Keyhole Limpet Hemocyanin Conjugate Vaccines," *Cancer Res.* 54(1):197-203.

Ho et al., "Heterogeneity of Mucin Gene Expression in Normal and Neoplastic Tissues," *Cancer Res.* 53(3):641-651 (1993).

Hsueh et al., "Active Specific Immunotherapy with Polyvalent Melanoma Cell Vaccine for Patients with In-Transit Melanoma Metastases," *Cancer* 85(10):2160-2169 (1999).

Jennemann et al., "Effects of Monophosphoryllipid-A on the Immunization of Mice with Keyhole Limpet Hemocyanin- and Muramylidipeptide-Ganglioside Gfpt1 Conjugates," *J. Biochem.* 119(2):378-384 (1996).

Jennemann et al., "Specific Immunization Using Keyhole Limpet Hemocyanin-Ganglioside Conjugates," *J. Biochem.* 115(6):1047-1052 (1994).

Jennings et al., "Induction of Meningococcal Group B Polysaccharide-Specific IgG Antibodies in Mice by Using an N-Propionylated B Polysaccharide-Tetanus Toxoid Conjugate Vaccine," *J. Immunol.* 137(5):1708-1713 (1986).

Jiang et al., "Vaccination with a mixed vaccine of autogenous and allogeneic breast cancer cells and tumor associated antigens CA15-3, CEA and CA125—results in immune and clinical responses in breast cancer patients," *Cancer Biother. Radiopharm.* 15(5):495-505 (2000).

Kaiser, "Cancer. First pass at cancer genome reveals complex landscape," *Science* 313:1370 (2006).

Keder and Klein, "Cancer immunotherapy: are the results discouraging? Can they be improved?" *Adv. Cancer Res.* 59:245-322 (1992).

Keding and Danishefsky, "Prospects for total synthesis: a vision for a totally synthetic vaccine targeting epithelial tumors," *Proc. Natl. Acad. Sci. U. S. A.* 101(33):11937-11942 (2004).

Kim et al., "Effect of immunological adjuvant combinations on the antibody and T-cell response to vaccination with MUC1-KLH and GD3-KLH conjugates," *Vaccine* 19(4-5):530-537 (2000).

Kirkwood et al., "High-Dose Interferon Alfa-2b Significantly Prolongs Relapse-Free and Overall Survival Compared With the GM2-KLH/QS-21 Vaccine in Patients With Resected Stage IIB-III Melanoma: Results of Intergroup Trial E1694/S9512/C509801," *J. Clin. Oncol.* 19(9):2370-2380 (2001).

Krontiris et al., 1994, "Molecular and Cellular Biology of Cancer," Internal Medicine, chapters 71-72, pp. 699-729.

Krug et al., "0-154 Development of a tetravalent small cell lung cancer (SCLC) vaccine containing GM2, fucosyl GM1, Globo H, and polysialic acid," *Lung Cancer* 41:S47 (2003). (abstract only).

Krug et al., "Vaccination of patients with small-cell lung cancer with synthetic fucosyl GM-1 conjugated to keyhole limpet hemocyanin," *Clin. Cancer Res.* 10(18 Pt 1):6094-6100 (2004).

Krug et al., "Vaccination of small cell lung cancer patients with polysialic acid or N-propionylated polysialic acid conjugated to keyhole limpet hemocyanin," *Clin.Cancer Res.* 10(3):916-923 (2004).

Krug, "Vaccine therapy for small cell lung cancer," *Semin. Oncol.* 31(1 Suppl. 1):112-116 (2004).

Kudryashov et al., "Immunogenicity of synthetic conjugates of Lewis$^\beta$ oligosaccharide with proteins in mice: towards the design of anticancer vaccines," *Cancer Immunol. Immunother.* 45(6):281-286 (1998).

Kudryashov et al., "Toward optimized carbohydrate-based anticancer vaccines: epitope clustering, carrier structure, and adjuvant all influence antibody responses to Lewis(y) conjugates in mice," Proc. Natl. Acad. Sci. U. S. A. 98(6):3264-3269 (2001).

Lida et al., "Interaction of human macrophage C-type lectin with O-linked N-acetylgalactosamine residues on mucin glycopeptides," *J. Biol. Chem.* 274(16):10697-10705 (1999).

Livingston et al., "Antigen expression on small cell lung cancer (SCLC) cell lines confirms selection of a tetravalent vaccine against SCLC containing GM2, fucosyl DM1, globo H and polysialic acid," Proceedings of the Annual Meeting of the American Association for Cancer Research, New York, NY. 44:945 (2003).

Livingston et al., "Augmenting the immunogenicity of carbohydrate tumor antigens," *Semin. Cancer Biol.* 6(6):357-366 (1995).

Livingston et al., "Carbohydrate vaccines that induce antibodies against cancer. 1. Rationale," *Cancer Immunol. Immunother.* 45(1):1-9 (1997).

Livingston et al., "Current Status of Cancer Vaccines Against Cell Surface Antigens on Small Cell Lung Cancer," *Biotecnologia Aplicada* 19(3y4):192 (2002).

Livingston et al., "Immunization of Mice with Polysialic Acid and N-Propionylated Polysialic Acid-KLH Conjugates Plus QS-21 Results in Antibodies against Human Small Cell Lung Cancer Cells," Proceedings of the American Association for Cancer Research 92nd Annual Meeting, 42:288 (2001).

Livingston et al., "Improved Survival in Stage III Melanoma Patients With GM2 Antibodies: A Randomized Trial of Adjuvant Vaccination With GM2 Ganglioside," *J. Clin. Oncol.* 12(5):1036-1044 (1994).

Livingston et al., "Phase 1 trial of immunological adjuvant QS-21 with a GM2 ganglioside-keyhole limpet haemocyanin conjugate vaccine in patients with malignant melanoma," *Vaccine* 12(14):1275-80 (1998). (Abstract Only).

Livingston et al., "Selection of GM2, fucosyl GM1, globo H and polysialic acid as targets on small cell lung cancers for antibody mediated immunotherapy," *Cancer Immunol. Immunother.* 54(10):1018-1025 (2005).

Livingston et al., "Vaccines containing purified GM2 ganglioside elicit GM2 antibodies in melanoma patients," *Proc. Natl. Acad. Sci. U. S. A.* 84(9):2911-2915 (1987).

Livingston et al., Proceedings of the American Assoc for Cancer Research and Annual Meeting of the American Association for Cancer Research Meeting 44 abstract 4754 (2003).

MaClean et al., "Immunization of breast cancer patients using a synthetic sialyl-Tn glycoconjugate plus Detox adjuvant," *Cancer Immunol. Immunother.* 36(4):215-222 (1993).

Morton et al., "An international, randomized, phase III trial of bacillus Calmette-Guerin (BCG) plus allogeneic melanoma vaccine (MCV) or placebo after complete resection of melanoma metastatic to regional or distant sites," *J. Clin. Oncol.* 25(18S) (Jun. 20 Supplement), (Abstract) (2007).

Müller et al., "Localization of O-glycosylation sites on glycopeptide fragments from lactation-associated MUC1. All putative sites within the tandem repeat are glycosylation targets in vivo," *J. Biol. Chem.* 272(40):24780-24793 (1997).

Neeson and Paterson, "Effects of the tumor microenvironment on the efficacy of tumor immunotherapy," *Immunol. Invest.* 35(3-4):359-394 (2006).

Orlandi et al., "Antibody and CD8+ T cell responses against HER2/neu required for tumor eradication after DNA immunization with a Flt-3 ligand fusion vaccine," *Clin. Cancer Res.* 13(20):6195-6203 (2007).

Patel et al., "Targeting lethal minimal residual disease in small cell lung cancer," *Semin. Oncol.* 30(1):79-85 (2003).

Pon et al., "*N*-Propionylated Group B Meningococcal Polysaccharide Mimics a Unique Bactericidal Capsular Epitope in Group B *Neisseria meningitides*," *J. Exp. Med.* 185(11):1929-1938 (1997).

Raez et al., "Lung Cancer Immunotherapy," *Clin. Med. Res.* 3(4):221-228, (2005).

Ragupathi et al., "A preclinical study comparing approaches for augmenting the immunogenicity of a heptavalent KLH-conjugate vaccine against epithelial cancers," *Cancer Immunol. Immunother.* 52(10):608-616 (2003).

Ragupathi et al., "Comparison of antibody titers after immunization with monovalent or tetravalent KLH conjugate vaccines," *Vaccine* 20(7-8):1030-1038, (2002).

Ragupathi et al., "Comparison of the antibody response to monovalent and polyvalent conjugate cancer vaccines," Proceedings of the American Association for Cancer Research Annual Meeting, 41:874-875 (2000).

Ragupathi et al., "Consistent Antibody Response against Ganglioside GD2 Induced in Patients with Melanoma by a GD2 Lactone-Keyhole Limpet Hemocyanin Conjugate Vaccine plus Immunological Adjuvant QS-21," *Clin.Cancer Res.* 9(14):5214-5220 (2003).

Ragupathi et al., "Induction of Antibodies Against GD3 Ganglioside in Melanoma Patients by Vaccinations with GD3-Lactone-KLH Conjugate plus Immunological Adjuvant QS-21," *Int. J. Cancer* 85(5):659-666 (2000).

Ragupathi et al., "On the power of chemical synthesis: immunological evaluation of models for multiantigenic carbohydrate-based cancer vaccines," *Proc. Natl. Acad. Sci. U. S. A.* 99(21):13699-13704 (2002).

Ragupathi et al., "The case for polyvalent cancer vaccines that induce antibodies," *Expert Rev. Vaccines* 1(2):193-206 (2002).

Ragupathi, "Carbohydrate Antigens as Targets for Active Specific Immunotherapy," *Cancer Immunol. Immunother.* 42(3):152-157 (1996).

Roitt et al., Immunology, Third Edition, 1993, p. 6.4-6.5.

SingHal et al., "Induction of α-N-Acetylgalactosamine-O-Serine/Threonine (Tn) Antigen-mediated Cellular Immune Response for Active Immunotherapy in Mice," *Cancer Res.* 51:1406-1411 (1991).

Slovin et al., "Carbohydrate vaccines in cancer: immunogenicity of a fully synthetic globo H hexasaccharide conjugate in man," *Proc. Natl. Acad. Sci. U. S. A.* 96(10):5710-5715 (1999).

Smith, "Cancer and the Immune System," *Pediatr. Clin. North Am.* 41(4):841-850 (1994).

Soares et al., "Three different vaccines based on the 140-amino acid MUC1 peptide with seven tandemly repeated tumor-specific epitopes elicit distinct immune effector mechanisms in wild-type versus MUC1-transgenic mice with different potential for tumor rejection," *J. Immunol.* 166(11):6555-6563 (2001).

Spitler, "Cancer Vaccines: The Interferon Analogy," *Cancer Biother.* 10(1):1-3 (1995).

Taber's Cyclopedic Medical Dictionary, 1985, p. 274.

White et al., "Antibody-targeted immunotherapy for treatment of malignancy," *Annu. Rev. Med.* 52:125-145 (2001).

Zellner et al., "Disparity in expression of protein kinase C alpha in human glioma versus glioma-derived primary cell lines: therapeutic implications," *Clin.Cancer Res.* 4(7):1797-1802 (1998).

Zhang et al., "Immune sera and monoclonal antibodies define two configurations for the sialyl Tn tumor antigen," *Cancer Res.* 55(15):3364-3368 (1995).

Zhang et al., "Selection of tumor antigens as targets for immune attack using immunohistochemistry: I. Focus on gangliosides," *Int. J. Cancer* 73(1):42-49.

Zhang et al., "Selection of Tumor Antigens as Targets for Immune Attack Using Immunohistochemistry: II. Blood Group-Related Antigens," *Int. J. Cancer* 73:50-56 (1997).

Zhang et al., "Selection of tumor antigens as targets for immune attack using immunohistochemistry: protein antigens," *Clin. Cancer Res.* 4(11):2669-2676 (1998).

Zhao and Cheung, "$G_{D2}$ Oligosaccharide: Target for Cytoxic T Lymphocytes," *J. Exp. Med.* 182(1):67-74 (1995).

Supplementary European Search Report, Nov. 6, 2008, for European Application No. EP 06 82 5619, for Sloan-Kettering Institute for Cancer Research.

PCT International Search Report, Sep. 5, 2007, Int'l Application No. PCT/US06/39312, for Sloan-Kettering Institute for Cancer Research.

PCT Written Opinion of the International Searching Authority, Sep. 5, 2007, Int'l Application No. PCT/US06/39312, for Sloan-Kettering Institute for Cancer Research.

EPO Summons to Attend Oral Proceedings, Jun. 24, 2009, European Application No. EP 02 75 2182.

EPO Examiner's Report, Jan. 3, 2008, European Application No. EP 02 75 2182.

EPO Examiner's Report, Nov. 6, 2007, European Application No. EP 04 759415.5.

EPO Summons to Attend Oral Proceedings, Mar. 26, 2009, European Application No. EP 04 759415.5.

EPO Examiner's Report, Jun. 3, 2009, for Livingston et al., European Application No. EP 06 82 5619.

U.S. Office Action, Jun. 14, 2006, for Livingston et al., U.S. Appl. No. 10/752,945, filed Jan. 6, 2004.

EPO Summons to Attend Oral Proceedings, Aug. 19, 2009, European Application No. EP 04 759415.5.

U.S. Office Action for Livingston et al., U.S. Appl. No. 10/752,945, filed Jan. 6, 2004, dated Jul. 5, 2007.

U.S. Office Action for Livingston et al., U.S. Appl. No. 10/752,945, filed Jan. 6, 2004, dated Oct. 18, 2006.

EPO Supplementary Search Report for Sloan-Kettering Institute for Cancer Research, Int'l Application No. PCT/US02/21348, Filed Jul. 5, 2002, Dated Apr. 6, 2006.

PCT International Search Report for Sloan-Kettering Institute for Cancer Research, Int'l Application No. PCT/US02/21348, Filed Jul. 5, 2002, Dated Jun. 5, 2003.

Supplementary Partial European Search Report for Sloan-Kettering Institute for Cancer Research for European Application No. EP 04 75 9415 dated Jul. 12, 2007.

U.S. Office Action for Livingston et al., U.S. Appl. No. 10/752,945, filed Jan. 6, 2004, dated Jan. 25, 2008.

Notice of Allowance for Livingston et al., U.S. Appl. No. 10/752,945, filed Jan. 6, 2004, dated Jul. 24, 2008.

EPO Examiner's Report for Livingston et al., European Application No. EP 04 759 415.5, Filed Nov. 4, 2005, dated Jul. 18, 2008.

PCT International Search Report, Nov. 4, 2005, Int'l Application No. PCT/US04/11122, for Sloan-Kettering Institute for Cancer Research.

PCT Written Opinion of the International Searching Authority, Nov. 4, 2005, Int'l Application No. PCT/US04/11122, for Sloan-Kettering Institute for Cancer Research.

Office Action for Livingston et al., U.S. Appl. No. 11/246,752, filed Oct. 7, 2005, dated May 28, 2009.

Office Action for Livingston et al., U.S. Appl. No. 11/246,752, filed Oct. 7, 2005, dated Dec. 22, 2008.

Office Action for Livingston et al., U.S. Appl. No. 11/246,752, filed Oct. 7, 2005, dated May 13, 2008.

Office Action for Livingston et al., U.S. Appl. No. 11/246,752, filed Oct. 7, 2005, dated Jan. 24, 2008.

Office Action for Livingston et al., U.S. Appl. No. 11/246,752, filed Oct. 7, 2005, dated Oct. 5, 2007.

Office Action for Livingston et al., U.S. Appl. No. 11/246,752, filed Oct. 7, 2005, dated Jan. 31, 2007.
Office Action for Livingston et al., U.S. Appl. No. 11/246,752, filed Oct. 7, 2005, dated Oct. 12, 2006.
Office Action for Livingston et al., U.S. Appl. No. 11/246,752, filed Oct. 7, 2005, dated Jul. 28, 2006.
Office Action for Livingston et al., U.S. Appl. No. 12/089,302, filed Apr. 4, 2008, dated Dec. 31, 2009.
Adluri et al., "Specificity analysis of sera from breast cancer patients vaccinated with MUC1-KLH plus QS-21," *Br. J. Cancer*. 79(11-12):1806-1812 (1999).
Gilewski et al., "Vaccination of high-risk breast cancer patients with mucin-1 (MUC1) keyhole limpet hemocyanin conjugate plus QS-21," *Clin. Cancer Res*. 6(5):1693-1701 (2000).
Sabbatini et al., "Pilot study of a heptavalent vaccine-keyhole limpet hemocyanin conjugate plus QS21 in patients with epithelial ovarian, fallopian tube, or peritoneal cancer," *Clin. Cancer Res*. 13(14):4170-4177 (2007).
Slovin et al., "A polyvalent vaccine for high-risk prostate patients: are more antigens better?" *Cancer Immunol. Immunother*. 56(12):1921-30 (2007).

* cited by examiner

POLYVALENT CONJUGATE VACCINE FOR CANCER

This application disclosed herein is a continuation of U.S. Ser. No. 10/752,945, filed Jan. 6, 2004 now U.S. Pat. No. 7,479,266, which is a continuation-in-part of International Application No. PCT/US02/21348, filed Jul. 5, 2002, which claims priority of U.S. Ser. 60/303,494, filed on Jul. 6, 2001 and U.S. Ser. No. 60/347,231, filed on Jan. 10, 2002, the contents of which are hereby incorporated by reference into this application.

Throughout this application, various references are referred to. Disclosures of these publications in their entireties are hereby incorporated by reference into this application to more fully describe the state of the art to which this invention pertains.

The invention disclosed herein was made with United States government support under NIH Grant Nos. CA33049 and CA52477 from the United States Department of Health and Human Services. Accordingly, the United States Government has certain rights in this invention.

BACKGROUND OF THE INVENTION

Tumor-specific antigens have been identified and pursued as targets for vaccines. Previous work from the inventors' has shown that monovalent vaccines utilizing the tumor antigens Globo H, Lewis$^y$, GM2, glycosylated MUC-1, Tn(c), sTn(c), or TF(c) conjugated to KLH to be safe with local erythema and edema but minimal systemic toxicities. As a result of vaccination with these monovalent vaccines, most patients generated specific high titer IgM or IgG antibodies against the respective antigen-KLH conjugates. The present invention provides a polyvalent vaccine wherein the components of the monovalent vaccines are combined and administered with an adjuvant as treatment for cancer.

SUMMARY OF THE INVENTION

The invention disclosed herein provides a polyvalent vaccine comprising at least two conjugated antigens selected from a group containing glycolipid antigen, polysaccharide antigen, mucin antigen, glycosylated mucin antigen and an appropriate adjuvant. This invention also provides the multivalent vaccine, comprising glycosylated MUC-1-32mer, Globo H, GM2, Le$^y$, Tn(c), and TF(c). This vaccine may comprise glycosylated MUC-1-G5, Globo H, GM2, Le$^y$, Tn(c), sTN(c), and TF(c). This invention provides the vaccine above, wherein the adjuvant is saponin-based adjuvant.

This invention also provides a method for inducing immune response in a subject comprising administering an effective amount of the vaccine above to the subject. Finally, this invention provides a method for treating cancer in a subject comprising administering an appropriate amount of the vaccine above to the subject.

DETAILED DESCRIPTION OF THE INVENTION

The invention disclosed herein provides a polyvalent vaccine comprising at least two conjugated antigens selected from a group containing glycolipid antigen, polysaccharide antigen, mucin antigen, glycosylated mucin antigen and an appropriate adjuvant.

The glycolipid includes but is not limited to Globo H, a Lewis antigen and a ganglioside. The Lewis antigen includes but is not limited to Le$^y$ and sialyl Le$^a$. The ganglioside includes fucosylated GM1, GM2, GD2, or GD3. In another embodiment, the mucin is a MUC peptide. In a further embodiment, the MUC peptide is MUC-1, MUC-2 or MUC-16. The polysaccharide antigen includes but is not limited to Tn(c), sTn(c), TF(c), and polysialic acid.

This invention provides a bivalent, trivalent, tetravalent, pentavalent, hexavalent, and heptavalent vaccine. The vaccine comprises at least two conjugated antigens selected from a group containing glycolipid antigen, polysaccharide antigen, mucin antigen, glycosylated mucin antigen and an appropriate adjuvant.

In an embodiment, the hexavalent vaccine comprises glycosylated MUC-1-32mer, Globo H, GM2, Le$^y$, Tn(c), and TF(c). In a further embodiment, the range of MUC-1-32mer is from about 0.1 to 30 ug. In yet another embodiment, the range of Globo H is from about 0.1 to 10 ug. In still a further embodiment, the range of GM2 is from about 0.1 to 10 ug. In an additional embodiment, the range of Le$^y$ is from about 0.1 to 60 ug. In a further embodiment, the range of Tn(c) is from about 0.1 to 10 ug. In an additional embodiment, the range of TF(c) is from about 0.1 to 30 ug.

In a separate embodiment, the adjuvant is saponin based. The adjuvant includes QS21 and GPI-0100. In an embodiment, the range of QS21 is from about 25 to about 200 ug. In another embodiment, QS21 is about 100 ug. In a separate embodiment, the adjuvant is GPI-0100 with a range from about 1 to 25 mg. In an embodiment, GPI-0100 is about 10 mg.

This invention provides a heptavalent vaccine comprising at least two conjugated antigens selected from a group containing glycolipid antigen, polysaccharide antigen, mucin antigen, and glycosylated mucin antigen and an appropriate adjuvant. In an embodiment, the vaccine comprises glycosylated MUC-1-G5, Globo H, GM2, Le$^y$, Tn(c), sTN(c), and TF(c). In another embodiment, the range of MUC-1-G5 is from about 0.1 to 30 ug. In a further embodiment, the range of Globo H is from about 0.1 to 100 ug. In another embodiment, the range of GM2 is from about 0.1 to 10 ug. In still another embodiment, the range of Le$^y$ is from about 0.1 to 60 ug. In an embodiment, the range of Tn(c) is from about 0.1 to 100 ug. In a further embodiment, the range of sTn(c) is from about 0.1 to 100 ug. In yet another embodiment, the range of TF(c) is from about 0.1 to 30 ug.

This invention provides the vaccine above, wherein the adjuvant is saponin-based adjuvant. These saponin-based adjuvants include but are not limited to QS21 and GPI-0100. In an embodiment, the range of QS21 is from about 25 to 200 ug. In another embodiment, the QS21 is about 10 ug. In a separate embodiment, the adjuvant is GPI-0100 and the range is from about 1 to 25 mg. In a preferred embodiment, GPI-0100 is about 10 mg.

This invention provides a polyvalent vaccine comprising a conjugated glycosylated antigen, a conjugated ganglioside antigen and an appropriate adjuvant, wherein the antigens are conjugated to a carrier. In an embodiment, the carrier is Keyhole Limpet Hemocyanin (KLH).

This invention provides the polyvalent vaccine above comprising at least two conjugated antigens selected from a group containing glycolipid antigen, polysaccharide antigen, mucin antigen, and glycosylated mucin antigen and an appropriate adjuvant for cancer. In an embodiment, the cancer is prostate, breast or ovarian cancer.

This invention also provides a method for inducing immune response in a subject comprising administering an effective amount of the above vaccine to the subject.

Furthermore, this invention provides a method for treating cancer in a subject comprising administering an appropriate amount of the above vaccine to the subject.

This invention also provides a composition comprising the above vaccine and a carrier.

This invention also provides a pharmaceutical composition comprising the above vaccine and a pharmaceutically acceptable carrier.

In addition, the invention provides a vaccine for small cell lung cancer comprising at least two conjugated antigens selected from the group containing Globo H, fucosylated GM1, GM2, GD2, GD3, sialyl $Le^a$ and polysialic acid. This invention also provides a method for inducing immune response in a subject bearing small cell lung cancer comprising administering an effective amount of the above vaccine to the subject. This invention furthermore provides a method for treating a subject bearing small cell lung cancer comprising administering an effective amount of the above vaccine to the subject.

In addition, this invention provides the above vaccine, further comprising an antigen selected from a group containing CA125, or a portion thereof, KSA peptide or protein, and PSMA, or a portion thereof.

This invention includes the above vaccines which further comprise other antigens which can induce antibody and/or immune response. As illustrated throughout the specification, the antigen used may be modified to increase its immunogenicity. Said antigens include but are not limited to CA125, or a portion thereof, KSA peptide or protein, and PSMA, or a portion thereof. As can be easily appreciated by the ordinary skilled artisan, only a portion of the antigen may be required for induction of immune response from a subject.

As stated herein, subjects are organisms which have immune response. The subject includes but is not limited to humans. Said subject could be domestic animals, such as dogs and cats.

This invention further provides the above compositions and a pharmaceutically acceptable carrier, thereby forming pharmaceutical compositions.

This invention also provides a pharmaceutical composition comprising a combination as described above and a pharmaceutically acceptable carrier. For the purposes of this invention, "pharmaceutically acceptable carriers" means any of the standard pharmaceutical carriers. Examples of suitable carriers are well known in the art and may include, but are not limited to, any of the standard pharmaceutical carriers such as a phosphate buffered saline solution and various wetting agents. Other carriers may include additives used in tablets, granules and capsules, etc. Typically such carriers contain excipients such as starch, milk, sugar, certain types of clay, gelatin, stearic acid or salts thereof, magnesium or calcium stearate, talc, vegetable fats or oils, gum, glycols or other known excipients. Such carriers may also include flavor and color additives or other ingredients. Compositions comprising such carriers are formulated by well-known conventional methods.

The invention will be better understood by reference to the Experimental Details which follow, but those skilled in the art will readily appreciate that the specific experiments detailed are only illustrative, and are not meant to limit the invention as described herein, which is defined by the claims which follow thereafter.

EXPERIMENTAL DETAILS

First Series of Experiments

Polyvalent (Hexavalent) Conjugate Vaccine for Prostate, Breast, Ovarian and Small Cell Lung Cancer Tumor-specific antigens have been identified and pursued as targets for vaccines. The inventors, previous work has shown that monovalent vaccines utilizing the tumor antigens Globo H, $Lewis^y$, GM2, glycosylated MUC-1, Tn(c), or TF(c) conjugated to KLH to be safe with local erythema and edema but minimal systemic toxicities. As a result of vaccination with these monovalent vaccines, most patients generated specific high titer IgM or IgG antibodies against the respective antigen-KLH conjugates. The present invention provides a hexavalent vaccine wherein the components of the monovalent vaccines are combined and administered with an adjuvant as treatment for prostate, breast, ovarian and small cell lung cancer.

A vaccine consisting of a unique combination of six tumor antigens administered with a saponin immunological adjuvant QS-21 or GPI-0100. The antigens are glycosylated MUC-1-32mer, Globo H, GM2, $Le^y$, Tn (c), and TF(c). In each case the antigen is conjugated to Keyhole Limpet Hemocyanin (KLH).

The preferred ranges of the antigen and adjuvant doses are as follows:

Glycosylated MUC-1-32mer: 0.1 to 30 µg;
Globo H: 0.1 to 100 µg;
GM2: 0.1 to 100 µg;
$Le^y$: 0.1 to 60 µg;
Tn(c): 0.1 to 10 µg;
TF(c): 0.1 to 30 µg;
QS-21: 100 µg;
GPI-0100: 1 or 25 mg.

Example 1

A Phase I Multivalent Conjugate Vaccine Trial for Patients with Biochemically Relapsed Prostate Cancer 1.0 PROTOCOL SUMMARY
2.0 OBJECTIVE
3.0 BACKGROUND AND RATIONALE
4.0 VACCINE PREPARATION
5.0 IMMUNIZATION SCHEDULE
6.0 PRE- AND POST-THERAPY EVALUATION
7.0 RESPONSE CRITERIA
8.0 BIOSTATISTICAL CONSIDERATIONS
9.0 REFERENCES 1.0 Protocol Summary:

This is a phase I pilot trial designed to assess safety using a multivalent conjugate vaccine. This trial is based on the results of eight dose-seeking phase I monovalent glycoprotein and carbohydrate conjugate vaccine trials which have been shown to be consistently immunogenic in man. These trails also allowed us to screen candidate antigens for their ability to generate high titer specific antibodies against the immunizing antigen. This vaccine will consist of the highest dose of synthetic glycoprotein and carbohydrate antigens shown to elicit high titer IgM and IgG antibodies in patients with biochemically relapsed prostate cancer. The inventors' previous work has shown the monovalent vaccines to be safe with local erythema and edema but minimal systemic toxicities. Among the antigens to be included in the multivalent vaccine are carbohydrate antigens Globo H and GM2 and the glycoprotein antigens glycosylated MUC-1-32mer, $Lewis^y$, Tn(c), and TF(c). The patient populations to be targeted are those patients who have failed primary therapies such as prostatectomy or radiation or have been on intermittent hormonal therapy and have remained hormonally sensitive in the absence of radiographic disease. These populations must have as the sole indication of disease progression, a rising PSA. The inventors' data from approximately 160 men who participated in earlier monovalent vaccine trials against the aforementioned antigens have shown that a treatment effect in the form of a decline in PSA log slopes compared with pretreatment values could be seen in patients with minimal tumor burden. A phase III double blind randomized trial with two hundred forty patients is planned based on the safety data accrued form this proposed phase I trial. The primary endpoint of the study will be the ability to assess the safety of the vaccine and the humoral response to a multivalent conjugate. Secondary endpoints will be to evaluate post-therapy changes in PSA.

2.0 Objectives:

2.1 The primary endpoints of the study are:

2.1.1 To determine the safety of a multivalent conjugate vaccine in patients with prostate cancer who have biochemically relapsed following primary therapies such as surgery or radiation.

2.1.2 Measure the antibody response against the individual components of the vaccine and to correlate the response to subsequent clinical course.

2.2. The secondary endpoints will be:

2.2.1 To assess post-immunization changes in prostate specific antigen levels and other objective parameters of disease (radionuclide bone scan and/or measurable disease if present.

3.0 Background and Rationale:

3.1 Prostate cancer: Over 180,000 cases of prostate cancer will be diagnosed in the United States in 2000.[1] Of these, 30-35% will present with tumors beyond the confines of the gland, while an additional 25% will develop metastases in the course of the disease despite local therapies. In these cases, a rising PSA antedates the development of overt metastases by a median of 12-24 months. Androgen ablation is the standard treatment with upwards of 70% of cases showing a normalization of an abnormal PSA after therapy. When to initiate treatment remains an area of controversy and there is no evidence that deferring therapy compromises outcomes. This observation, coupled with the fact that most patients relapsed within a median of 12-18 months[2], and that most men can not tolerate the side effects of castration including impotency, weight gain and hot flashes, has led to the search for alternative therapies. One such approach involves enhancing the body's own immune system as a means to treat local disease and prevent disease progression. PSA monitoring allows the identification of patients with low-volume disease, in whom an immunostimulatory approach may be more efficacious relative to a heavily pretreated, symptomatic population with large tumor burdens. Vaccinations represent a safe intervention with minimal toxicities that can be given as an adjuvant to surgery or radiation therapy in men at risk for systemic relapse. They can also be offered to men with minimal tumor burdens who are progressing and who are not willing to accept toxicities of hormonal therapy or chemotherapy. Because hormonal status may effect antigen expression and regulation, we propose to enroll patients with different hormone sensitivities. This will include patients who have not received hormonal therapy or have been on intermittent hormonal therapy.

3.2 PSA as an endpoint for clinical trials: The availability of serum PSA determinations provides a unique trial design for testing new therapies rapidly as changes in PSA levels over time correlate well with clinical outcomes.[3] This relationship holds for both hormone-naïve and hormonally relapsed disease. Once sequential elevations in PSA are documented in the setting of castrate testosterone levels, clinical symptoms develop in a median of 3-6 months. This observation justifies treatment in the setting of rising PSA values, using post-therapy changes in PSA as the outcome measure. With this design, therapeutic approaches that do not produce a defined degree of decline in PSA on multiple determinations for a defined duration (vide infra) are not evaluated further.[2]

3.3 Immunologic approaches: Augmentation of the immune response to cancer can be attempted by two basic approaches: non-specific immunopotentiation which constitutes the bulk of past and current efforts at cancer immunotherapy, and specific immunization which has not really been evaluated in the treatment of cancer but has contributed much to the control of infectious diseases. It is the knowledge of microbial antigens which has permitted the development of successful specific immunization against infections. The lack of availability of well-defined human cancer antigens, on the other hand, has prevented exploration of specific immunization in the context of cancer as it should be explored, using vaccines of defined cancer-restricted antigenicity and demonstrating their immunogenicity in cancer patients.

3.3.1 The role of carbohydrates and mucins in prostate cancer: Carbohydrate antigens have proven to be clinically relevant and (aside from vaccines against toxins) are the only defined bacterial antigens used in vaccines against bacterial pathogens. Immunization with carbohydrate antigens has also resulted in directed antibody responses against human tumor cells (reviewed in 4) presumably because these antibodies are known to mediate antibody-dependent cell-mediated and complement mediated lysis of tumor cells, complement-induced inflammation, and phagocytosis by the reticulo-endothelial system. The inventors' previous study in prostate cancer focused on defining the antigens expressed on the surface of prostate cancer cells.

3.3.2 Results with eight monovalent phase I trials using glycoprotein peptides and carbohydrate antigens. Immunohistochemistry using well-defined monoclonal antibodies against glycoprotein and carbohydrate antigens have shown that primary and metastatic prostate carcinoma specimens express these heretofore unknown antigens and that these molecules can serve as targets for immune recognition. We have studied two mucin peptide antigens, MUC-1 and MUC-2 conjugated to KLH and given with the immune adjuvant, QS21 in the phase I setting as a dose escalating trial with 10, 30 100 and 3 µg. Patients received five subcutaneous vaccines over the course of twenty-six weeks at weeks 1,2, 3, 7, and 19. Twenty patients were treated in the MUC-1-KLH-QS21 trial and fifteen were treated with MUC-2-KLH-QS21 trial. All patients developed high titer IgM and IgG antibodies specific for the immunizing peptide. Antibody titers rose by week 7 and declined usually by week 19, the time of the fifth and final vaccine. Unexpectedly, a treatment effect was observed after the vaccine trial was completed in the form of a declining PSA log slope compared with pretreatment values in approximately two-thirds of patients. In many patients, the slope began to show a decline by week 38 with subsequent declines by week 60. The initial decline corresponded to the rise of antibodies following the last immunization received at week 19. Five patients who were treated with the MUC-1-KLH conjugate in 1996 continue to have stable PSA log slopes without radiographic evidence of disease. Patients who were treated with MUC-2-KLH conjugate also demonstrated a similar treatment effect, however, the trial has not as yet reached maturity. The vaccines were found to be safe with erythema, tenderness and edema at the injection site. No evidence of autoimmunity or systemic toxicity was observed.

3.3.3 Experience with glycolipid and carbohydrate antigens. Eighteen patients have undergone immunization with Globo H, a glycolipid antigen expressed on prostate cancer cells. This is the first purely synthetic complex carbohydrate antigen used for immunization in man capable of generating high titer specific antibodies (median peak titer 1:320, IgG median titer 160) capable of mediating complement lysis of tumor cells. Several patients generated IgM antibody titers of 1:20,480). Patients were immunized with 10, 30 100 or 3 µg of Globo H-KLH plus QS21 over twenty-six weeks. Of the patients immunized with this vaccine, six remain active with stable PSA log slopes and no radiologic evidence of evidence of disease over the last 2½ years. This vaccine was found to be safe with no evidence of systemic toxicity. Ganglioside antigens (acidic glycosphingolipids expressing sialic acid at one end and ceramide at the other) was also investigated in a trial comparing the immunogenicity of higher doses of QS21. Using GM2-KLH at 30 µg, a dose previously established in melanoma trials, 18 patients were immunized with either the GM2 conjugate plus QS21 at the standard dose of 100 µg or QS21 at 225 Hg. Because of its potential for systemic toxicity, the latter vaccine was given as three separate immunizations to three separate sites as GM2-KLH at 10 µg plus QS21 at 75 µg subcutaneously. No difference in antibody titers were observed in two groups of patients; although two patients from the group given the higher dose of QS21 experienced grade II myalgias. Several patients also exhibited a decline in PSA log slopes but there did not appear to be any difference between groups with regard to treatment effects.

4.0 Vaccine Preparation

Globo H, Lewis$^y$, Tn(c), TF(c) are synthesized in the laboratory of Bio-Organic Chemistry headed by Dr. Samuel Danishefsky. MUC-1-32mer is synthesized in the Core Peptide Synthesis Facility of The Rockefeller Research Laboratories under the aegis of Dr. Paul Tempst. It is glycosylated with Tn by Dr. Henrik Clausen at the University of Copenhagen, Copenhagen, Denmark. GM2 is extracted from rabbit brains by Progenics, Inc., Tarrytown, N.Y.

4.1 Globo H. MUC-1-32mer, GM2, Lewis$^y$, Tn(c) and TF(c)-KLH conjugation: The above antigens will be covalently attached to KLH in Dr. Livingston's laboratory. Antigen-KLH ratios between 150/1 and 800/1 assuming a KLH molecular weight of $5\times10^6$ will be accepted. Gels will be performed and western blot analysis will be conducted with each lot of antigen-KLH for comparison to future lots. Sterility and safety testing with each lot plus QS21, at >50 times the dose/meter$^2$ to be used in clinical trials will be performed. No growth in culture and no adverse reaction in mice or Guinea pigs (including weight loss of 10% or more) will be tolerated. Two or more mice will be immunized with each antigen-KLH batch on 2-3 occasions at 1-2 week intervals and post immunization sera tested. Antibody titers of 1/200 or greater against antigen and 1/40 by IA or FACS staining of >25% of antigen positive cells will be accepted as proof that the construct has the appropriate immunogenicity.

4.2 Antigen Doses: Based on previous vaccine trials in prostate cancer patients, the following doses have been established for the multivalent trial: glycosylated MUC-1-32mer, 3 µg; Globo H, 10 g; GM2, 10 µg; Le$^y$, 10 µg; Tn(c), 3 µg; and TF(c), 3 µg. QS21 will be used at 100 µg as no significant difference in immunogenicity was observed with doses as high as 225 µg.

4.3 Safety testing: Samples from the materials are sent for sterility and safety testing. Immunogenicity of the individual peptides/carbohydrates have been previously confirmed in mice.

5.0 Immunization Schedule;

5.1 Patient selection: All patients with evidence of biochemical relapse will be considered. Hormonal status will be recorded on the basis of serum testosterone levels as follows: Patients who have progressed after primary surgery or radiation (with or without neo-adjuvant androgen ablation) who have non-castrate levels of testosterone (>50 ng/ml) will be eligible.

5.2 Interval: The immunization schedule that we will utilize was derived from the inventors' studies with other glycoprotein and carbohydrate conjugate vaccines in patients with melanoma, colon and breast cancers.

5.3 Treatment schedule and dose: Fifteen patients will be treated with specified doses of each carbohydrate or peptide constituent as has been determined previously based on earlier monovalent trials completed. QS21 will be administered at the standard dose of 100 ug. Sites: The vaccine conjugate will be administered subcutaneously to random sites on the upper arms and upper legs.

5.4 Dose modifications: If a patient experiences a Grade III or greater local or Grade II or greater systemic toxicity at any time a decrease by 50% in all components of future vaccinations will be administered for that patient.

6.0 Pre- and Post-Therapy Evaluation:

6.1 Outcomes: The study evaluation will include parameters to assess the safety of the vaccine, antitumor effect, as well as assessments of immune function. Interval safety assessments will include the Patient Diary. An overall antitumor assessment will be performed during weeks 13 and 26. If the patient has not demonstrated progression of disease at week 13 or 26, he will continue on protocol. Upon completion of the trial, he will be monitored every 3 months with bloodwork and imaging studies for the next 2 years or until disease progression.

6.2 Safety and antitumor effects:

| | STUDY WEEK | | | | | | | | |
|---|---|---|---|---|---|---|---|---|---|
| | $0^{a,c}$ | 1 | 2 | 3 | 7 | 9 | 13 | 19 | 26 |
| Clinical: | | | | | | | | | |
| Performance Status | X$^b$ | — | — | X | X | X | X | X | X$^h$ |
| Interval Hx & PE | X$^b$ | — | — | X | X | X | X | — | X |
| CBC, Diff, Plt. | X | — | — | X | X | — | X | — | X |
| CMP$^d$, LDH | X | — | — | X | — | — | X | — | X |
| Uric acid, Phosphorus | X | — | — | X | — | — | X | — | X |
| Prothrombin time | X | — | — | — | — | — | — | — | — |
| PSA, Ac. Phos | X | — | — | X | X | — | X | — | X |
| Testosterone | X | — | — | — | — | — | — | — | — |
| U/A | X | — | — | X | X | X | X | — | X |
| Stool guaiac | X | — | — | — | X | — | — | — | X |
| Pathology Review$^e$ | X | — | — | — | — | — | — | — | — |
| Imaging:$^f$ | | | | | | | | | |
| Chest X-ray | X | — | — | — | — | — | X | — | X |
| Bone scan | X | — | — | — | — | — | X | — | X |
| CT Scan or MRI | X | — | — | — | — | — | X | — | X |
| Overall response assessments$^g$ | — | — | — | — | — | — | X | — | X |
| Consent for Pathologic Correlates$^i$ | X | | | | | | | | |

$^a$Baseline studies prior to immunization.
$^b$Within 7 days of the first immunization.
$^c$Within 15 days of starting treatment for biochemical studies; 30 days for imaging studies. Includes total bilirubin, SGOT, LDH, Alkaline Phosphatase, Creatinine, BUN.
$^d$CMP Includes total bilirubin, SGOT, ALT, Sodium, Potassium, Chloride, $CO_2$, Calcium, Glucose, Total Protein, Abumin, Alkaline Phosphatase, Creatinine, BUN.
$^e$Patients will be asked to obtain tissue blocks from previous diagnostic/therapeutic procedures will be obtained and the patient's tumor evaluated for the presence of the antigens by immunohistochemistry. The presence of any antigen on paraffin material is not a criterion for entry and no biopsy procedures will be performed specifically for enrollment.
$^f$Abdominal and pelvic CT scans with and without contrast, chest x-ray and any other tests deemed necessary to document evaluable disease.
$^g$Overall response assessment includes the repetition of abnormal imaging and biochemical studies used to assess disease, and in selected cases, immune function.
$^h$Repeat at 3 month intervals for 2 years or until disease progression is documented.
$^i$Patients will be asked to sign a separate consent for pathologic correlative studies under IRB [90-40: Dr. H. Scher, P.I. - Molecular correlations in human prostate cancer].

6.3 Immune function:

|  | STUDY WEEK | | | | | | | | |
| --- | --- | --- | --- | --- | --- | --- | --- | --- | --- |
|  | 0 | 1 | 2 | 3 | 7 | 9 | 13 | 19 | 26 |
| VACCINATION* | — | 1 | 2 | 3 | 4 | — | — | 5 | — |
| B-CELL TESTING | — | 1 | 2 | 3 | 4 | 5 | 6 | 7 | 8 |

*No skin tests will be performed as previous trials indicated that there is minimal or no reactivity with intradermal administration of the antigens studied.

Antibody response: Peripheral blood (30 cc) will be drawn prior to vaccine immediately before each vaccination, as well as weeks 9, 13, and 26 to assess B-cell function. Thereafter, blood will be drawn at 3-month intervals (up to one year from the first vaccination), or as long as detectable immunity against the antigens persist. Depending on the antibody response, additional testing involving proliferation and cloning may be performed at a later date. The patients' sera will be tested by ELISA for antibodies against purified antigens as well as a variety of cell lines expressing (or not) the antigens included in the vaccine.

7.0 Response Criteria:

7.1 Patients WITHOUT bi-dimensionally measurable disease are evaluable by post-therapy changes in PSA as follows:

7.1.1 Complete Response (CR): Normalization of the PSA ($\leq$ 1.0 or 2.0 as defined in 4.1.1) for 3 successive evaluations at least 2 weeks apart.

7.1.2 Partial Response (PR); Decrease in PSA value by >50% above baseline (without normalization) for 3 successive evaluations.

7.1.3 Stabilization (STAB): Patients who do not meet the criteria for PR or PROG for at least 90 days will be considered stable.

7.1.4 Progression (PROG): Three consecutive increases in PSA, to >50% above baseline.

7.2 Duration of response: Non-measurable disease: Time from initiation of therapy until a 50% increase from the PSA nadir value is documented on three successive determinations.

8.0 Biostatistical Consideration 8.1 This is an exploratory study to study the safety of a multivalent conjugate vaccine which will be taken to phase III clinical trials. Patients with prostate cancer who have experienced a PSA recurrence after radical prostatectomy or radiation therapy are eligible. All fifteen patients will receive the same dose. The dose is based on previous vaccine trials in prostate cancer patients, the following doses have been established for the multivalent trial: glycosylated MUC-1-32mer, 3 µg; Globo H, 10 µg; GM2, 10 µg; Le$^y$, 10 µg; Tn(c), 3 µg; and TF(c), 3 µg. QS21 will be used at 100 µg as no significant difference in immunogenicity was observed with doses as high as 225 µg. Subjects will be followed for two years or until the development of metastatic disease. Bone scan and CT scans (or MRI where clinically appropriate) will be performed approximately at week 13, 26, and approximately every 3 months thereafter until the development of metastatic disease. In addition, PSA measurements will be obtained at weeks 3, 7, 13, 26, and every approximately 3 months thereafter in order to study the effect of the vaccine on the probability of developing metastatic disease and the effect of the vaccine on PSA slope over time, respectively.[24]

8.2 In order to be eligible for the study, patients must have a rising PSA following radical prostatectomy or radiation therapy. This detection of PSA following treatment must occur within two years. Using the ASTRO definition, three consecutive PSA rises are considered a biochemical failure after radical prostatectomy or radiation therapy. The date of failure should be the midpoint between the postsurgical (or postirradiation) nadir PSA and the first of the three consecutive rises.[25] In addition, patients must have a PSA doubling time (DT) less than 5 months. PSA doubling time is determined prior to treatment and is equal to ln(2) divided by the least squares derived slope of log PSA over time (log PSA slope>0.15).26 The time interval in which PSA DT will be based will consist of a minimum of three PSA measurements in a twelve-month interval prior to randomization. Patients who meet this requirement are considered at a higher risk for metastatic disease and will be eligible for this trial.

8.3 The primary objective of this study is to determine the safety and the humoral response of the multivalent vaccine in preparation for the phase III trial. The primary endpoint will be the time to radiographic progression of disease. The secondary objective is to study the rate of change in PSA over time.

REFERENCES

1. Wingo, P A, Tong, T, Bolden S: Cancer statistics, 1995. Ca Cancer J Clin, 45:8-30, 1999.
2. Scher, H I, Cordon-Cardo C: Current and future therapeutic strategies in metastatic hormonal resistant prostate cancer: therapy based on phenotype. Problems in Urology, 7:226-253, 1993.
3. Scher H I: Prostatic cancer: where do we go from here? Current Opin Oncol, 3:568-574, 1991.
4. Livingston, PO: Augmenting the immunogenicity of carbohydrate tumor antigens. Semin Cancer Biol, 6:357-366, 1995.
5. Itzkowitz S H, Bloom E J, Kokai W A, Modin G, et al: Sialosyl Tn: A novel mucin antigen associated with prognosis in colorectal cancer patients. Cancer 66:1960-1966, 1990.
6. Burchell, J, Taylor-Papadimitriou J, Boishell M, Gendler, S et al: A short sequence, with the amino acid tandem repeat of a cancer-associated mucin, contains immunodominant epitopes. Int J cancer 44:691-696, 1989.
7. Gendler S, Lancaster C, Taylor-Papadimitriou J, Duhig T, et al: Molecular cloning and expression of human tumor-associated polymorphic epithelial mucin. J Biol Chem 265:15286-15293, 1990.
8. Gendler S J, Spicer A P, Lalani E-N, et al: Structure and biology of a carcinoma-associated mucin, MUC1. Am Rev Res, 144:S42-S47, 1991.
9. Carrato C, Balague C, De Bolos C, Gonzalez E, Gambus G. et al: Differential apomucin expression in normal and neoplastic human gastrointestinal tissues. Gastroenterology, 107:160-172, 1994.
10. Ho S B, Niehans G A, Lyftogt C, Yan P s, et al: Heterogeneity of mucin gene expression in normal and neoplastic tissues. Cancer Res, 53:641-651, 1993.
11. Slovin, S. F., Livingston, P., Zhang, S., Keeperman, K. Mhatre, S., Adluri, S., Ghossein, R., Glazewski, J., Gordils, J., Danishefsy, S., and Scher, H. I.: Targeted therapy in prostate cancer (PC): vaccination with a glycoprotein, MUC-1-KLH-QS21 peptide conjugate. Proc Am Soc Clin Onc., 16:311a (Abstr 1107), 1997.
12. Slovin, S. F., Livingston, P., Keeperman, K., Mhatre, S., Danishefsky, S., Glazewski, J., Adluri, S., Zhang, S., Gordils, J., and Scher, H. I.: Targeted therapy in prostate cancer: vaccination with glycoprotein, MUC-1-KLH-QS21 peptide conjugate. J. Urol., 157:160 (Abstr 620), 1997.
13. Zing P X, Apostolopoulos V, Prenzoska J, et al: Petioled binding sites recognized by anti-mucin (MUC-2) antibodies. Scand J Immun, 591-592, 1994.
14. Slovin, S. F., Ragupathi, G., Donaldson, C., Olkiewicz, K., Terry, K., DePaolo, R., Livingston, P. O, and Scher, H. I.: MUC-2-KLH conjugate vaccine: Immunogenicity in patients with relapsed prostate cancer. Proc. Amer. Assoc. Cancer Res, 40:312(Abstr#2071), 1999.
15. Ragugpathi, G., Adluri, R., Amaravathi, R., Howarad, L., Gilewski, T., Slovin S. F., and Livingston, P. O.: Specificity analysis of sera from breast and prostate cancer patients vaccinated with MUC1-KLH and MUC-2-KLH conjugate vaccines. Proc. Amer. Assoc. Cancer Res, 40:312(Abstr #2070), 1999
16. Slovin, S. F., Livingston, P. O., Danishefsky, S., Mhatre, S., Ragupathi, R., Depaolo R., Sames, D., Terry K., Bauso, A., Kelly, W. K., Fazzari, M., and Scher, H. I.: Carbohydrate vaccines as immunotherapy for prostate cancer (PC): Globo-H-KLH conjugate plus QS21. Proc Am Soc Clin Onc, 17:433a (Abstr 1669), 1998.
17. Slovin, S F, Ragupathi G, Adluri S, Ungers G, Terry K, Kim S, Spassova M, Bornmann, W G, Fazzari M, Dantis L, Olkiewicz K, Lloyd K O, Livingston P O, Danishefsky S J, and Scher H I: Carbohydrate vaccines in cancer: Immunogenicity of a fully synthetic globo hexasaccharide conjugate in man. Proc Natl Acad Sci, USA, 96:5710-5715, 1999.
18. Slovin, S., Ragupathi, G., Israel, R., Terry, K., Bauso, A., Fazzari, M., Kelly, K., Reyes, S., Livingston, P., and Scher, H. Ganglioside vaccines in relapsed prostate cancer (PC): Experience with GM2-KLH conjugate plus the immunologic adjuvant, QS21-A trial comparing QS21 doses. Proc. Amer. Soc. Clin. Onc., 18:316 Aa(Abstr #1214), 1999.
19. Livingston P O, Natoli E J, Calves M J: Vaccines containing purified GM2 ganglioside elicit antibodies in melanoma patients. Proc natl Acad Sci USA, 27:537, 1987 (Abstract).
20. Slovin, SF, et al: Tn-cluster (c)-KLH/PAM vaccine conjugates in biochemically relapsed prostate cancer (PC): Phase I trial results. Proc. Amer. Assoc. Cancer Res, in press.
21. MacLean G D, Reddish M, Koganty, R R, Wong T, Gandhi S, Smolenski M, Samuel J, Nabholtz J M, and Longenecker B M: Immunization of breast cancer patients using a synthetic sialyl-Tn glycoconjugate plus Detox adjuvant. Cancer Immunol Immunotherap 36:215-222, 1993.
22. Zhang S, Walberg L A, Ogata S, Itzkowitz S H, Koganty R R, Reddish M, Gandhi S S, Longenecker B M, Lloyd K O and Livingston P O: Immune sera and monoclonal antibodies define two configurations for the sialyl Tn tumor antigen. Cancer Res 55:3364-3368, 1995.
23. MacLean G D, Bowen-Yacyshyn M B, Samuel J, Meikle A, Stuart G, Nation J, Poppema S, Jerry M, Koganty R, Wong T, and Longenecker B M: Active immunization of human ovarian cancer patients against a common carcinoma (Thompson-Friedenreich) determinant using a synthetic carbohydrate antigen. J Immunotherapy, 11:292-305, 1992
24. Scher, H. I, Slovin, S. F., Kelly, W. K., Livingston, P. O., Danishefsky, S., Fazzari, M., Terry, K. And Heller, Glen: Intermediate markers in assessing response to vaccine therapies. Proc Am Soc Clin Onc, 17:324a (Abstr 1247), 1998.
25. Patel, A, Dorey, F, Franklin, J, and DeKernion, J B: Recurrence patterns after radical retropubic prostatectomy: Clinical usefulness of prostate specific antigen doubling times and log slope prostate specific antigen. J Urol, 158:1441-1445, 1997.
26. O'Brien, PC, Fleming, T R: A multiple testing procedure for clinical trials. Biometrics 35:549-S56, 1979.

Example 2

Hexavalent Vaccine Immunogenicity Trial in Mice

Methods
Serological Analyses
1. ELISA (Enzyme-Linked Immunosorbent Assay):
ELISA assays were performed as described below. Antigen in ethanol or in 0.1 M carbonate buffer (pH 11) were coated on ELISA plates at 0.2 μg/well for glycolipids and 0.1 g/well for peptides. Serially diluted antiserum was added to each well and alkaline phosphatase-conjugated goat anti-mouse IgM or anti-mouse IgG was added at a dilution of 1:200 (Southern Biotechnology Associates, Inc, Birmingham, Ala.). Goat anti-mouse IgG and IgM conjugated with alkaline phosphatase obtained from Kierkegaard and Perry Labs, (Gaithersburg, Md.) were used as second antibodies. ELISA titer is defined as the highest dilution yielding an absorbance of 0.1 or greater over that of normal control mouse sera.
2. Cell Surface Reactivity Determined by FACS:
The cell surface reactivity of immune sera was tested on human cell lines. Single cell suspensions of $2 \times 10^5$ cells/tube were washed in PBS with 3% fetal calf serum (FCS) and 0.01M $NaN_3$ and incubated with 20 μl of 1:20 diluted sera or monoclonal antibody mAb for 30 min on ice. After two washes with 3% FCS in PBS, 20 μl of 1:15 diluted goat anti-mouse IgM or IgG-labeled with fluorescein-isothiocyanate (FITC, Southern Biotechnology Associates Inc. Birmingham, Ala.) was added, and the mixture incubated for 30 min. After a final wash, the positive population and mean fluorescence intensity of stained cells were differentiated using FACScan, Becton & Dickinson Immunocytometry, San Jose, Calif.
Appendix B

| Hexavalent Vaccine immunogenicity Trial in Mice |
| --- |
| Four female CB6F1 mice were vaccinated weekly for three weeks with Hexavalent vaccine (Hexavalent vaccine in Polyval-KLH conjugate plus 20ug QS21 per mouse). The injections were SC, at 2 sites, with 95ul/site. [Vial labeled Polyval in Polyval-KLH conjugate plus 100ug QS21/1.0 ml. Total vol. 1.0 ml. Lot # 081100] Pre-vaccination sera was drawn from each mouse. Sera was drawn again at 10 days post third vaccination. The mice were weighed prior to and post vaccination (at 24 hr post, at 48 hr post, at one week post and at 2 weeks post). |

-continued

For controls, the following monoctonal antibodies were used:

| | |
|---|---|
| VK9 | anti-Globo-H |
| BR96 | anti-Le$^y$ |
| HMFG1 | anti-MUC1 |
| αTn Ab | anti-Tn |
| αGM2 Ab | anti-GM2 |
| 49H.8 | anti-TF |

SEROLOGY

ELISA plates were coated with 0.1 ug/well of one of the following antigens: GloboH-ceramide, GM2(IgM), MUC1G5, Tn-'HSA, Tf-'HSA
ELISA plates were coated with 0.2 ug/well of one of the following antigens: GM2 (IgG). Ley
Sera was tested at an initial dilution of 1:40, with subsequent 2-fold dilutions
(with the exception of GloboH for which 3-fold dilutions were used).
FACS analysis was performed on two cell lines: MCF7 and LSC (5 × 10$^8$ cells per tube).
Sera was added at a 1:20 dilution (25 ul/tube).
Each post 3rd vacc. sera was set against its corresponding pre-sera (each pre-sera was set at 10%).

Appendix B Results
ELISA

| | Globo H | | | | GM2 | | | | Le$^Y$ | | | |
|---|---|---|---|---|---|---|---|---|---|---|---|---|
| | IgG | | IgM | | IgG | | IgM | | IgG | | IgM | |
| Mouse # | presera | post 3rd | presera | post 3rd | presera | post 3rd | presera | post 3rd | presera | post 3rd | presera | post 3rd |
| 1 | 0 | 40 | 120 | 1,080 | 40 | 40 | 40 | 80 | 0 | 40 | 80 | 640 |
| 2 | 0 | 80 | 40 | 3,240 | 40 | 40 | 40 | 80 | 0 | 40 | 80 | 80 |
| 4 | 0 | 360 | 120 | 3,240 | 0 | 0 | 0 | 80 | 0 | 40 | 40 | 640 |
| 5 | 0 | 40 | 0 | 3,240 | 0 | 40 | 0 | 80 | 0 | 160 | 40 | 320 |
| +control | VK9 1:25,600 | | | | αGM2 >>>1:1,000,000 | | | | BR96(1ug/ul) 1:3,200 | | | |

| | MUC1G5 | | | | Tf-'HSA | | | | Tn-'HSA | | | |
|---|---|---|---|---|---|---|---|---|---|---|---|---|
| | IgG | | IgM | | IgG | | IgM | | IgG | | IgM | |
| Mouse # | presera | post 3rd | presera | post 3rd | presera | post 3rd | presera | post 3rd | presera | post 3rd | presera | post 3rd |
| 1 | 0 | 10,240 | 0 | 80 | 0 | 640 | 0 | 80 | 0 | 1,280 | 0 | 80 |
| 2 | 0 | 20,480 | 0 | 320 | 0 | 640 | 0 | 160 | 0 | 640 | 0 | 5,120 |
| 4 | 0 | 5,120 | 0 | 40 | 0 | 5,120 | 0 | 160 | 0 | 10,240 | 0 | 640 |
| 5 | 0 | 10,240 | 0 | 160 | 0 | 10,240 | 0 | 160 | 0 | 10,240 | 40 | 640 |
| +control | | | | | 49H.8 1:1,500 | | | | aTn 1:25,600 | | | |

FACS

| | MCF7 | | | | | | LSC | | | | | |
|---|---|---|---|---|---|---|---|---|---|---|---|---|
| | IgG | | IgM | | | | IgG | | IgM | | | |
| Mouse # | presera | post 3rd | presera | post 3rd | +controls | | presera | post 3rd | presera | post 3rd | +controls | |
| 1 | 10.02% | 95.76% | 11.52% | 89.79% | VK9 | 1.13% | 10.11% | 42.28% | 9.63% | 58.23% | VK9 | 0.95% |
| 2 | 10.49% | 95.30% | 10.48% | 95.61% | BR96 | 97.11% | 9.60% | 28.88% | 10.75% | 93.47% | BR95 | 94.85% |
| 4 | 9.78% | 94.71% | 11.36% | 95.96% | HMFG1 | 62.31% | 9.93% | 27.09% | 11.12% | 96.28% | HMFG1 | 1.19% |
| 5 | 9.78% | 95.48% | 9.86% | 94.49% | αTn Ab | 78.62% | 10.59% | 23.46% | 10.16% | 93.23% | αTn Ab | 57.63% |
| 2° Ab alone | | 1.28% | | 1.15% | αGM2 Ab | 94.91% | | 1.18% | | 1.14% | αGM2 Ab | 63.94% |
| | | | | | 49H.8 | 0.14% | | | | | 49H.8 | 0.26% |

Second Series of Experiments

Polyvalent (Heptavalent) Conjugate Vaccine for Prostate, Breast, Ovarian and Small Cell Lung Cancer Tumor-specific antigens have been identified and pursued as targets for vaccines. The inventors' previous work has shown that monovalent vaccines utilizing the tumor antigens Globo H, Lewis$^y$, GM2, glycosylated MUC-1, Tn(c), sTn(c), or TF(c) conjugated to KLH to be safe with local erythema and edema but minimal systemic toxicities. As a result of vaccination with these monovalent vaccines, most patients generated specific high titer IgM or IgG antibodies against the respective antigen-KLH conjugates. The present invention provides a heptavalent vaccine wherein the components of the monovalent vaccines are combined and administered with an adjuvant as treatment for prostate, breast, ovarian and small cell lung cancer.

A vaccine consisting of a unique combination of seven tumor antigens administered with a saponin immunological adjuvant QS-21 or GPI-0100. The antigens are glycosylated MUC-1-G5, Globo H, GM2, Le$^y$, Tn(c), sTn(c), and TF(c). In each case the antigen is conjugated to Keyhole Limpet Hemocyanin (KLH).

The preferred ranges of the antigen and adjuvant doses are as follows:
Glycosylated MUC-1-G5: 0.1 to 30 µg;
Globo H: 0.1 to 100 µg;
GM2: 0.1 to 100 µg;
Le$^y$: 0.1 to 60 µg;
Tn(c): 0.1 to 100 µg;
sTn(c): 0.1 to 100 µg;
TF(c): 0.1 to 30 µg;
QS-21: 25-200 µg;
GPI-0100: 1-25 mg.

Example 1

Phase I clinical trial protocol using the heptavalent vaccine

Example 2

Heptavalent vaccine immunogenicity trial in mice
1. Methods
2. Results

Example 1

Pilot Phase I Trial in Patients with Epithelial Ovarian, Fallopian Tube, or Peritoneal Cancer with a Polyvalent Vaccine-KLH Conjugate+Qs-21

1.0 PROTOCOL SUMMARY
2.0 OBJECTIVE
3.0 BACKGROUND AND RATIONALE
4.0 VACCINE PREPARATION
5.0 TREATMENT SCHEDULE AND DOSE
6.0 EVALUATION DURING STUDY
7.0 BIOSTATISTICAL CONSIDERATIONS (Endpoints)
8.0 BIBLIOGRAPHY
1.0 Protocol Summary and Program Plan Patients with epithelial ovarian, fallopian tube, or peritoneal cancer who receive surgical cytoreduction and platinum/taxane containing chemotherapy have a significant chance of entering complete clinical remission but unfortunately approximately 70% will eventually relapse. These patients in clinical remission have minimal residual disease, and are excellent candidates in which to evaluate novel consolidation strategies in an attempt to improve outcome. This pilot polyvalent protocol represents the culmination of a series of monovalent phase I vaccine trials at the center demonstrating the immunogenicity of the various component antigens. It represents the transition between the phase I monovalent trial program in second remission, to the planned development of larger trials designed to evaluate efficacy. Immunization with the individual antigens selected for this vaccine has been consistently immunogenic in the majority of patients. No confirmed systemic toxicity has occurred related to vaccine administration. It is expected that the immunogenicity will remain unchanged, and that no systemic toxicity will occur with polyvalent vaccine administration. Eligible patients for this pilot trial are those patients initially with stage II-IV disease in complete clinical remission following primary therapy, or following relapse and re-induction to remission with additional chemotherapy. In this trial, patients will receive an antigen defined vaccine with the following ganglioside components: a) GM2, b) Globo-H; the blood group related antigens: c) TF(c), d) s-Tn (c), e) Tn (c) f) Lewis-Y; and g) the protein antigen MUC-1-G5 (glycosylated). The primary endpoints of this pilot study are safety, and confirmation of continued immunogenicity. The secondary endpoint will be to characterize the nature and duration of the antibody response.

2.0 Objectives 2.1 The primary endpoints of this pilot study are to determine the safety of polyvalent vaccine administration, and continued immunogenicity in patients prior to conducting a large, randomized study.

2.2 The secondary endpoint is to further characterize the nature and duration of the antibody response generated by the polyvalent vaccine (ELISA and FACS)

3.0 Background and Rationale 3.1 Disease Background and Suitability for Treatment In 1999, approximately 22,500 new cases of ovarian cancer were diagnosed, and it is estimated that 14,500 women died of the disease. Seventy-five percent of patients with ovarian cancer will have spread beyond the ovary at diagnosis. Standard primary treatment consists of cytoreductive surgery followed by a platinum and paclitaxel containing chemotherapy regimen.[1] Many patients have no clinically measurable disease at the end of primary treatment. A review of second-look laparotomy, however, indicates that less than 50% of patients are actually free of disease.[2] Furthermore, nearly half of patients with a negative second look procedure are destined to relapse and require additional treatment.[3,4] Overall, only approximately 30% of patients remain disease free with currently available treatment. Given the minimal disease burden at the completion of primary therapy, these patients are ideal candidates in which to evaluate immune modulating strategies.

3.2 Rationale for Polyvalent Vaccines Designed Primarily for Antibody Production Varied data exists in solid tumors to support the development of immune directed therapy. Studies have emerged in patients with melanoma which demonstrate that naturally acquired 5,6, or actively induced[7,8] antibodies may improve outcome. In a large clinical trial reported by Reithmuller et al., 189 patients with resected Dukes C colon carcinoma were randomized to receive observation versus postoperative treatment with murine antibody CO17-1A that recognizes the KSA antigen. Toxic effects were limited to infrequent constitutional symptoms. At median follow-up of five years, the death rate was 36% in the treated group versus 51% in the observed group. The advantage of treatment was demonstrated in univariate ($p=0.051$) and multivariate ($p=0.043$) analysis when controlling for other known prognostic factors.[9]

The basis for cancer vaccines designed primarily for antibody induction are the many preclinical models demonstrating the ability of passively administered or actively induced antibodies to prevent tumor recurrence[10], the increasing number of clinical trials where passively administered monoclonal antibodies have demonstrated clinical efficacy, and the correlation of antibodies, naturally acquired or vaccine induced, with improved prognosis in several different clinical settings.[6]

EL4 lymphoma naturally expresses GD2 ganglioside, which is recognized by monoclonal antibody 3F8. Vaccines containing GD2 covalently conjugated to KLH and mixed with immunological adjuvant QS21 are the optimal approach to vaccination against GD2. Relatively higher levels of antibody administered two or four days after intravenous tumor challenge or moderate titers induced by vaccine that were present by day two or four after tumor challenge were able to eradicate disease in most mice. If antibody administration was deferred until day seven or ten, little or no benefit could be demonstrated. If the number of cells in the EL4 challenge was decreased, giving a longer window of opportunity, the vaccinations could be initiated after tumor challenge and good protection seen.[7] These results are consistent with the need to initiate immunization with vaccines inducing antibodies in the adjuvant setting, when the targets are circulating tumor cells and micrometastases. Patients with ovarian cancer in first remission meet these criteria, and unfortunately have a high "event rate" (ie. 80% will relapse) allowing for the rapid assessment of the efficacy of this approach.

The basis for the inventors' emphasis on polyvalent vaccines is tumor cell heterogeneity, heterogeneity of the human immune response and the correlation between overall antibody titer against tumor cells and effector mechanisms such as complement mediated cytotoxicity (CDC) or antibody dependent cell mediated cytotoxicity (ADCC). For example, using a series of 14 tumor cell lines and monoclonal antibodies (mAbs) against 3 gangliosides, investigators at MSKCC have shown that significant cell surface reactivity analyzed by flow cytometry and CDC increased from 2-8 of the cell lines using one of three mAbs to 13-14 of the cell lines when the 3 mAbs were pooled. The median CDC increased 4 fold with the pool of mAbs compared to the best single mAbs.[11] Cancers of the ovary express a rich array of cell surface antigens making them especially suitable targets for polyvalent vaccines.

Cell surface antigens (especially carbohydrate cell surface antigens) have proven to be unexpectedly potent targets for immune recognition and attack of human cancers. Many of the more tumor-restricted monoclonal antibodies derived by immunization of mice with human tumor cells have been found to be directed against carbohydrate antigens expressed at the cell surface[12] Immunization against carbohydrate antigens results generally in an antibody response (see references for dissenting views), which is primarily IgM.[13-15] These antibodies are known to induce CDC, inflammation, and phagocytosis of tumor cells by the reticulo-endothelial system (opsonization).[16] Immunization against cell surface protein antigens can induce a variety of B and T lymphocyte responses. The T lymphocyte responses are difficult to quantify in the context of vaccination trials and are not the focus of this proposal. The antibody responses against protein antigens contain IgM and IgG, both of which can induce complement activation (with regard to IgG depending on the subclass, IgG1 and IgG3 being optimal). IgG antibodies of these subclasses can also induce ADCC.

Antibodies are the primary mechanism for active elimination of circulating pathogens from the bloodstream. They are ideally suited for eradication of free tumor cells and systemic or intraperitoneal micrometastases and they have accomplished this as described above in a variety of preclinical mouse experiments (reviewed in references).[10,7] In adjuvant immunization trials, the primary targets are individual tumor cells or early micrometastases which may persist for long periods after apparent resection of all residual tumor.[17] After surgery and completion of chemotherapy is the ideal time for immune intervention, and in particular for administration of cancer vaccines aimed at instructing the immune system to identify and kill the few remaining cancer cells. If antibodies of sufficient titer can be induced against tumor antigens to eliminate tumor cells from the blood and lymphatic systems, aggressive local therapies, including surgery, radiation therapy and intralesional treatments might result in long term control of even metastatic cancers.

3.3 Preliminary Studies for the Antigens

GM2 vaccines: Investigators at the center have been refining the ability to induce antibodies against GM2 in melanoma patients for fifteen years, since first demonstrating that vaccines containing purified GM2 could be more immunogenic than vaccines containing tumor cells expressing GM2.18 Initially GM2 adherent to BCG was selected as optimal, inducing IgM antibodies in 85% of patients. This was the basis for a randomized trial comparing immunization with BCG to immunization with GM2/BCG in 122 patients with AJCC Stage 3 melanoma.[8] The IgM antibodies had a median titer of $\frac{1}{160}$ and were short lived (8-12 weeks). IgG antibody induction was rare. Antibody titers have been maintained for over three years by administration of repeated booster immunizations at 3-4 month intervals. When comparing patients as randomized in this trial, no statistically significant difference on overall or disease free survival was seen. Pre-existing GM2 antibodies were seen in 5 patients in the control group, as opposed to one in the GM2 treated group which may have blunted the treatment result. The association between better outcome and the presence of GM2 antibodies was seen (8).

TF, Tn and sTn vaccines: Patients with various epithelial cancers have been immunized with unclustered TF-KLH and sTn-KLH conjugate vaccines plus various adjuvants.[19] High titer IgM and IgG antibodies against TF and sTn antigens have resulted, but we found that the majority of the reactivity detected in sera from immunized mice and patients was against antigenic epitopes present on synthetic constructs which were not present on naturally expressed mucins.[20] Based on previous studies with Tn antigen, 21 Kurosaka and Nakada et al. hypothesized that MLS102, a monoclonal antibody against sTn, might preferentially recognize clusters (C) of sTn. In studies at MSKCC with monoclonal antibody B72.3 and with sera raised against TF-KLH and sTn-KLH conjugate vaccines in mice and in patients resulted in the same conclusion.[20,22] The availability of synthetic TF, Tn and sTn clusters consisting of 3 epitopes covalently linked to 3 consecutive serines or threonines has permitted investigators at MSKCC to prove this hypothesis. In both direct tests and inhibition assays, B72.3 recognized sTn clusters exclusively, and sera from mice immunized with sTn (C)-KLH reacted strongly with both natural mucins and tumor cells expressing sTn.[22] Based on this background, we initiated trials with the TF(C)-KLH, Tn(C)-KLH and sTn(C)-KLH conjugate vaccines in patients with breast cancer. Antibodies of relevant high titer specificity, including against OSM or PSM and cancer cells expressing TF, Tn or sTn, have been induced for the first time in the inventors' experience. Based on these results confirming the importance of clustered epitopes and defining their relevant immunogenicity, we are including these clustered antigens in the polyvalent vaccine against ovarian cancer.

Le$^y$ and Globo H vaccines: The development of Le$^y$ and Globo H vaccines was previously limited by the lack of sufficient quantities of antigen for vaccine construction and testing. Over the last four years, Dr. Danishefsky has successfully synthesized both antigens.[23, 24] Investigators at MSKCC have immunized groups of mice with Globo H-ceramide plus or minus adjuvants QS-21 and *Salmonella* minnesota mutant R595, and with Globo H covalently attached to KLH or BSA plus immunological adjuvant QS-21. The highest antibody titers against both synthetic antigen and MCF7 cells expressing Globo H were induced by the Globo H-KLH plus QS-21 vaccine.[23,24] The antibody titer induced against synthetic Globo H was $\frac{1}{120,000}$ by ELISA, the titer induced against MCF7 was $\frac{1}{320}$, and potent complement mediated cytotoxicity was seen as well. Le$^y$-BSA and Le$^y$-KLH vaccines have also been tested in the mouse. High titer antibody responses have resulted against the synthetic epitope of Le$^y$ and against tumor cells expressing Le$^y$ in the majority of mice immunized.[25] Based on these results, monovalent phase I clinical trials with Globo H-KLH plus QS-21 and Le$^y$-KLH plus QS21 have been initiated in patients with breast, prostate or ovary cancer. Antibodies against the purified antigens and against tumor cells expressing these antigens were induced in most patients and the manuscript was recently published for the latter.[26,27]

MUC1 and MUC2 vaccines: Investigators at MSKCC have immunized mice with MUC1-KLH and MUC2-KLH, plus QS-21, and seen induction of consistent high titer IgM and IgG antibodies against MUC1 and MUC2 and human cell lines expressing MUC1 and MUC2, as well as protection from a syngeneic mouse breast cancer expressing human MUC1 as a consequence of gene transduction. Mice were also immunized with vaccines containing MUC1 peptides of various lengths conjugated to KLH by one of three methods or not, and mixed with QS-21 or BCG. MUC1 containing 30 amino acids or more, conjugated to KLH with an MBS bifunctional linker and mixed with immunological adjuvant QS-21 induced the highest titer antibodies.[28] Based on these studies in the mouse, a trial was initiated and completed a trial with this MUC1-KLH plus QS-21 vaccine in breast cancer patients who were free of detectable breast cancer after resection of all known disease. Nine patients were treated with a 31 amino acid MUC1 peptide with cysteine at one end for conjugation to KLH and the immune dominant epitope-AP-DTRPA at the other end.[29] No patient had detectable MUC1 serological reactivity by ELISA or FACS prior to immunization. The results are summarized below in table below. Reactivity against MUC1 and tumor cells expressing MUC1 was seen in most patients. A separate group of patients were immunized with MUC2-KLH plus QS21. Analysis of this trial is not yet complete, but the results to date are also summarized in the table below.

The inventors have been unable to demonstrate T-lymphocyte proliferation, interferon γ and IL4 release by ELISPOT assays, CTL activity or positive DTH responses after vaccination with MUC1 or MUC2. The proliferation assays were particularly focussed on in the MUC1 trials. Patients had leukophoresis pre and post vaccination, providing ample lymphocytes for study. After 2 years of steady endeavor, there has been no clear evidence of augmented reactivity against MUC1 peptides of various lengths or, in HLA A2 positive patients against heteroclytic MUC1 peptides with single amino acid changes that increased binding to HLA A2. (personal communication, P.O. Livingston) Pre and post vaccination PBLs from the first 6 patients vaccinated with MUC1 were also sent to the laboratory of Dr. Olivera Finn for CTL precursor frequency analysis. No increase in frequency was seen. Over all, the major difference between results from MSKCC with the 31aa MUC1-KLH plus QS-21 vaccine and Dr. Finn's results with a 104aa MUC1 peptide plus BCG vaccine was that the former had a clearly demonstrable, consistent antibody response, which was reactive with tumor cells. Inhibition assays were performed to better understand this serologic response.[30] Much of the IgM response and nearly all of the IgG response were against the immune dominant epitope, APDTRPA, preferentially with RPA at the terminal position.

KSA vaccines: KSA has been prepared in the baculovirus system by Jenner Technologies (San Ramon, Calif.) and 10 mcg/patient has been provided for testing. Due to the small quantity of KSA available, following demonstration of relevant immunogenicity in mice, we treated groups of 9 patients with KSA plus QS21 or with KSA covalently linked to KLH by glutaraldehyde, plus QS21. In neither case was there significant induction of antibodies against KSA that had not been glutaraldehyde treated, or tumor cells expressing KSA. Consequently KSA will not be included in the polyvalent vaccine. The results of this and the other trials with KLH conjugate vaccines are summarized in the table below (personal data, P. O. Livingston).

Summary of Serological Results in Vaccinated Patients

| Antigen | Median ELISA | | IgG | Median FACS | | Median IA | Median CDC |
|---|---|---|---|---|---|---|---|
| | IgM | IgG | Subclass | IgM | IgG | | |
| GM2 | 640 | 320 | IgG1 + 3 | +++ | ++ | ++ | ++ |
| Globo H | 640 | 40 | IgG1 + 3 | ++ | + | ++ | + |
| Lewis$^y$ | 80 | 0 | | ++ | + | + | + |
| Tn | 1280 | 1280 | | ++ | − | + | − |
| STn | 1280 | 160 | IgG3 | +++ | − | + | − |
| TF | 320 | 10 | | | | + | − |
| MUC1 | 1280 | 5120 | IgG1 + 3 | + | − | + | − |
| MUC2 | 2560 | 2560 | | pending | | | |
| KSA | 40 | 160 | | − | − | − | − |

Additional variables: Two additional variables have proven critical, the method of conjugation and the epitope ratio of antigen molecules per KLH molecule. The optimal conjugation approached has varied with the antigen. Gangliosides are best conjugated using ozone cleavage of the ceramide double bond and introducing an aldehyde group followed by coupling to aminolysyl groups of KLH by reductive amination. This approach was not as effective for conjugation of Tn, sTn and TF clusters or Globo H to KLH where an M2C2H linker arm has proved most efficient[31] or for MUC1 or MUC2 where an MBS linker group was optimal.[28]

The impact of dose and schedule of vaccine administration on antibody response to GM2 vaccines in melanoma patients has also been explored. Immunization 4 times at weekly intervals or biweekly intervals followed by booster immunizations twice at 2-3 month intervals was compared to 6 immunizations at monthly intervals. Initial immunizations at weekly or biweekly intervals resulted in comparable high titers (with high titers occurring slightly sooner at weekly intervals), but remarkably the monthly immunizations resulted in far weaker or undetectable antibody responses in the 6 patients vaccinated.[32] GM2-KLH plus QS-21 vaccines prepared at MSKCC and at Progenics Pharmaceuticals have each been tested in dose finding studies such as those proposed in this application. In both cases GM2 doses of 3 ug or less resulted in lower IgM titers and undetectable IgG titers in most patients. GM2 doses of 10, 30 and 100 ug gave comparable IgM and IgG titers.[33] Based an these studies, we have selected the initial weekly schedule of 3-4-immunizations followed by booster immunizations every three months, and the doses for use in the randomized Phase III trial.

3.4 Potential Toxicity of Vaccination

The expected safety of the vaccine is based on the safety of vaccination with the individual components. Clinical experience is growing in clinical trials with vaccine induced antibody responses against each of the included antigens. Antigen expression at secretory borders in these trials, where the majority is located, has induced neither immunological tolerance nor symptomatic autoimmunity once antibodies are present, suggesting they are sequestered from the immune system. Nevertheless, a regular schedule of laboratory studies and physical examinations are designed to detect any abnormalities. This pilot trial will represent one of the first studies to confirm the safety of polyvalent vaccine administration in this setting.

3.5 General Immune Approaches

Various methods have been used to increase the immunogenicity of antigens, and in particular for inducing an IgG response. In preclinical laboratory studies, we have found the covalent attachment of antigen to keyhole limpet hemocyanin (KLH) to be most effective.[34] KLH is well tolerated, and has previously caused only mild inflammation at the vaccine injection site. Attachment of KLH may be accomplished by a variety of cross-linking methods. MBS (m-maleimidobenzoly-N-hydroxysuccinimide ester) is the best-known heterobifunctional reagent; and at neutral pH cross-links thiol groups with amino groups. The linkage proceeds via two separate reactions, thus limiting bonds between identical molecules. In addition to linking antigen to immunogenic carrier proteins, the titer of antibody induced may be further augmented with the use of appropriate immunological adjuvants. We have immunized groups of melanoma patients with vaccines either containing no adjuvant, or using DETOX, BCG or QS-21. QS-21 is a significantly more effective adjuvant than the others, producing significantly higher titer IgM and IgG antibodies. It is a saponin derivative extracted from the bark of the South American tree Quillaja saponaria Molina. The monosaccharide composition, molecular weight, adjuvant effect and toxicity for a series of these saponins have been described.[35,36] It has also proven to be non-toxic and effective at augmenting the immunogenicity of an FeLV subunit vaccine in cats 37 and an HIV-1 recombinant vaccine in Rhesus monkeys. A phase I trial demonstrating the safety and suggesting the efficacy of a 100 ug QS-21 dose in patients treated with GM2-KLH vaccines has been reported. The only adverse events reported were minimal flu-like symptoms, and mild discomfort at the injection site.[38] Thus, conjugation with KLH and the addition of QS-21 have become standard approaches for vaccine construction at MSKCC has proven optimal for antibody induction against a variety of gangliosides, MUC1, MUC2, KSA, Tn, sTn, TF, Le$^y$ and Globo H in the mouse and in humans.

3.6 Distribution of the antigens studied: In general, the antigens contained in this vaccine are expressed on ovarian cancer cells with high frequency. Recent studies at MSKCC have characterized this distribution in a variety of tumor types including ovarian cancer using immunohistochemical staining. A variety of tumor specimens were used in each tumor type, and it was required that 50% or more cells be positive in order to consider the antigen present. The presence of these antigens on the tumor specimens tested in ovarian cancer was: GM2 (100%), GLOBO-H (60%), MUC 1 (100%), sTn (60%), TF (100%), Le Y (80%).[39-41]

3.7 Rational for the inventors' approach: The inventors' hypothesis is that induction of an antibody response against several cell surface antigens on ovarian cancer cells with a polyvalent conjugate vaccine will result in eradication of free tumor antigen, circulating tumor cells and micrometastases. The polyvalent nature of the vaccine and antibody response is important to eliminate escape by tumor cells that fail to express any one or two of the antigens, and to increase the number of antibodies reacting against each cell. It is expected that the inventors' vaccine will prove consistently immunogenic against five or six of the ovarian cancer cell surface antigens described above, and that it will prove nontoxic. Whether immunization with this polyvalent vaccine in high-risk ovarian cancer patients in the remission setting will result in prolonged disease-free and overall survival is the focus of subsequent studies to follow this pilot trial.

4.0 Vaccine Preparation 4.1 GM2 is provided by Progenics. GLOBO-H, Lewis-Y, TF(c), Tn (c), and sTn (c) are synthesized in the laboratory of Dr. Sam Danishefsky at the center. MUC-1 is produced at the core facility at MSKCC. For glycosylation, the MUC-1 was shipped to the University of Copenhagen, Glycobiology Group. The glycosylation was carried out by GalNAc transferase using UDP-N-GalNAc as substrate. The product was shipped back to MSKCC after purification by reverse phase HPLC.

4.2 QS-21 is obtained from Aquila Biopharmaceuticals in 100 mg vials as a white powder and is stored at −30 degrees Celsius. This is suspended initially in PBS as it is less soluble in normal saline and then final dilutions are made in normal saline. QS-21 is passed through a 0.22 micrometer filter immediately prior to use.

4.3 Conjugation to KLH is accomplished with three different conjugation procedures: direct amination (ozonolysis) for GM2, the M2C2H bifunctional linker group for Globo H and Le Y, and the MBS bifunctional linker group for the four mucin antigens.

4.4 The sterility of the conjugate is confirmed by passage through a 0.22 micrometer filter and it is stored in frozen normal saline at −30 to −80 degrees Celsius.

4.5 Vials are released for use following standard lot release testing (approximately five weeks).

5.0 Treatment Schedule and Dose 5.1 Vaccine contains:

[GM2(10 mcg)/TF(c)(3 mcg)/sTn(c) (3 mcg)/Globo-H(10 mcg)/MUC1-1-G5(3 mcg)/Le$^Y$ (10 mcg)/Tn(c) (3 mcg)]-KLH (≈400 mcg) with adjuvant QS21(100 mcg)

5.2 Immunization Schedule

The vaccine will be administered at weekly intervals for 3 doses. This will be followed by a four week break and then a fourth vaccination. There will then be an eight week break and then a fifth vaccination, followed by additional immunizations every twelve weeks for 24 months total (as long as patient remains on study).

| IMMUNIZATION SCHEDULE | | | | | |
|---|---|---|---|---|---|
| | WEEK # | | | | |
| | 1 | 2 | 3 | 7 | 15 |
| VACCINE # | 1 | 2 | 3 | 4 | 5 |

5.3 Dose Administration and Modification 5.3.1 No dose escalation or dose modification will be performed. Systemic toxicity has not been seen with the previous vaccine studies. Systemic toxicity>grade II (with the exception of fever without infection) thought related to vaccination would result in removal of the patient from study and suspension of the protocol pending investigation.

5.3.2 The preparation will be administered subcutaneously to a site in the shoulders, buttocks, or thighs. It will be administered in one syringe, and will be supplied in approximately 1 cc total volume.

6.0 Evaluation During Study 6.1 Immune Function (Summarized in Table)

6.1.1 Antibody response: Peripheral blood (20-30 ml) will be drawn according to the schedule in table 8.3 with the exception of week 0, 7, and 9 at which time 50-60 ml will be collected for antibody testing. Thereafter, blood will be drawn at 12-week intervals as the patients return for booster immunizations. Antibodies against various antigens will be studies by ELISA, and against human tumor cell lines by FACS when appropriate.

6.2 Clinical and Laboratory Assessment:

6.2.1 Clinical and laboratory assessment schedule: The clinical and laboratory assessment schedule is outlined in Section 8.3 and includes parameters to assess the safety of the vaccine, as well as evaluate for signs of disease recurrence and progression. Abnormal findings will be evaluated per standard medical practice, and the abnormality will be classified as related to treatment, disease progression, or neither.

6.2.3 Extent of disease evaluation: All patients are by definition without clinical or radiographic evidence of disease at protocol entry.

6.2.4 Radiographic imaging (CT abdomen and pelvis) will be obtained q 6 months while on study, or if any clinical symptoms/examination findings warrant further evaluation, or if serum CA-125 rises to >70 (per time to treatment failure criteria), confirmed by repeat value; or at any time at the discretion of the investigator.

6.2.5 Length of follow-up: The primary endpoint of the study in this pilot trial is safety. Patients will be followed for the duration of the study, but based on previous trials, antibodies are generally present by the seventh week, and we will proceed with the proposal for additional studies to evaluate efficacy if no systemic toxicity is seen in any patient at the ninth week assessment. An additional 8-12 weeks would be required for processing before patients could be enrolled on the polyvalent study, allowing ample time for follow-up of the pilot trial. Patients will be followed until time to treatment failure, or until all vaccinations are completed (maximum 24 months).

6.3 Summary of Evaluation:

SUMMARY OF CLINICAL, LABORATORY, AND IMMUNE ASSESSMENTS

| | week # | | | | | | | | | | |
|---|---|---|---|---|---|---|---|---|---|---|---|
| | $0^a$ | 1 | 2 | 3 | 5 | 7 | 9 | 13 | 15 | 17 | $27^c$ |
| vaccine # | | 1 | 2 | 3 | | 4 | | | 5 | | V |
| Office Visit | * | * | * | * | * | * | * | * | * | * | * |
| Hx and PE | * | | * | * | | * | * | * | * | * | * |
| CA-125 | * | | | * | | * | * | * | | | * |
| CBC, diff | * | | * | * | * | * | * | * | * | | * |
| Hepatic profile + creatinine | * | | * | * | * | * | * | * | * | | * |
| Amylase | * | | * | * | * | * | * | * | * | | * |
| Urinalysis | * | | | * | | * | | * | | | * |
| PT | * | | | | | | | | | | |
| Stool guaiac$^b$ | * | | | | | * | | * | | | * |
| TSH | * | | | | | | | * | | | |
| Immune$^d$ bloods | | * | | | | * | * | * | * | * | * |

$^a$ = pretreatment evaluation, within 3 weeks
$^b$ = stool guaiac may be obtained by digital exam or cards collected by patient
$^c$ = following week 27, visits + laboratory studies + immunization q 3 months, CT scan q 6 months while on study
$^d$ = immune bloods routinely consist of 20-30 ml collected in 3 red top tubes. In order to obtain sufficient serum to evaluate for multiple antibodies, 6 tubes will be collected instead of 3 at the pre-vaccination visit; and at week 7 and 9 only.

7.0 Biostatistical Considerations
Endpoints:

The primary endpoints of this pilot trial are safety and confirmation of immunogenicity in the polyvalent setting. No systemic toxicity has occurred with the administration of monovalent vaccines at the center. Toxicity is not expected with this preparation. Following this pilot, additional studies with efficacy as the endpoint will be proposed. This pilot trial would be suspended pending investigation for any systemic toxicity thought related to vaccine in any patient. The same criteria for immunogenicity will be used as that of the individual pilot trials: patients must have IgM titer$\geq$1:80, or a four fold increase in prevailing antibody titer if present at baseline. Nine patients will be accrued, and $\geq$5 of 9 patients should meet these criteria for three or more antigens in order to proceed with this construct in additional studies. In prior trials, antibodies are generally present by completion of the fourth vaccination, (week 7). If no systemic toxicity is seen by the week 9 assessment in these patients, we will proceed with proposals for phase II studies with efficacy endpoints.

While not the endpoint of this pilot, patients would be removed from study for relapse as defined below. Time to treatment failure will be simply defined based on data from Rustin et al.[42] Treatment failure can be characterized by 1) physical examination evidence of disease recurrence, radiographic evidence of disease recurrence (biopsy will be performed at the discretion of the principal investigator but is not required); or 3) CA-125 elevation to twice the upper limits of normal (ie. $\geq$70), confirmed by a second sample also $\geq$70 U/ml. Time to treatment failure for biochemical relapse is recorded as the date of the first sample $\geq$70 U/ml.

The secondary endpoint of this pilot trial is to characterize the nature and duration of the immune response. Peripheral blood (20-30 ml) will be drawn as indicated in the table. Antibodies against the individual antigens will be studies by ELISA, and against the appropriate human tumor antigen FACS using human tumor cell lines expressing the respective antigen.

REFERENCES

1. McGuire W P, Hoskins W J., Brady M F, et al: Cyclophosphamide and cisplatin compared with paclitaxel and cisplatin in patients with stage III and stage IV ovarian cancer. New England Journal of Medicine 334:1-6, 1996
2. Barnhill D R, Hoskins W J, Heller P B, et al: The second look surgical reassessment for epithelial ovarian cancer. Gynecologic Oncology 19:148-, 1984
3. Cain J M, Saigo P E, Pierce V R, et al: A review of second look laparotomy for ovarian cancer. Gynecologic Oncology 23:14-, 1986
4. Rubin S C, W. J. H, Saigo P E, et al: Recurrence following negative second look laparotomy for ovarian cancer. American Journal of Obstetrics and Gynecology 159:1094-, 1988
5. Livingston P O, Zhang S, Lloyd K O: Carbohydrate vaccines that induce antibodies against cancer. Part I. Rational. Immunol Immunother 45:1-9, 1997
6. Jones P C, Sze L L, Liu P Y, et al: Prolonged survival for melanoma patients with elevated IgM antibody to oncofetal antigen. Journal of the National Cancer Institute 66:249-54, 1981
7. Zhang H, Zhang S, Cheung N K, et al: Antibodies can eradicate cancer micrometastasis. Cancer Research 58:2844-99, 1998
8. Livingston P O, Wong G Y C, Alduri S, et al: Improved survival in AJCC stage III melanoma patients with GM2 antibodies: a randomized trial of vaccination with GM2 ganglioside. Journal of Clinical Oncology 12:1036-44, 1994
9. Reithmuller G, Schneider-Gadicke E, Schlimok G, et al: Randomized trial of monoclonal antibody for adjuvant therapy of resected Dukes C colorectal carcinoma. Lancet 343:1177-1183, 1994
10. Livingston PO: The cases for melanoma vaccines that induce antibodies., in Kirkwood J M (ed): Molecular Diagnosis Prevention and Treatment of Melanoma, Marcel Dekker, Inc., 1997

11. Zhang S, Helling F, Lloyd KO, et al: Increased tumor cell reactivity and complement dependent cytotoxicity with mixtures of monoclonal antibodies against different gangliosides. Cancer Immunology and Immunotherapy 40:88-94, 1995

12. Feizi T: Demonstration by monoclonal antibodies that carbohydrate structures of glycoproteins and glycolipids are onco-developmental antigens. Nature 314:53-57, 1985

13. Fung P Y S, Madej M, Kaganty R R, et al: Active specific immunotherapy of a murine mammary adenocarcinoma using a synthetic tumor associated glycoconjugate. Cancer Research 50:4308-4314, 1990

14. Singhal A, Fohn M, Hakomori S I: Induction of a-N-acetylgalactosamine-O-serine/threonine(Tn) antigen-mediated cellular immune response for active immunotherapy in mice. Cancer Research 51:1406-1411, 1991

15. Zhao X J, Cheung N K: GD2 Oligosaccharide: target for cytotoxic T lymphocytes. Journal of Experimental Medicine 182:67-74, 1995

16. Livingston P O: Augmenting the immunogenicity of carbohydrate antigens. Seminars in Cancer Biology 6:357-366, 1995

17. Ghossein R, Scher H, Gerald W, et al: Detection of circulating tumor cells in patients with localized and metastatic prostate cancer. Journal of Clinical Oncology 13:1195-1200, 1995

18. Livingston P O, Natoli J, Jones Calves M, et al: Vaccines containing purified GM2 ganglioside elicit GM2 antibodies in melanoma patients. Proceedings of the Natl Acad Sci USA 84:2911-2915, 1987

19. MacLean G D, Bowen-Yachyn M B, Samuel J, et al: Active immunization of human ovarian cancer patients against a common carcinoma (Thomsen-Friedenreich) determinant using a synthetic carbohydrate antigen. Journal of Immunotherapy 11:292-305, 1992

20. Adluri S, Helling F, Calves M J, et al: Immunogenicity of synthetic TF and sTn-KLH conjugate in colorectal carcinoma patients. Cancer Immunology and Immunotherapy 41:185-192, 1995

21. Nakada H, Inoue M, Numata Y, et al: Epitopic structure of Tn glycophorin A for an anti-Tn antibody (MLS128). Proceedings of the Natl Acad Sci USA 90:2495-2499, 1993

22. Zhang S, Walberg L A, Ogata S, et al: Immune sera and monoclonal antibodies define two configurations for the sialyl Tn tumor antigen. Cancer Research 55:3364-3368, 1995

23. Bilodeau M T, Park T K, Hu S T, J. T./, et al: Total synthesis of a human breast tumor associated antigen. Journal of the American Chemical Society 117:7840-7841, 1995

24. Ragupathi G, Slovin S, Adluri S, et al: A fully synthetic globo-H carbohydrate vaccine induces a focused humoral response in prostate cancer patients: a proof of principle. Angewandte Chemie 38:563-566, 1999

25. Kudryashov V, Kim H M, Ragupathi G, et al: Immunogenicity of synthetic conjugates of Lewis-Y oligosaccharide with protein in mice: towards the design of anticancer vaccines. Cancer Immunology and Immunotherapy 45:281, 1998

26. Slovin S F, Ragupathi G, Adluri S, et al: Immunogenicity of a fully synthetic globo-H hexasaccharide conjugate in man. Proc Natl Acad Sci USA 96:5710-5715, 1999

27. Sabbatini P, Kudryashov V, Ragupathi G, et al: Immunization of ovarian cancer patients with a synthetic Lewis-Y protein conjugate vaccine: a phase I trial. Intl J Cancer 87 (1): 79-85, 2000.

28. Zhang S, Walberg L A, Helling F, et al: Augmenting the immunogenicity of synthetic MUC-1 vaccines in mice. Cancer Research 55:3364-3368, 1996

29. Gilewski T, Adluri S, Zhang S, et al: Vaccination of high-risk breast cancer patients with Mucin-1 keyhole limpet hemocyanin conjugate plus QS-21. Clinical Cancer Research 6(5):1693-701, 2000.

30. Adluri S, Gilewski T, Zhang S, et al: Specificity analysis of sera from breast cancer patients vaccinated with Muc-1-KLH plus QS-21. British Journal of Cancer 79:1806-1812, 1999

31. Ragupathi G, Park T K, Zhang S, et al: Immunization of mice with the synthetic hexasaccharide Globo H results in antibodies against human cancer cells. Angewandte Chem Int Engl: 125-128, 1997

32. Livingston PO: Approaches to augmenting the immunogenicity of melanoma gangliosides: from whole melanoma cells to ganglioside-KLH conjugate vaccines. Immunological Reviews 145:147-166, 1995

33. Chapman P B, Morissey D M, Pangeas K S, et al: Induction of antibodies against GM2 ganglioside by immunizing melanoma patients using GM2-KLH+QS21 vaccine: a dose response study. Clinical Cancer Research in press, 1999

34. Helling F, Shang Y, Calves M, et al: Increased immunogenicity of GD3 conjugate vaccines: comparison of various carrier proteins and selection of GD3-KLH for further testing. Cancer Research:197-203, 1994

35. Kensil C R, Patel U, Lennick M: Separation and characterization of saponins with adjuvant activity from Quillaja saponin Molina cortex. Journal of Immunology 146:431-436, 1991

36. Kim S K, Ragupathi G, Musselli C, et al: Comparison of the effect of different immunological adjuvants on the antibody and T-cell response to immunization with MUC1-KLH and GD3-KLH conjugate carrier vaccines. Vaccine 18:597-603, 2000

37. Marciani D J, Kensil C R, Beltz G A: Genetically engineered subunit vaccine against FeLV: protective immune response in cats. Vaccine 9:89-96, 1991

38. Livingston P O, Adluri S, Helling F, et al: Phase I trial of immunological adjuvant QS-21 with a GM2 ganglioside-keyhole limpet hemocyanin conjugate vaccine in patients with malignant melanoma. Vaccine 12:1275-1280, 1994

39. Zhang S, Zhang H, Cordon-Cardo C, Reuter V, et al. Selection of tumor antigens as targets for immune attack using immunohistochemistry: II. Blood Group-Related Antigens. Int J Cancer 73: 50-56, 1997.

40. Zheng S, Cordon-Cardo C, Zhang H, Reuter V, et al. Selection of tumor antigens as targets for immune attack using immunohistochemistry: I. Focus on gangliosides. Int J Cancer 73: 42-49, 1997.

41. Zheng S, Zhang H H H S, Cordon-Cardo C, Ragupathi G, et al. Selection of tumor antigens for immune attack using immunohistochemistry: Protein antigens. Clin Cancer Res 4: 2669-2676, 1998.

42. Rustin G J, Nelstrop A E, Bentzen S M, et al: Use of tumour markers in monitoring the course of ovarian cancer. Ann Oncol 10:21-7, 1999

Example 2

Heptavalent Vaccine Immunogenicity Trial in Mice

Methods
Serological Analyses
1. Elisa (Enzyme-Linked Immunosorbent Assay):

ELISA assays were performed as described below. Antigen in ethanol or in 0.1 M carbonate buffer (pH 11) were coated on ELISA plates at 0.2 μg/well for glycolipids and 0.1 μg/well for peptides. Serially diluted antiserum was added to each well and alkaline phosphatase-conjugated goat anti-mouse IgM or anti-mouse IgG was added at a dilution of 1:200 (Southern Biotechnology Associates, Inc, Birmingham, Ala.). Goat anti-mouse IgG and IgM conjugated with alkaline phosphatase obtained from Kierkegaard and Perry Labs, (Gaithersburg, Md.) were used as second antibodies. ELISA titer is defined as the highest dilution yielding an absorbance of 0.1 or greater over that of normal control mouse sera.

2. Cell Surface Reactivity Determined by FACS:

The cell surface reactivity of immune sera was tested on human MCF-7 and LSC cell lines. Single cell suspensions of $2 \times 10^5$ cells/tube were washed in PBS with 3% fetal calf serum (FCS) and 0.01M $NaN_3$ and incubated with 20 μl of 1:20 diluted sera or monoclonal antibody mAb for 30 min on ice. After two washes with 3% FCS in PBS, 20 μl of 1:15 diluted goat anti-mouse IgM or IgG-labeled with fluorescein-isothiocyanate (FITC, Southern Biotechnology Associates Inc. Birmingham, Ala.) was added, and the mixture incubated for 30 min. After a final wash, the positive population and mean fluorescence intensity of stained cells were differentiated using FACScan, Becton & Dickinson Immunocytometry, San Jose, Calif.

| | Immunizaton of mice with Heptavalent-KLH Conjugates plus ELISA | | | |
|---|---|---|---|---|
| ELISA plate coated with . . . | mice Immunized with . . . / (Group#) | pre vacc. (IgG/IgM) | GPI100 Or QS21. Mar. 19, 2001 post vacc. (IgG/IgM) | Comments |
| GM2 | GM2 (group #1) | 0/0 | 0/0 | |
| | GloboH (group#2) | | 0/0 | |
| | LeY (group #3) | | 0/0 | |
| | Muc1-G5 (group #4) | | 0/0 | |
| | STn(c) (group #5) | | 0/0 | |
| | TF(c) (group #6) | | 0/0 | |
| | Tn(c) (group #7) | | 0/0 | |
| Globo H | GM2 (group #1) | | | |
| | GloboH (group#2) | 0/0 | 640/5120 | |
| | LeY (group #3) | | | |
| | Muc1-G5 (group #4) | | | |
| | STn(c) (group #5) | | | |
| | TF(c) (group #6) | | | |
| | Tn(c) (group #7) | | | |
| LeY | GM2 (group #1) | | 0/0 | |
| | GloboH (group#2) | | 0/0 | |
| | LeY (group #3) | 0/0 | 640/2560 | |
| | Muc1-G5 (group #4) | | 0/0 | |
| | STn(c) (group #5) | | 0/160 | |
| | TF(c) (group #6) | | 0/40 | |
| | Tn(c) (group #7) | | 0/40 | |
| Muc1-G5 | GM2 (group #1) | | 0/320 | |
| | GloboH (group#2) | | 0/160 | |
| | LeY (group #3) | | 0/160 | |
| | Muc1-G5 (group #4) | 0/0 | 2560+/1280 | |
| | STn(c) (group #5) | | 40/80 | |
| | TF(c) (group #6) | | 40/80 | |
| | Tn(c) (group #7) | | 0/320 | |
| | mAb. C595 | | 2560/ | |
| | B55 | | /<5120+++ | |
| STn(c) | GM2 (group #1) | | 0/0 | |
| | GloboH (group#2) | | 0/0 | |
| | LeY (group #3) | | 0/0 | |
| | Muc1-G5 (group #4) | | 0/0 | |
| | STn(c) (group #5) | 0/0 | 5120/320 | |
| | TF(c) (group #6) | | 0/0 | |
| | Tn(c) (group #7) | | 0/0 | |
| | mAb. cc49 | | 1280/0 | |
| Tf(c) | GM2 (group #1) | | 0/40 | |
| | GloboH (group#2) | | 40/80 | |
| | LeY (group #3) | | 40/40 | |
| | Muc1-G5 (group #4) | | 5120+/160 | |
| | STn(c) (group #5) | | 5120+/320 | |
| | TF(c) (group #6) | 0/0 | 5120+/320 | |
| | Tn(c) (group #7) | | 5120+/640 | |
| | mAb. JAA-F11 | | 0/ | |
| | A78-6/A7 | | /640 | |

-continued

| | Immunizaton of mice with Heptavalent-KLH Conjugates plus ELISA | | | |
|---|---|---|---|---|
| | | | | GPI100 Or QS21. Mar. 19, 2001 |
| ELISA plate coated with ... | mice Immunized with .../ (Group#) | pre vacc. (IgG/IgM) | post vacc. (IgG/IgM) | Comments |
| Tn(c) | GM2 (group #1) | | 0/0 | |
| | GloboH (group#2) | | 0/0 | |
| | LeY (group #3) | | 0/0 | |
| | Muc1-G5 (group #4) | | 5120+/160 | |
| | STn(c) (group #5) | | 5120+/320 | |
| | TF(c) (group #6) | | 5120+/320 | |
| | Tn(c) (group #7) | 0/0 | 5120+/2580 | |
| | mAb. 5F4 | | /5120++ | |
| | HB-Tn1 | | /5120 | |

| | Immunization of mice with Heptavalent-KLH Conjugates* plus GPI-100 or QS-21. | | | | | | |
|---|---|---|---|---|---|---|---|
| | | | ELISA (IgG/IgM) | | FACS (IgG/IgM) | | |
| Group # | Antigen | Mice # | Pre-vacc. | Post-vacc | Pre-vacc. | Post-vacc. | Comments |
| 8. Heptavalent-KLH + 100 ug GPI-100 (200ul/mouse) | Tn(c) | 1 | 0/0 | 5120+/160 | | | |
| | | 2 | 0/0 | 5120/160 | | | |
| | | 3 | 0/0 | 5120/160 | | | |
| | | 4 | 0/0 | 5120++/640 | | | |
| | | 5 | 0/40 | 5120+/320 | | | |
| | Tf(c) | 1 | 0/0 | 5120/160 | | | |
| | | 2 | 0/0 | 5120/160 | | | |
| | | 3 | 0/0 | 5120/160 | | | |
| | | 4 | 0/0 | 5120+/320 | | | |
| | | 5 | 0/40 | 5120+/640 | | | |
| | sTN(c) | 1 | 0/0 | 5120/640 | | | |
| | | 2 | 0/0 | 1280/640 | | | |
| | | 3 | 0/0 | 5120/640 | | | |
| | | 4 | 0/0 | 5120/320 | | | |
| | | 5 | 0/0 | 1280/320 | | | |
| | MUC1-1G5 | 1 | 0/0 | 5120+/0 | | | |
| | | 2 | 0/0 | 5120+/80 | | | |
| | | 3 | 0/0 | 5120+++/160 | | | |
| | | 4 | 0/0 | 5120++/40 | | | |
| | | 5 | 0/0 | 5120+++/80 | | | |
| | Ley | 1 | 0/0 | 0/40 | | | |
| | | 2 | 0/0 | 320/640 | | | |
| | | 3 | 0/0 | 0/160 | | | |
| | | 4 | 0/0 | 80/40 | | | |
| | | 5 | 0/0 | 0/640 | | | |
| | Globo H | 1 | 0/80 | 40/640 | | | |
| | | 2 | 0/80 | 0/640 | | | |
| | | 3 | 0/80 | 0/640 | | | |
| | | 4 | 0/160 | 40/1280 | | | |
| | | 5 | 0/160 | 0/2560 | | | |
| | GM2 | 1 | 0/0 | 0/40 | | | |
| | | 2 | 0/0 | 0/0 | | | |
| | | 3 | 0/0 | 0/0 | | | |
| | | 4 | 0/0 | 0/0 | | | |
| | | 5 | 0/0 | 0/0 | | | |

Heptavalent: Tn(c) (3 ug), TF(c) (3 ug), sTn(c) (3 ug), MUC1-1G5 (3 ug), Ley (10 ug), Globo H (10 ug), and GM2 (10ug).
New GPI-100 used for all groups except group 9 (batch J).
Polysorbate 80, 4 mg/ml in final vaccine.

| | | | ELISA (IgG/IgM) | | FACS (IgG/IgM) | | |
|---|---|---|---|---|---|---|---|
| Group # | Antigen | Mice # | Pre-vacc. | Post-vacc | Pre-vacc. | Post-vacc. | Comments |

Immunization of mice with Heptavalent-KLH Conjugates* plus GPI-100 or QS-21.

| Group # | Antigen | Mice # | Pre-vacc. | Post-vacc | Pre-vacc. | Post-vacc. | Comments |
|---|---|---|---|---|---|---|---|
| | | | | | | | Apr. 2, 2001 |
| 9. Heptavalent-KLH + 100ug GPI-100 (Batch J) (200 ul/mouse) | Tn(c) | 1 | 0/0 | 640/40 | | | |
| | | 2 | 0/0 | 640/0 | | | |
| | | 3 | 0/0 | 5120/40 | | | |
| | | 4 | 0/0 | 5120+/0 | | | |
| | | 5 | 0/0 | 1280/40 | | | |
| | Tf(c) | 1 | 0/0 | 1280/80 | | | |
| | | 2 | 0/0 | 1280/40 | | | |
| | | 3 | 0/0 | 5120+/40 | | | |
| | | 4 | 0/0 | 5120++/40 | | | |
| | | 5 | 0/0 | 2560/40 | | | |
| | sTN(c) | 1 | 0/0 | 320/80 | | | |
| | | 2 | 0/0 | 320/160 | | | |
| | | 3 | 0/0 | 640/160 | | | |
| | | 4 | 0/0 | 640/80 | | | |
| | | 5 | 0/0 | 80/320 | | | |
| | MUC1-1G5 | 1 | 0/0 | 2560/0 | | | |
| | | 2 | 0/0 | 640/0 | | | |
| | | 3 | 0/0 | 640/0 | | | |
| | | 4 | 0/0 | 640/0 | | | |
| | | 5 | 0/0 | 2560/80 | | | |
| | Ley | 1 | 0/0 | 0/0 | | | |
| | | 2 | 0/0 | 0/80 | | | |
| | | 3 | 0/0 | 0/0 | | | |
| | | 4 | 0/0 | 0/0 | | | |
| | | 5 | 0/0 | 160/1280 | | | |
| | Globo H | 1 | 0/80 | 0/160 | | | |
| | | 2 | 0/80 | 0/320 | | | |
| | | 3 | 0/80 | 0/160 | | | |
| | | 4 | 0/80 | 0/320 | | | |
| | | 5 | 0/80 | 40/320 | | | |
| | GM2 | 1 | 0/0 | 0/0 | | | |
| | | 2 | 0/0 | 0/0 | | | |
| | | 3 | 0/0 | 0/0 | | | |
| | | 4 | 0/0 | 0/0 | | | |
| | | 5 | 0/0 | 0/0 | | | |
| 10. Heptavalent-KLH + 100 ug GPI-100 + polysorbate 80 (200 ul/mouse) | Tn(c) | 1 | 0/0 | 5120++/320 | | | |
| | | 2 | 0/0 | 5120/320 | | | |
| | | 3 | 0/40 | 5120+/1280 | | | |
| | | 4 | 0/0 | 5120+/640 | | | |
| | | 5 | 0/0 | 2560/320 | | | |
| | Tf(c) | 1 | 0/0 | 5120+/320 | | | |
| | | 2 | 0/0 | 5120+/160 | | | |
| | | 3 | 0/0 | 5120+/640 | | | |
| | | 4 | 0/0 | 5120+/640 | | | |
| | | 5 | 0/0 | 5120+/320 | | | |
| | sTN(c) | 1 | 0/0 | 320/640 | | | |
| | | 2 | 0/0 | 320/1280 | | | |
| | | 3 | 0/0 | 1280/1280 | | | |
| | | 4 | 0/0 | 640/40 | | | |
| | | 5 | 0/0 | 320/320 | | | |
| | MUC1-1G5 | 1 | 0/0 | 1280/40 | | | |
| | | 2 | 0/0 | 5120/80 | | | |
| | | 3 | 0/0 | 5120/160 | | | |
| | | 4 | 0/0 | 2560/160 | | | |
| | | 5 | 0/0 | 5120/40 | | | |
| | Ley | 1 | 0/0 | 0//0 | | | |
| | | 2 | 0/0 | 0/0 | | | |
| | | 3 | 0/0 | 0/640 | | | |
| | | 4 | 0/0 | 0/640 | | | |
| | | 5 | 0/0 | 0/80 | | | |
| | Globo H | 1 | 0/40 | 80/640 | | | |
| | | 2 | 0/80 | 40/2560 | | | |
| | | 3 | 0/320 | 0/2560 | | | |
| | | 4 | 0/160 | 0/2560 | | | |
| | | 5 | 0/80 | 0/640 | | | |
| | GM2 | 1 | 0/0 | 0/0 | | | |
| | | 2 | 0/0 | 0/0 | | | |
| | | 3 | 0/0 | 0/0 | | | |
| | | 4 | 0/0 | 0/0 | | | |
| | | 5 | 0/0 | 0/0 | | | |

-continued

| Immunization of mice with Heptavalent-KLH Conjugates* plus GPI-100 or QS-21. | | | | |
|---|---|---|---|---|
| 11. Heptavalent-KLH ++ 10 ug QS-21 (200 ul/mouse) | Tn(c) | 1 | 0/0 | 5120/160 |
| | | 2 | 0/0 | 5120+/160 |
| | | 3 | 0/40 | 5120+++/160 |
| | | 4 | 0/80 | 2560/320 |
| | | 5 | 0/0 | 5120+/80 |
| | Tf(c) | 1 | 0/40 | 5120+/320 |
| | | 2 | 0/0 | 5120++/640 |
| | | 3 | 0/160 | 5120++640 |
| | | 4 | 0/320 | 2560/640 |
| | | 5 | 0/40 | 5120++/320 |
| | sTN(c) | 1 | 0/0 | 40/40 |
| | | 2 | 0/0 | 2560/640 |
| | | 3 | 0/0 | 5120/160 |
| | | 4 | 0/0 | 1280/80 |
| | | 5 | 0/0 | 5120/640 |
| | MUC1-1G5 | 1 | 0/0 | 1280/160 |
| | | 2 | 0/0 | 2560/80 |
| | | 3 | 0/0 | 5120/80 |
| | | 4 | 0/0 | 2560/320 |
| | | 5 | 0/0 | 5120++/80 |
| | Ley | 1 | 0/0 | 0//0 |
| | | 2 | 0/0 | 0/0 |
| | | 3 | 0/0 | 0/0 |
| | | 4 | 0/0 | 0/0 |
| | | 5 | 0/0 | 40/40 |
| | Globo H | 1 | 0/80 | 40/320 |
| | | 2 | 0/80 | 80/320 |
| | | 3 | 0/80 | 40/640 |
| | | 4 | 40/160 | 0/640 |
| | | 5 | 0/320 | 0/2560 |
| | GM2 | 1 | 0/0 | 0/0 |
| | | 2 | 0/0 | 0/0 |
| | | 3 | 0/0 | 0/0 |
| | | 4 | 0/0 | 0/0 |
| | | 5 | 0/0 | 0/0 |
| 12. Heptavalent-KLH + 3 ug ER-803022 (200 ul/mouse) | Tn(c) | 1 | 0/40 | 2560/160 |
| | | 2 | 0/0 | 640/160 |
| | | 3 | 0/40 | 320/320 |
| | | 4 | 0/0 | 160/160 |
| | | 5 | 0/0 | 2560/160 |
| | Tf(c) | 1 | 0/0 | 2560/40 |
| | | 2 | 0/0 | 2560/40 |
| | | 3 | 0/0 | 640/160 |
| | | 4 | 0/0 | 320/80 |
| | | 5 | 0/0 | 2560/0 |
| | sTN(c) | 1 | 0/0 | 0/40 |
| | | 2 | 0/0 | 40/80 |
| | | 3 | 40/40 | 80/160 |
| | | 4 | 0/0 | 160/160 |
| | | 5 | 0/0 | 40/0 |
| | MUC1-1G5 | 1 | 0/0 | 80/0 |
| | | 2 | 0/0 | 80/0 |
| | | 3 | 0/0 | 80/40 |
| | | 4 | 0/0 | 40/80 |
| | | 5 | 0/0 | 40/0 |
| | Ley | 1 | 0/0 | 0/0 |
| | | 2 | 0/0 | 0/0 |
| | | 3 | 0/0 | 0/0 |
| | | 4 | 0/0 | 0/80 |
| | | 5 | 0/0 | 0/0 |
| | Globo H | 1 | 0/80 | 0/320 |
| | | 2 | 0/160 | 40/1280 |
| | | 3 | 0/320 | 0/320 |
| | | 4 | 80/160 | 160/1280 |
| | | 5 | 40/160 | 320/640 |
| | GM2 | 1 | 0/0 | 0/0 |
| | | 2 | 0/0 | 0/0 |
| | | 3 | 0/0 | 0/0 |
| | | 4 | 0/0 | 0/0 |
| | | 5 | 0/0 | 0/0 |

-continued

Immunization of mice with Heptavalent-KLH Conjugates* plus GPI-100 or QS-21.

| | | | | |
|---|---|---|---|---|
| 13. Heptavalent-KLH + 10 ug ER-803732 (200 ul/mouse) | Tn(c) | 1 | 0/40 | 40/320 |
| | | 2 | 0/0 | 40/40 |
| | | 3 | 0/0 | 320/160 |
| | | 4 | 0/40 | 160/160 |
| | | 5 | 0/40 | 160/80 |
| | Tf(c) | 1 | 0/0 | 160/160 |
| | | 2 | 0/0 | 320/40 |
| | | 3 | 0/40 | 640/160 |
| | | 4 | 0/40 | 320/160 |
| | | 5 | 0/0 | 320/160 |
| | sTN(c) | 1 | 0/0 | 40/80 |
| | | 2 | 0/0 | 0/80 |
| | | 3 | 0/0 | 0/320 |
| | | 4 | 0/160 | 40/320 |
| | | 5 | 0/40 | 40/160 |
| | MUC1-1G5 | 1 | 0/0 | 640/40 |
| | | 2 | 0/0 | 0/40 |
| | | 3 | 0/0 | 40/80 |
| | | 4 | 0/40 | 80/160 |
| | | 5 | 0/0 | 160/80 |
| | Ley | 1 | 0/0 | 0/0 |
| | | 2 | 0/0 | 0/0 |
| | | 3 | 0/40 | 40/320 |
| | | 4 | 0/0 | 0/40 |
| | | 5 | 0/0 | 0/80 |
| | Globo H | 1 | 40/80 | 80/160 |
| | | 2 | 0/160 | 40/320 |
| | | 3 | 0/40 | 80/320 |
| | | 4 | 0/80 | 0/160 |
| | | 5 | 80/160 | 160/320 |
| | GM2 | 1 | 0/0 | 0/0 |
| | | 2 | 0/0 | 0/0 |
| | | 3 | 0/0 | 0/0 |
| | | 4 | 0/0 | 0/0 |
| | | 5 | 0/0 | 0/0 |
| 14. 30 ug KLH + 100 ug GPI-100 (100 ul/mouse) | Tn(c) | 1 | 0/0 | 0/160 |
| | | 2 | 0/0 | 0/40 |
| | | 3 | 0/0 | 0/0 |
| | | 4 | 0/0 | 0/160 |
| | | 5 | 0/40 | 0/640 |
| | Tf(c) | 1 | 0/40 | 0/320 |
| | | 2 | 0/40 | 0/160 |
| | | 3 | 0/0 | 0/80 |
| | | 4 | 0/0 | 0/320 |
| | | 5 | 0/160 | 40/640 |
| | sTN(c) | 1 | 0/0 | 0/80 |
| | | 2 | 0/0 | 0/40 |
| | | 3 | 0/0 | 0/0 |
| | | 4 | 0/0 | 0/320 |
| | | 5 | 0/0 | 0/80 |
| | MUC1-1G5 | 1 | 40/40 | 0/160 |
| | | 2 | 0/40 | 0/80 |
| | | 3 | 0/0 | 0/80 |
| | | 4 | 0/0 | 0/320 |
| | | 5 | 0/0 | 0/320 |
| | Ley | 1 | 0/0 | 0/40 |
| | | 2 | 0/0 | 0/0 |
| | | 3 | 0/0 | 0/0 |
| | | 4 | 0/0 | 0/0 |
| | | 5 | 0/0 | 0/0 |
| | Globo H | 1 | 0/320 | 40/1280 |
| | | 2 | 0/320 | 0/640 |
| | | 3 | 0/80 | 0/1280 |
| | | 4 | 0/160 | 0/640 |
| | | 5 | 0/160 | 40/640 |
| | GM2 | 1 | 0/0 | 0/160 |
| | | 2 | 0/0 | 0/40 |
| | | 3 | 0/0 | 0/0 |
| | | 4 | 0/0 | 0/320 |
| | | 5 | 0/0 | 0/160 |
| | KLH | 1 | 0/0 | 5120++/320 |
| | | 2 | 0/40 | 5120++/160 |
| | | 3 | 0/0 | 5120++/320 |
| | | 4 | 0/0 | 5120++/640 |
| | | 5 | 0/40 | 5120++/320 |

-continued

Immunization of mice with Heptavalent-KLH Conjugates* plus GPI-100 or QS-21.

| FACS | | % positive cells | | | | | |
|---|---|---|---|---|---|---|---|
| Group # | | MCF-7 (IgG/IgM) | | | LSC (IgG/IgM) | | |
| (mice immunized with . . .) | Mice # | Pre-vacc. | Post-vacc. | 1:200 dilut. | Pre-vacc. | Post-vacc. | 1:200 dilut. |
| 1. 3 ug GM2-KLH + | 1 | 11.79/10.68 | 21.45/11.79 | 15.73/0.38 | 10.90/9.58 | 6.91/2.93 | 6.56/0.14 |
| 100 ug GPI-100 | 2 | 10.23/10.69 | 4.80/1.49 | 2.34/0.0 | 10.90/10.45 | 5.99/3.45 | 1.45/0.59 |
| (100 ul/mice) | 3 | 9.50/10.74 | 6.95/15.79 | 0.99/0.21 | 11.29/11.11 | 7.79/1.53 | 6.41/0.23 |
| | 4 | 9.81/9.68 | 3.41/12.63 | 0.99/2.06 | 9.76/11.06 | 6.94/1.75 | 3.42/0.02 |
| | 5 | 10.81/10.42 | 10.43/3.15 | 12.29/0.11 | 10.13/10.76 | 4.40/1.67 | 0.40/0.10 |
| 2. 3 ug GloboH-KLH + | 1 | 10.63/9.93 | 5.79/17.26 | 6.60/0.19 | 9.87/10.99 | 7.08/2.77 | 9.55/0.25 |
| 100 ug GPI100 | 2 | 10.08/10.67 | 16.60/27.63 | 10.54/6.75 | 10.0/10.41 | 8.9/3.43 | 1.29/0.52 |
| (100 ul/mice) | 3 | 11.03/10.09 | 27.21/40.86 | 27.58/2.30 | 10.42/10.61 | 11.56/1.15 | 7.60/0.02 |
| | 4 | 10.16/11.36 | 1.92/13.77 | 2.30/1.03 | 10.57/11.04 | 5.29/2.43 | 3.81/0.24 |
| | 5 | 11.94/10.82 | 24.61/12.97 | 20.32/3.62 | 10.79/10.72 | 10.58/2.54 | 1.25/0.20 |
| 3. 3 ug Ley-KLH + | 1 | 11.01/9.97 | 85.01/43.57 | 41.26/1.73 | 10.22/10.10 | 89.17/44.27 | 13.40/1.87 |
| 100 ug GPI-100 | 2 | 9.95/9.69 | 47.75/78.17 | 4.86/3.43 | 10.49/8.39 | 91.69/79.9 | 7.64/7.04 |
| (100 ul/mice) | 3 | 10.41/10.58 | 69.55/10.95 | 20.53/0.12 | 11.30/9.47 | 95.57/21.25 | 24.67/0.16 |
| | 4 | 11.93/10.03 | 91.08/0.76 | 21.29/0.0 | 10.96/9.60 | 81.5/6.24 | 9.08/0.38 |
| | 5 | 12.46/11.18 | 42.94/36.67 | 13.66/1.87 | 10.98/10.61 | 12.74/52.16 | 1.05/1.87 |
| 4. 3 ug Muc-1G-5-KLH + | 1 | 11.33/10.94 | 98.12/9.52 | 97.98/0.93 | 9.50/9.89 | 4.83/1.10 | 2.29/0.18 |
| 100 ug GPI-100 | 2 | 10.90/9.44 | 88.05/1.47 | 66.29/0.07 | 11.39/9.63 | 8.47/0.15 | 4.85/0 |
| (100 ul/mice) | 3 | 10.59/10.81 | 93.34/0.93 | 83.12/0.09 | 10.42/9.85 | 7.42/1.16 | 3.15/0.02 |
| | 4 | 10.47/9.70 | 94.57/21.92 | 85.52/0.47 | 9.70/11.11 | 10.99/7.79 | 3.47/0.71 |
| | 5 | 12.29/10.03 | 99.77/6.12 | 99.79/0.77 | *11.05/10.49 | 63.71/1.82 | 28.90/0.71 |
| 5. 3 ug STn(c)-KLH + | 1 | 9.56/9.77 | 13.95/1.74 | 1.29/0.13 | 10.10/10.73 | 95.14/4.42 | 86.94/0.50 |
| 100 ug GPI-100 | 2 | 9.91/10.59 | 15.95/1.79 | 12.70/0.23 | 10.20/11.18 | 98.65/19.42 | 88.58/0.59 |
| (100 ul/mice) | 3 | 10.72/10.55 | 6.88/2.81 | 6.23/0.02 | 11.31/11.48 | 97.78/31.98 | 95.31/0.36 |
| | 4 | 9.62/9.52 | 4.62/1.69 | 3.18/0.14 | 10.11/9.78 | 94.14/1.19 | 88.65/0.09 |
| | 5 | 10.77/10.71 | 17.96/2.16 | 7.17/0.3 | 10.71/0.05 | 97.66/7.28 | 87.09/0.38 |
| 6. 3 ug Tf(c)-KLH + | 1 | 10.84/10.39 | 13.89/5.73 | 5.86/0.23 | 9.64/10.31 | 7.66/4.74 | 3.85/0.24 |
| 100 ug GPI-100 | 2 | 9.22/11.34 | 31.03/4.44 | 31.75/0.10 | 9.65/10.15 | 9.01/1.17 | 3.98/0.18 |
| (100 ul/mice) | 3 | 10.59/10.11 | 4.05/1.05 | 0.73/0.02 | 10.12/9.92 | 4.97/2.77 | 0.90/0.04 |
| | 4 | 10.26/10.63 | 6.72/7.10 | 2.19/0.19 | 9.72/10.79 | 3.85/3.58 | 2.25/0.16 |
| | 5 | 12.0/10.90 | 9.11/6.28 | 5.18/0.18 | *11.54/10.09 | 11.71/5.0 | 12.76/0.64 |
| 7. 3 ug Tn(c)-KLH + | 1 | 9.60/10.44 | 3.64/8.41 | 0.62/0.37 | 10.65/10.46 | 9.91/5.07 | 3.02/0.32 |
| 100 ug GPI-100 | 2 | 10.54/10.46 | 12.94/3.24 | 20.35/0.17 | 11.50/10.85 | 4.81/0.48 | 5.33/0.05 |
| (100 ul/mice) | 3 | 10.51/10.46 | 4.72/23.22 | 0.16/1.22 | 10.70/9.68 | 2.37/1.33 | 0.04/0.02 |
| | 4 | 10.97/9.48 | 8.50/17.77 | 4.52/0.16 | 10.94/10.97 | 18.50/1.81 | 4.18/0.12 |
| | 5 | 10.79/10.72 | 46.27/32.77 | 9.46/2.04 | 11.40/10.16 | 25.42/16.84 | 16.5/22.80 |
| * DU145 | | +control | IE-3 | 91.67, 95.15 | +control | IE-3 | 95.73% |
| | | | MLS128 | 77.07% | | HMFG1 | 38.34% |
| | | | MLS132 | 19.92, 4.52 | | 49H8 | 84.90% |
| 8. Heptavalent-KLH + | 1 | 10.84/11.21 | 89.44/17.63 | 69.48/0.47 | 10.29/10.63 | 97.79/49.78 | 90.80/0.46 |
| 100 ug GPI-100 | 2 | 9.55/9.54 | 96.98/25.87 | 83.67/1.12 | 9.97/10.58 | 95.44/74.27 | 83.11/0.35 |
| (200 ul/mice) | 3 | 9.94/10.88 | 96.53/32.44 | 88.36/0.79 | 10.56/10.91 | 95.39/40.29 | 85.79/0.49 |
| | 4 | 10.90/10.72 | 99.47/5.72 | 96.61/0.45 | 10.69/10.42 | 97.65/16.44 | 88.77/0.28 |
| | 5 | 10.37/10.17 | 75.64/10.67 | 63.57/0.11 | 10.58/10.14 | 93.93/15.49 | 71.06/1.36 |
| 9. Heptavalent-KLH + | 1 | 10.65/10.57 | 74.25/12.81 | 69.56/1.07 | 10.93/10.21 | 99.45/8.83 | 85.59/0.38 |
| 100 ug GPI-100 | 2 | 10.20/10.97 | 98.22/16.51 | 81.61/0.91 | 10.86/10.78 | 96.70/22.94 | 66.20/0.50 |
| (batch J) | 3 | 9.96/9.68 | 89.36/1.03 | 60.88/0.22 | 9.79/9.80 | 95.10/0.43 | 53.45/0.03 |
| (200 ul/mice) | 4 | 10.77/10.75 | 82.25/8.95 | 27.80/0.09 | 10.58/10.28 | 92.21/1.17 | 65.13/0.18 |
| | 5 | 10.95/10.77 | 77.49/10.19 | 62.39/0.13 | | | |
| 10. Heptavalent-KLH + | 1 | 10.99/10.32 | 84.54/8.61 | 39.91/0.49 | 10.63/10.92 | 93.11/38.33 | 63.61/1.57 |
| 100 ug GPI-100 + | 2 | 10.09/10.92 | 97.83/11.79 | 94.21/0.16 | 10.72/10.68 | 97.64/12.52 | 77.95/0.05 |
| polysorbate 80 | 3 | 11.32/10.32 | 97.74/15.67 | 89.24/0.30 | 9.53/10.16 | 89.84/2.13 | 63.96/0.19 |
| (200 ul/mice) | 4 | 9.76/10.59 | 92.51/15.57 | 82.83/0.10 | 11.50/10.03 | 60.13/14.56 | 8.56/1.59 |
| | 5 | 10.33/10.05 | 80.12/11.34 | 70.98/0.30 | | | |
| 11. Heptavalent-KLH + | 1 | 10.96/10.08 | 91.06/1.64 | 55.98/0.02 | 9.76/10.81 | 26.58/2.13 | 5.42/0.16 |
| 10 ug QS-21 | 2 | 9.88/10.41 | 94.84/2.32 | 72.07/0.02 | 9.80/11.58 | 88.16/22.37 | 34.36/0.94 |
| (200 ul/mice) | 3 | 11.0/10.57 | 99.34/9.99 | 93.96/0.84 | 9.86/10.79 | 87.20/11.70 | 76.90/0.14 |
| | 4 | 11.05/10.65 | 88.58/3.78 | 61.69/0.13 | 10.07/10.45 | 71.56/3.79 | 26.42/0.15 |
| | 5 | 10.86/10.27 | 81.44/6.27 | 69.68/0.14 | | | |
| 12. Heptavalent-KLH + | 1 | 18.54/11.29 | 67.73/1.59 | 26.33/0.18 | 10.98/9.97 | 16.98/1.97 | 6.40/0.09 |
| 3 ug ER803022 | 2 | 9.69/9.60 | 74.76/0.72 | 33.45/0.08 | 10.62/10.33 | 36.76/2.05 | 3.73/0.07 |
| (200 ul/mice) | 3 | 9.65/10.62 | 91.62/2.89 | 46.96/0.31 | 10.16/10.03 | 28.33/4.88 | 3.26/0.10 |
| | 4 | 10.78/10.0 | 22.58/4.14 | 9.51/0.36 | | | |
| | 5 | 10.90/10.94 | 48.15/7.29 | 10.64/0.23 | | | |
| 13. Heptavalent-KLH + | 1 | 10.08/10.56 | 74.85/8.71 | 40.57/0.24 | 10.96/10.20 | 64.39/3.85 | 7.58/0.17 |
| 10 ug ER803732 | 2 | 11.03/10.91 | 36.35/5.07 | 4.79/0.07 | 9.84/10.19 | 3.67/11.73 | 0.47/0.73 |
| (200 ul/mice) | 3 | 10.22/10.54 | 65.94/30.22 | 7.87/0.63 | 10.83/10.07 | 66.06/25.19 | 8.66/0.82 |
| | 4 | 10.75/10.07 | 91.69/12.15 | 22.96/0.41 | | | |
| | 5 | 10.87/11.04 | 35.45/6.88 | 1.38/0.11 | | | |

| Immunization of mice with Heptavalent-KLH Conjugates* plus GPI-100 or QS-21. | | | | | | | |
|---|---|---|---|---|---|---|---|
| 14. 30 ug KLH + | 1 | 9.42/11.35 | 13.72/9.84 | 10.08/2.29 | 10.85/10.49 | 5.49/4.48 | 3.29/2.53 |
| 100 ug GPI-100 | 2 | 12.14/11.31 | 17.50/2.09 | 6.41/0.0 | 10.58/10.44 | 10.57/3.53 | 14.38/0.21 |
| (200 ul/mice) | 3 | 9.82/10.97 | 1.64/1.05 | 0.13/0.02 | 9.19/11.45 | 15.10/1.03 | 11.63/0.01 |
| | 4 | 11.20/11.84 | 13.25/2.14 | 10.05/0.12 | | | |
| | 5 | 10.51/9.95 | 8.98/5.40 | 1.38/0.06 | | | |

Heptavalent: Tn(c) (3 ug), TF(c) (3 ug), sTn(c) (3 ug), MUC1-1G5 (3 ug), Ley (10 ug), Globo H (10 ug), and GM2 (10 ug).
New GPI-100 used for all groups except group 9 (batch J).

Third Series of Experiments
Polyvalent Conjugate Vaccine for Cancer

Tumor-specific antigens have been identified and pursued as targets for vaccines. The inventors' previous work has shown that monovalent vaccines utilizing the tumor antigens Globo H, Lewisy, GM2, glycosylated MUC-1, Tn(c), sTn(c), or TF(c) conjugated to KLH to be safe with local erythema and edema but minimal systemic toxicities. As a result of vaccination with these monovalent vaccines, most patients generated specific high titer IgM or IgG antibodies against the respective antigen-KLH conjugates. The present invention provides multivalent vaccines wherein the components of the monovalent vaccine are combined and administered with an adjuvant as treatment for cancer.

Vaccines consisting of a combination of tumor antigens administered with a saponin immunological adjuvant QS-21 or GPI-0100. The antigens are glycosylated MUC-1-G5, Globo H, GM2, $Le^y$, Tn(c), sTn(c), and TF(c). In each case the antigen is conjugated to Keyhole Limpet Hemocyanin (KLH).

The preferred ranges of the antigen and adjuvant doses are as follows:
Glycosylated MUC-1-G5: 0.1 to 30 g;
Globo H: 0.1 to 100 g;
GM2: 0.1 to 100 g;
$Le^y$: 0.1 to 60 g;
Tn(c): 0.1 to 100 g;
sTn(c): 0.1 to 100 g;
TF(c): 0.1 to 30 g;
QS-21: 25-200 g;
GPI-0100: 1-25 mg.

Example 1

Comparison of the Immune Response after Immunization with Monovalent and Hexavalent-KLH Conjugate Vaccines Against Prostate Cancer The immune response of the five initial patients receiving hexavalent vaccine with the immune responses of patients who had previously been immunized with the respective monovalent vaccines is compared in the following five tables. Shown are the reciprocal mean peak ELISA titer for IgM and IgG after immunization and FACS assay (% of positive cells/mean intensity) using the MCF-7 tumor cell line. The comparison for GM2-KLH is pending. Comparing the responses induced by monovalent and hexavalent vaccines, there was no significant difference in the antibody responses against any of the five antigens tested to date. Combination of six individual conjugates into a single vaccine does not significantly change the antibody response against the individual antigens.

| Hexavalent Versus Monovalent: Prostate | | | | | |
|---|---|---|---|---|---|
| Aug. 6, 2001 | | | | | |
| | | Patient | Elisa (TF-HSA) | | MCF-7 FACS |
| Trial | Patient | Sera | IgM | IgG | IgM %/Mean |
| protocol 98-048 | M1 | week 1 | 10 | 10 | 10/37 |
| TF(c)-KLH + QS21 | | week 7 | 1280+ | 160 | 11/39 |
| dosage: 1 μg | | week 9 | 1280 | 40 | 17/50 |
| | M2 | week 1 | 10 | 0 | 10/21 |
| | | week 7 | 1280++ | 10 | 52/54 |
| | | week 9 | 1280+++ | 10 | 72/64 |
| | M3 | week 1 | 0 | 0 | 11/135 |
| | | week 7 | 1280++ | 160 | 2/28 |
| | | week 9 | 1280++ | 1280 | 6/104 |
| | M4 | week 1 | 0 | 0 | 10/32 |
| | | week 7 | 160 | 10 | 18/43 |
| | | week 9 | 160 | 160 | 26/47 |
| | M5 | week 1 | 0 | 0 | 10/36 |
| | | week 7 | 320 | 0 | 9/28 |
| | | week 9 | 320 | 0 | 8/22 |
| protocol 00-064 | H1 | week 1 | 20 | 0 | 11/64 |
| Hexavalent Conjgate + QS21 | | week 7 | 1280 | 160 | 7/55 |
| TF(c)dosage: 3 μg | | week 12 | 1280 | 160 | 3/31 |
| | H2 | week 1 | 40 | 10 | 9/37 |
| | | week 7 | 1280 | 160 | 21/50 |
| | | week 12 | 640 | 160 | 17/43 |
| | H3 | week 1 | 40 | 0 | 10/35 |
| | | week 7 | 1280 | 20 | 54/65 |
| | | week 12 | 640 | 40 | 34/47 |

| | | | | | |
|---|---|---|---|---|---|
| Hexavalent Versus Monovalent: Prostate | | | | | |
| | H4 | week 1 | 80 | 0 | 10/26 |
| | | week 7 | 1280 | 80 | 22/43 |
| | | week 12 | 1280 | 20 | 19/54 |
| | H5 | week 1 | 0 | 0 | 10/13 |
| | | week 7 | 1280 | 320 | 57/26 |
| | | week 12 | 1280 | 320 | 47/22 |
| Controls | C1 | Aug. 27, 1999 | 1280 | 1280 | |

Aug. 10, 2001

| Trial | Patient | Patient Sera | Elisa (Tn-HSA) IgM | IgG | MCF-7 FACS IgM %/Mean |
|---|---|---|---|---|---|
| protocol 98-002 | M1 | week 1 | 0 | 80 | 10/22 |
| Tn(c)-KLH + QS21 | | week 7 | 40 | 2560 | 7/18 |
| dosage: 3 μg | | week 9 | 80 | 2560 | 9/21 |
| | M2 | week 1 | 10 | 80 | 11/26 |
| | | week 7 | 320 | 5120 | 32/40 |
| | | week 9 | 640 | 5120 | 37/42 |
| | M3 | week 1 | 20 | 40 | 11/25 |
| | | week 7 | 640 | 640 | 12/26 |
| | | week 9 | 1280 | 1280 | 13/27 |
| | M4 | week 1 | 40 | 40 | 10/49 |
| | | week 7 | 640 | 1280 | 9/40 |
| | | week 9 | 1280 | 1280 | 8/39 |
| | M5 | week 1 | 10 | 80 | 11/25 |
| | | week 7 | 1280 | 5120 | 12/26 |
| | | week 9 | 1280 | 5120 | 13/27 |
| protocol 00-064 | H1 | week 1 | 80 | 0 | 11/64 |
| Hexavalent Conjgate + QS21 | | week 7 | 320 | 1280 | 7/55 |
| Tn dosage: 3 μg | | week 12 | 320 | 1280 | 3/31 |
| | H2 | week 1 | 320 | 10 | 9/37 |
| | | week 7 | 1280 | 320 | 21/50 |
| | | week 12 | 1280 | 320 | 17/43 |
| | H3 | week 1 | 10 | 0 | 10/35 |
| | | week 7 | 320 | 640 | 54/65 |
| | | week 12 | 640 | 640 | 34/47 |
| | H4 | week 1 | 40 | 160 | 10/26 |
| | | week 7 | 640 | 5120 | 22/43 |
| | | week 12 | 320 | 5120 | 19/54 |
| | H5 | week 1 | 0 | 20 | 10/13 |
| | | week 7 | 320 | 640 | 57/26 |
| | | week 12 | 320 | 640 | 47/22 |
| Controls | C2 | | 1280+ | 640 | |

Aug. 17, 2001

| Trial | Patient | Patient Sera | Elisa (GloboH) IgM | IgG | MCF-7 FACS IgM %/Mean |
|---|---|---|---|---|---|
| PROTOCOL 96-055 | M1 | week 1 | 0 | 0 | 11/40 |
| GloboH-KLH + QS21 | | week 7 | 20 | 0 | 9/30 |
| dosage: 10 μg | | week 9 | 20 | 0 | 9/40 |
| | M2 | week 1 | 0 | 0 | 11/33 |
| | | week 7 | 0 | 0 | 12/42 |
| | | week 9 | 0 | 0 | 14/52 |
| | M3 | week 1 | 20 | 0 | |
| | | week 7 | 640 | 0 | |
| | | week 9 | 640 | 0 | |
| | M4 | week 1 | 10 | 0 | 11/26 |
| | | week 7 | 160 | 0 | 19/39 |
| | | week 9 | 160 | 0 | 25/39 |
| | M5 | week 1 | 40 | 0 | 10/26 |
| | | week 7 | 160 | 0 | 17/38 |
| | | week 9 | off study | off study | |
| PROTOCOL 00-064 | H1 | week 1 | 40 | 0 | 11/41 |
| Hexavalent Conjgate + QS21 | | week 7 | 160 | 0 | 9/36 |
| GloboH dosage: 10 μg | | week 12 | 160 | 80 | 6/27 |
| | H2 | week 1 | 160 | 0 | 11/33 |
| | | week 7 | 640 | 0 | 11/36 |
| | | week 12 | 320 | 0 | 15/40 |
| | H3 | week 1 | 40 | 0 | 11/29 |
| | | week 7 | 20 | 0 | 56/59 |
| | | week 12 | 20 | 0 | 43/46 |
| | H4 | week 1 | 80 | 0 | 10/34 |
| | | week 7 | 160 | 0 | 21/46 |
| | | week 12 | 80 | 0 | 16/44 |

| | | | -continued | | |
|---|---|---|---|---|---|
| Hexavalent Versus Monovalent: Prostate | | | | | |
| | H5 | week 1 | 40 | 0 | 10/15 |
| | | week 7 | 80 | 0 | 64/35 |
| | | week 12 | 80 | 0 | 45/27 |
| Controls | C3 | week 26 | | 640 | |
| | C4 | | 1280 | | |

Aug. 31, 2001

| Trial | Patient | Patient Sera | Elisa Ley-Cer IgM | IgG | MCF-7 FACS IgM %/Mean |
|---|---|---|---|---|---|
| PROTOCOL 00-075 | M1 | week 1 | 0 | 0 | 11/23 |
| LewY-MMCCH-KLH | | week 7 | 0 | 0 | 13/26 |
| dosage: 20 µg | | week 9 | 0 | 0 | 24/92 |
| | M2 | week 1 | 0 | 0 | 10/25 |
| | | week 7 | 0 | 0 | 20/32 |
| | | week 9 | 0 | 0 | 14/24 |
| | M3 | week 1 | 0 | 0 | 11/30 |
| | | week 7 | 40 | 80 | 8/20 |
| | | week 9 | 20 | 40 | 14/41 |
| | M4 | week 1 | 0 | 0 | 11/46 |
| | | week 7 | 0 | 0 | 10/50 |
| | | week 9 | 0 | 10 | 9/44 |
| | M5 | week 1 | 0 | 0 | 10/50 |
| | | week 7 | 40 | 0 | 3/30 |
| | | week 9 | 0 | 10 | 18/63 |
| PROTOCOL 00-064 | H1 | week 1 | 0 | 0 | 11/41 |
| Hexavalent Conjgate + QS21 | | week 7 | 0 | 0 | 9/36 |
| Ley dosage: 10 µg | | week 12 | 0 | 0 | 6/27 |
| | H2 | week 1 | 0 | 0 | 11/33 |
| | | week 7 | 0 | 0 | 11/36 |
| | | week 12 | 0 | 0 | 15/40 |
| | H3 | week 1 | 0 | 0 | 11/29 |
| | | week 7 | 10 | 0 | 56/59 |
| | | week 12 | 0 | 0 | 43/46 |
| | H4 | week 1 | 0 | 10 | 10/34 |
| | | week 7 | 10 | 10 | 21/46 |
| | | week 12 | 10 | 0 | 16/44 |
| | H5 | week 1 | 0 | 0 | 10/15 |
| | | week 7 | 0 | 0 | 64/35 |
| | | week 12 | 0 | 0 | 45/27 |
| Controls | C5 | | 2560 | | |
| | C6 | | | 640 | |

Aug. 19, 2001

| Trial | Patient | Patient Sera | Elisa (MUC33G5) IgM | IgG | MCF-7 FACS IgM %/Mean |
|---|---|---|---|---|---|
| PROTOCOL 99-23 | M1 | week 1 | 0 | 0 | 10/25 |
| MUC33G 5 site-KLH + QS21 | | week 7 | 160 | 640 | 17/31 |
| dosage: 3 µg | | week 9 | 160 | 640 | 31/45 |
| | M2 | week 1 | 0 | 0 | 10/29 |
| | | week 7 | 2560 | 640 | 38/53 |
| | | week 9 | 2560 | 640 | 35/43 |
| | M3 | week 1 | 0 | 20 | 10/28 |
| | | week 7 | 2560 | 160 | 36/57 |
| | | week 9 | 2560 | 320 | 43/60 |
| | M4 | week 1 | 0 | 0 | 11/41 |
| | | week 7 | 2560 | 80 | 12/35 |
| | | week 9 | 640 | 320 | 12/38 |
| | M5 | week 1 | 0 | 0 | 11/30 |
| | | week 7 | 40 | 0 | 61/65 |
| | | week 9 | 40 | 80 | 59/67 |
| PROTOCOL 00-064 | H1 | week 1 | 0 | 0 | 11/41 |
| Hexavalent Conjgate + QS21 | | week 7 | 20 | 640 | 9/36 |
| MUC33 dosage: 3 µg | | week 12 | 0 | 160 | 6/27 |
| | H2 | week 1 | 0 | 0 | 11/33 |
| | | week 7 | 0 | 40 | 11/36 |
| | | week 12 | 0 | 80 | 15/40 |
| | H3 | week 1 | 0 | 0 | 11/29 |
| | | week 7 | 160 | 160 | 56/59 |
| | | week 12 | 40 | 320 | 43/46 |

-continued

| | | Hexavalent Versus Monovalent: Prostate | | | |
|---|---|---|---|---|---|
| | H4 | week 1 | 0 | 20 | 10/34 |
| | | week 7 | 40 | 320 | 21/46 |
| | | week 12 | 40 | 160 | 16/44 |
| | H5 | week 1 | 0 | 0 | 10/15 |
| | | week 7 | 40 | 160 | 64/35 |
| | | week 12 | 0 | 80 | 45/27 |
| Controls | C7 | | 2560 | 640 | |

Immunization of mice with Heptavalent-KLH
Conjugates* plus GPI-100 or QS-21
Mean Value:

Nov. 30, 2001

| Group # | Antigen | ELISA Pre IgG | ELISA Pre IgM | ELISA Post IgG | ELISA Post IgM | FACS MCF-7 Pre IgG | FACS MCF-7 Pre IgM | FACS MCF-7 Post IgG | FACS MCF-7 Post IgM | FACS MCF-7 1:200 IgG | FACS MCF-7 1:200 IgM | LSC Pre IgG | LSC Pre IgM | LSC #LSC Post IgG | LSC #LSC Post IgM | LSC 1:200 IgG | LSC 1:200 IgM | Mice # | CDC (MCF-7) Pre | CDC (MCF-7) Post |
|---|---|---|---|---|---|---|---|---|---|---|---|---|---|---|---|---|---|---|---|---|
| 1. 3 ug GM2-KLH + 100 ug GPI-100 (100 ul/mice) | Tn | | | | | | | 9.40% | 8.97% | 6.47% | 0.55% | 10.59% | 10.60% | 6.41% | 1.92% | 3.63% | 0.22% | | | |
| | Tf | | | | | 10.43% | 10.44% | | | | | | | | | | | | | |
| | sTn | | | | | | | | | | | | | | | | | | | |
| | Muc1-G5 | | | | | | | | | | | | | | | | | | | |
| | Ley | | | | | | | | | | | | | | | | | | | |
| | globo H | | | | | | | | | | | | | | | | | | | |
| | GM2 | 0 | 0 | 0 | 0 | | | | | | | | | | | | | | | |
| 2. 3 ug GloboH-KLH + 100 ug GPI100 (100 ul/mice) | Tn | | | | | 10.77% | 10.57% | 15.22% | 22.50% | 13.47% | 2.78% | 10.33% | 10.75% | 7.08% | 2.46% | 4.70% | 0.25% | | | |
| | Tf | | | | | 10.08% | 10.57% | 8.01% | 32.59% | 6.86% | 7.39% | | | | | | | | | |
| | sTn | | | | | (mice#1 re-tested.) | | | | | | | | | | | | | | |
| | Muc1-G5 | | | | | | | | | | | | | | | | | | | |
| | Ley | | | | | | | | | | | | | | | | | | | |
| | globo H | 0 | 0 | 640 | 5120 | | | | | | | | | | | | | | | |
| | GM2 | | | | | | | | | | | | | | | | | | | |
| 3. 3 ug Ley-KLH + 100 ug GPI-100 (100 ul/mice) | Tn | | | | | 11.15% | 10.34% | 67.27% | 34.02% | 20.32% | 1.43% | 10.79% | 9.63% | 74.13% | 40.76% | 11.12% | 2.26% | 3-1 | 5.94% | 46.42% |
| | Tf | | | | | | | | | | | | | | | | | 3-2 | 4.47% | 75.05% |
| | sTn | | | | | | | | | | | | | | | | | 3-3 | 4.49% | 9.21% |
| | Muc1-G5 | | | | | | | | | | | | | | | | | 3-4 | 22.5% | 119.0% |
| | Ley | 0 | 0 | 640 | 2560 | | | | | | | | | | | | | 3-5 | 11.02% | 61.7% |
| | globo H | | | | | | | | | | | | | | | | | | | |
| | GM2 | | | | | | | | | | | | | | | | | | | |
| 4. 3 ug Muc-1G-5-KLH + 100 ug GPI-100 (100 ul/mice) | Tn | | | | | 11.12% | 10.12% | 94.77% | 7.99% | 86.54% | 0.46% | 10.25% | 10.12% | 7.93% | 2.55% | 3.44% | 0.23% | 4-1 | 3.30% | |
| | Tf | | | | | | | | | | | | | | | | | 4-2 | 6.85% | |
| | sTn | | | | | | | | | | | | | | | | | 4-3 | 14.0% | |
| | Muc1-G5 | 0 | 0 | 2560+ | 1280 | | | | | | | | | | | | | 4-4 | 4.49% | |
| | Ley | | | | | | | | | | | | | | | | | 4-5 | 4.23% | |
| | globo H | | | | | | | | | | | | | | | | | | | |
| | GM2 | | | | | | | | | | | | | | | | | | | |
| 5. 3 ug STn(c)-KLH + 100 ug GPI-100 (100 ul/mice) | Tn | | | | | 10.12% | 10.23% | 11.88% | 2.04% | 6.11% | 0.16% | 10.49% | 8.64% | 96.67% | 12.86% | 88.91% | 0.38% | 5-1 | 6.83% | |
| | Tf | | | | | | | | | | | | | | | | | 5-2 | 10.91% | |
| | sTn | 0 | 0 | 5120 | 320 | | | | | | | | | | | | | 5-3 | 6.36% | |
| | Muc1-G5 | | | | | | | | | | | | | | | | | 5-4 | 7.11% | |
| | Ley | | | | | | | | | | | | | | | | | 5-5 | 4.37% | |
| | globo H | | | | | | | | | | | | | | | | | | | |
| | GM2 | | | | | | | | | | | | | | | | | | | |

-continued

Immunization of mice with Heptavalent-KLH
Conjugates* plus GPI-100 or QS-21
Mean Value:

Nov. 30, 2001

| Group # | Antigen | ELISA Pre IgG | ELISA Pre IgM | ELISA Post IgG | ELISA Post IgM | FACS MCF-7 Pre IgG | FACS MCF-7 Pre IgM | FACS MCF-7 Post IgG | FACS MCF-7 Post IgM | FACS MCF-7 1:200 IgG | FACS MCF-7 1:200 IgM | LSC #LSC Pre IgG | LSC #LSC Pre IgM | LSC Post IgG | LSC Post IgM | LSC 1:200 IgG | LSC 1:200 IgM | Mice # | CDC (MCF-7) Pre | CDC (MCF-7) Post |
|---|---|---|---|---|---|---|---|---|---|---|---|---|---|---|---|---|---|---|---|---|
| 6. 3 ug Tf(c)-KLH + 100 ug GPI-100 (100 ul/mice) | Tn | 0 | 0 | 5120 | 320 | 10.58% | 10.67% | 10.56% | 4.92% | 9.14% | 0.14% | 9.78% | 10.29% | 6.37% | 3.06% | 2.74% | 0.16% | | | |
| | Tf | | | | | | | | | | | | | | | | | | | |
| | sTn | | | | | | | | | | | | | | | | | | | |
| | Muc1-G5 | | | | | | | | | | | | | | | | | | | |
| | Ley | | | | | | | | | | | | | | | | | | | |
| | globo H | | | | | | | | | | | | | | | | | | | |
| | GM2 | | | | | | | | | | | | | | | | | | | |
| 7. 3 ug Tn(c)-KLH + 100 ug GPI-100 (100 ul/mice) | Tn | 0 | 0 | 5120+ | 2560 | 10.48% | 10.31% | 15.21% | 17.10% | 7.02% | 0.79% | 11.04% | 10.42% | 12.20% | 5.11% | 5.81% | 4.66% | | | |
| | Tf | | | | | | | | | | | | | | | | | | | |
| | sTn | | | | | | | | | | | | | | | | | | | |
| | Muc1-G5 | | | | | | | | | | | | | | | | | | | |
| | Ley | | | | | | | | | | | | | | | | | | | |
| | globo H | | | | | | | | | | | | | | | | | | | |
| | GM2 | | | | | | | | | | | | | | | | | | | |
| | KLH | | | | | | | | | | | | | | | | | | | |
| 8. Heptavalent-KLH + 100 ug GPI100 (200 ul/mice) | Tn | 0 | 10 | 5120+ | 320 | 10.32% | 10.5% | 91.61% | 18.46% | 80.34% | 0.59% | 10.43% | 10.54% | 96.04% | 39.25% | 83.91% | 0.59% | 8-1 | 0.75% | 2.99% |
| | Tf | 0 | 10 | 5120 | 320 | 10.63% | 10.14% | 98.92% | 24.41% | 85.27% | 7.44% | | | | | | | 8-2 | 1.0% | 12.63% |
| | sTn | 0 | 0 | 2560 | 640 | (mice #1 re-tested) | | | | | | | | | | | | 8-3 | -2.23% | 44.48% |
| | Muc1-G5 | 0 | 0 | 5120++ | 80 | | | | | | | | | | | | | 8-4 | -3.12% | 24.77% |
| | Ley | 0 | 0 | 80 | 160 | | | | | | | | | | | | | 8-5 | 7.65% | 27.28% |
| | globo H | 0 | 80 | 10 | 1280 | | | | | | | | | | | | | VK9 | | 2.05% |
| | GM2 | 0 | 0 | 0 | 10 | | | | | | | | | | | | | 3S193 | | 82.2% |
| | | | | | | | | | | | | | | | | | | anti-GM2 | | 71.2% |
| | | | | | | | | | | | | | | | | | | 696 | | 32.2% |
| 9. Heptavalent-KLH + 100 ug GPI (old batch) (200 ul/mice) | Tn | 0 | 0 | 2560 | 40 | 10.51% | 10.55% | 84.31% | 9.89% | 60.45% | 0.48% | 10.40% | 10.21% | 92.22% | 16.68% | 63.24% | 0.25% | 9-1 | -2.79% | 34.02% |
| | Tf | 0 | 0 | 5120 | 40 | | | | | | | | | | | | | 9-2 | 2.96% | 9.42% |
| | sTn | 0 | 0 | 320 | 160 | | | | | | | | | | | | | 9-3 | 4.50% | 11.41% |
| | Muc1-G5 | 0 | 0 | 1280 | 0 | | | | | | | | | | | | | 9-4 | 6.74% | 9.51% |
| | Ley | 0 | 0 | 40 | 320 | | | | | | | | | | | | | 9-5 | 4.01% | 39.91% |
| | globo H | 0 | 80 | 0 | 320 | | | | | | | | | | | | | 3S193 | | 97.83% |
| | GM2 | 0 | 0 | 0 | 0 | | | | | | | | | | | | | B72.3 | | 5.34% |
| | | | | | | | | | | | | | | | | | | HMFG.1 | | 3.01% |
| 10. Heptavalent-KLH + 100 ug GPI-100 + polysorbate 80 (200 ul/mice) | Tn | 0 | 0 | 5120+ | 640 | 10.50% | 10.44% | 90.55% | 12.59% | 75.43% | 0.27% | 10.67% | 10.24% | 85.22% | 11.17% | 54.16% | 0.74% | 10-1 | -6.29% | -3.3% |
| | Tf | 0 | 0 | 5120 | 320 | | | | | | | | | | | | | | | |
| | sTn | 0 | 0 | 640 | 640 | | | | | | | | | | | | | | | |
| | Muc1-G5 | 0 | 0 | 5120 | 80 | | | | | | | | | | | | | | | |
| | Ley | 0 | 0 | 0 | 320 | | | | | | | | | | | | | | | |
| | globo H | 0 | 160 | 20 | 1280 | | | | | | | | | | | | | | | |
| | GM2 | 0 | 0 | 0 | 0 | | | | | | | | | | | | | | | |

-continued

Immunization of mice with Heptavalent-KLH
Conjugates* plus GPI-100 or QS-21
Mean Value:

Nov. 30, 2001

| Group # | Antigen | ELISA Pre IgG | ELISA Pre IgM | ELISA Post IgG | ELISA Post IgM | FACS MCF-7 Pre IgG | FACS MCF-7 Pre IgM | FACS MCF-7 Post IgG | FACS MCF-7 Post IgM | FACS MCF-7 1:200 IgG | FACS MCF-7 1:200 IgM | LSC #LSC Pre IgG | LSC #LSC Pre IgM | LSC #LSC Post IgG | LSC #LSC Post IgM | LSC 1:200 IgG | LSC 1:200 IgM | Mice # | CDC (MCF-7) Pre | CDC (MCF-7) Post |
|---|---|---|---|---|---|---|---|---|---|---|---|---|---|---|---|---|---|---|---|---|
| 11. Heptavalent-KLH + 10 ug QS-21 (200 ul/mice) | Tn | 0 | 20 | 5120+ | 160 | 10.75% | 10.39% | 90.96% | 4.8% | 70.67% | 0.23% | 9.92% | 10.74% | 70.28% | 8.33% | 40.71% | 0.29% | 11.1 | 1.84% | 10.93% |
| | Tf | 0 | 80 | 5120+ | 640 | | | | | | | | | | | | | 11-2 | 0.71% | 3.20% |
| | sTn | 0 | 0 | 2560 | 320 | | | | | | | | | | | | | 11-3 | 1.31% | 5.88% |
| | Muc1-G5 | 0 | 0 | 2560 | 160 | | | | | | | | | | | | | 11-4 | −1.58% | 18.36% |
| | Ley | 0 | 0 | 10 | 10 | | | | | | | | | | | | | 11-5 | 10.28% | 27.09% |
| | globo H | 0 | 80 | 40 | 640 | | | | | | | | | | | | | | | |
| | GM2 | 0 | 0 | 0 | 0 | | | | | | | | | | | | | | | |
| 12. Heptavalent-KLH + 3 ug ER803022 (200 ul/mice) | Tn | 0 | 0 | 1280 | 160 | 11.89% | 10.49% | 60.97% | 3.33% | 25.38% | 0.23% | 10.42% | 10.29% | 29.79% | 4.55% | 5.65% | 0.14% | | | |
| | Tf | 0 | 0 | 1280 | 80 | | | | | | | | | | | | | | | |
| | sTn | 0 | 0 | 80 | 80 | | | | | | | | | | | | | | | |
| | Muc1-G5 | 0 | 0 | 80 | 20 | | | | | | | | | | | | | | | |
| | Ley | 0 | 0 | 0 | 20 | | | | | | | | | | | | | | | |
| | globo H | 20 | 160 | 80 | 640 | | | | | | | | | | | | | | | |
| | GM2 | 0 | 0 | 0 | 0 | | | | | | | | | | | | | | | |
| 13. Heptavalent-KLH + 10 ug ER803732 (200 ul/mice) | Tn | 0 | 20 | 160 | 160 | 10.59% | 10.62% | 60.86% | 12.60% | 15.51% | 0.29% | 10.50% | 10.24% | 45.30% | 11.86% | 5.60% | 0.60% | | | |
| | Tf | 0 | 10 | 320 | 160 | | | | | | | | | | | | | | | |
| | sTn | 0 | 40 | 20 | 160 | | | | | | | | | | | | | | | |
| | Muc1-G5 | 0 | 0 | 160 | 80 | | | | | | | | | | | | | | | |
| | Ley | 0 | 0 | 0 | 80 | | | | | | | | | | | | | | | |
| | globo H | 20 | 80 | 80 | 320 | | | | | | | | | | | | | | | |
| | GM2 | 0 | 0 | 0 | 0 | | | | | | | | | | | | | | | |
| 14. 30ug KLH + 100 ug GPI-100 (100 ul/mice) | Tn | 0 | 0 | 0 | 160 | 10.62% | 11.08% | 11.02% | 4.10% | 5.61% | 0.45% | 10.32% | 10.68% | 9.09% | 2.47% | 7.96% | 0.73% | | | |
| | Tf | 0 | 40 | 0 | 320 | | | | | | | | | | | | | | | |
| | sTn | 0 | 0 | 0 | 80 | | | | | | | | | | | | | | | |
| | Muc1-G5 | 0 | 10 | 0 | 160 | | | | | | | | | | | | | | | |
| | Ley | 0 | 0 | 0 | 0 | | | | | | | | | | | | | | | |
| | globo H | 0 | 160 | 10 | 640 | | | | | | | | | | | | | | | |
| | GM2 | 0 | 0 | 0 | 160 | | | | | | | | | | | | | | | |
| | KLH | 0 | 10 | 5120++ | 320 | | | | | | | | | | | | | | | |

| | | ELISA (mean) | | | | ELISA (median) | | | | FACS MCF-7 | | | | |
|---|---|---|---|---|---|---|---|---|---|---|---|---|---|---|
| Group # | Antigen | Pre IgG | IgM | Post IgG | IgM | Pre IgG | IgM | Post IgG | IgM | Pre IgG | IgM | Post IgG | IgM | 1:200 IgG | IgM |
| 1. Heptavalent-KLH + 10 ug QS21 | Tn | 0 | 0 | 57440 | 640 | 0 | 0 | 25600 | 640 | 9.89% | 9.78% | 95.87% | 77.77% | 78.03% | 16.09% AVERAGE |
| | Tf | 0 | 0 | 10240++ | 260 | 0 | 0 | 10240+ | 160 | 9.39% | 9.94% | 96.40% | 80.96% | 79.70% | 8.16% |
| | sTn | 0 | 0 | 3520 | 580 | 0 | 0 | 1280 | 320 | | | | | | |
| | Muc1-G5 | 0 | 0 | 1280 | 80 | 0 | 0 | 1280 | 80 | | | | | | +CONTROL |
| | Ley | 0 | 32 | 1920 | 2560 | 0 | 0 | 1280 | 1280 | | | | | | VK-9 |
| | globo H | 0 | 48 | 672 | 128 | 0 | 80 | 640 | 160 | | | | | | MLS128 40.08% MEDIAN |
| | GM2 | | | | | | | | | | | | | | antiGM2 97.56% |
| | | | | | | | | | | | | | | | MBr-1 #### |
| | | | | | | | | | | | | | | | #### |
| 2. Heptavalent-KLH + 100 ug GPI100 | Tn | 0 | 0 | 19200 | 840 | 0 | 0 | 25600 | 320 | 10.15% | 10.36% | 92.97% | 79.87% | 66.63% | 28.35% |
| | Tf | 0 | 0 | 10240+ | 260 | 0 | 0 | 10240+ | 160 | 10.10% | 10.35% | 95.99% | 93.53% | 69.88% | 26.96% |
| | sTn | 0 | 0 | 720 | 360 | 0 | 0 | 320 | 80 | | | | | | |
| | Muc1-G5 | 0 | 0 | 1520 | 80 | 0 | 0 | 2560 | 160 | | | | | | |
| | Ley | 0 | 0 | 3920 | 680 | 0 | 0 | 5120 | 640 | | | | | | |
| | globo H | 0 | 0 | 320 | 176 | 0 | 0 | 80 | 160 | | | | | | |
| | GM2 | | | | | | | | | | | | | | |
| 3. Heptavalent-KLH + 100 ug GPI-100 (Lyophilized) | Tn | 0 | 0 | 32000 | 480 | 0 | 0 | 25600 | 320 | 10.29% | 10.14% | 92.85% | 62.94% | 65.36% | 18.34% |
| | Tf | 0 | 0 | 10240+ | 340 | 0 | 0 | 10240+ | 320 | 10.20% | 10.23% | 92.35% | 58.56% | 63.59% | 14.46% |
| | sTn | 0 | 0 | 1200 | 260 | 0 | 0 | 1280 | 320 | | | | | | |
| | Muc1-G5 | 0 | 0 | 1120 | 0 | 0 | 0 | 320 | 0 | | | | | | |
| | Ley | 0 | 0 | 320 | 720 | 0 | 0 | 480 | 640 | | | | | | |
| | globo H | 0 | 0 | 128 | 440 | 0 | 0 | 0 | 200 | | | | | | |
| | GM2 | | | | | | | | | | | | | | |
| 4. Heptavalent-KLH + 100 ug GPI100' + polysorbate80 | Tn | 0 | 0 | 38400 | 400 | 0 | 0 | 25600 | 160 | 10.14% | 10.18% | 91.34% | 57.09% | 70.79% | 6.70% |
| | Tf | 0 | 0 | 10240+ | 140 | 0 | 0 | 10240+ | 160 | 10.22% | 10.29% | 90.80% | 61.70% | 67.27% | 4.98% |
| | sTn | 0 | 0 | 1960 | 200 | 0 | 0 | 1280 | 320 | | | | | | |
| | Muc1-G5 | 0 | 0 | 4000 | 20 | 0 | 0 | 2560 | 0 | | | | | | |
| | Ley | 0 | 0 | 1440 | 960 | 0 | 0 | 1280 | 640 | | | | | | |
| | globo H | 0 | 40 | 100 | 224 | 0 | 40 | 120 | 160 | | | | | | |
| | GM2 | | | | | | | | | | | | | | |
| 5. Heptavalent-KLH + 100 ug GPI100 Cytoxan 25 mg/Kg (I.P.) Day - 1 | Tn | 0 | 0 | 61400 | 808 | 0 | 0 | 25600 | 640 | 9.92% | 10.30% | 89.55% | 72.17% | 64.38% | 12.43% |
| | Tf | 0 | 0 | 10240++ | 560 | 0 | 0 | 10240++ | 640 | 10.19% | 10.19% | 90.87% | 70.90% | 66.42% | 14.32% |
| | sTn | 0 | 0 | 520 | 480 | 0 | 0 | 640 | 320 | | | | | | |
| | Muc1-G5 | 0 | 0 | 3840 | 0 | 0 | 0 | 2560 | 0 | | | | | | |
| | Ley | 0 | 0 | 480 | 200 | 0 | 0 | 0 | 80 | | | | | | |
| | globo H | 0 | 0 | 32 | 540 | 0 | 0 | 0 | 400 | | | | | | |
| 6. Heptavalent-KLH + 100 ug GPI100 mAb CTLA-4 in vaccine (100 ug/mice) Day 0 Day 7 & 14 no CTLA-4 | Tn | 0 | 0 | 32000 | 250 | 0 | 0 | 25600 | 160 | 10.33% | 10.08% | 90.59% | 65.89% | 62.40% | 17.62% |
| | Tf | 0 | 0 | 10240+ | 1040 | 0 | 0 | 10240+ | 1280 | 10.26% | 10.01% | 91.50% | 62.97% | 63.04% | 8.00% |
| | sTn | 0 | 0 | 6240 | 180 | 0 | 0 | 1280 | 200 | | | | | | |
| | Muc1-G5 | 0 | 0 | 1950 | 40 | 0 | 0 | 2560 | 40 | | | | | | |
| | Ley | 0 | 0 | 180 | 2600 | 0 | 0 | 40 | 40 | | | | | | |
| | globo H | 0 | 0 | 0 | 240 | 0 | 0 | 0 | 240 | | | | | | |
| | GM2 | | | | | | | | | | | | | | |

Immunization of mice with Heptavalent-KLH Conjugates* plus QS-21 or GPI 100 with or without mAb 9H10 against CTLA-4.
Mean Value:

-continued

Immunization of mice with Heptavalent-KLH Conjugates* plus QS-21 or GPI 100 with or without mAb 9H10 against CTLA-4.
Mean Value:

| Group # | Antigen | ELISA (mean) | | | | ELISA (median) | | | | FACS MCF-7 | | | | 1:200 | |
|---|---|---|---|---|---|---|---|---|---|---|---|---|---|---|---|
| | | Pre IgG | IgM | Post IgG | IgM | Pre IgG | IgM | Post IgG | IgM | Pre IgG | IgM | Post IgG | IgM | IgG | IgM |
| 7. Heptavalent-KLH + 100 ug GPI100 mAb CTLA-4 in vaccine (100 ug/mice) Day 0 & 7 Day 14 no CTLA-4 | Tn | 0 | 0 | 32000 | 1600 | 0 | 0 | 25600 | 1280 | 10.05% | 10.31% | 90.31% | 85.42% | 67.29% | 29.21% |
| | Tf | 0 | 0 | 10240+ | 1920 | 0 | 0 | 10240+ | 1280 | 9.64% | 10.41% | 90.01% | 85.58% | 69.08% | 21.26% |
| | sTn | 0 | 0 | 2880 | 100 | 0 | 0 | 2560 | 80 | | | | | | |
| | Muc1-G5 | 0 | 0 | 6400 | 60 | 0 | 0 | 5120 | 80 | | | | | | |
| | Ley | 0 | 0 | 32 | 208 | 0 | 0 | 0 | 160 | | | | | | |
| | globo H | 0 | 0 | 32 | 220 | 0 | 0 | 0 | 240 | | | | | | |
| | GM2 | | | | | | | | | | | | | | |
| 8. Heptavalent-KLH + 100 ug GPI100 mAb CTLA-4 not in vaccine I.P. day -1, 0, 1 | Tn | 0 | 0 | 85333 | 40 | 0 | 0 | 51200+ | 40 | 9.69% | 10.15% | 91.29% | 45.33% | 63.00% | 6.19% |
| | Tf | 0 | 0 | 10240++ | 370 | 0 | 0 | 10240++ | 320 | 9.63% | 10.09% | 90.20% | 45.21% | 50.05% | 7.00% |
| | sTn | 0 | 0 | 480 | 0 | 0 | 0 | 640 | 0 | | | | | | |
| | Muc1-G5 | 0 | 0 | 3413 | 0 | 0 | 0 | 2560 | 0 | | | | | | |
| | Ley | 0 | 0 | 320 | 106 | 0 | 0 | 160 | 0 | | | | | | |
| | globo H | 0 | 0 | 53 | 240 | 0 | 0 | 0 | 80 | | | | | | |
| | GM2 | | | | | | | | | | | | | | |
| 9. Heptavalent-KLH + 100 ug GPI100 Control mAb ROR-g2 100 ug/mice I.P. day - 1.0.1 | Tn | 0 | 0 | 56320 | 640 | 0 | 0 | 51200 | 640 | 10.25% | 10.13% | 93.16% | 90.64% | 73.15% | 45.88% |
| | Tf | 0 | 0 | 10240+++ | 2720 | 0 | 0 | 10240+++ | 2560 | 10.27% | 10.21% | 94.17% | 95.54% | 76.62% | 30.38% |
| | sTn | 0 | 0 | 3040 | 5200 | 0 | 0 | 1280 | 320 | | | | | | |
| | Muc1-G5 | 0 | 0 | 10240 | 160 | 0 | 0 | 10240 | 160 | | | | | | |
| | Ley | 0 | 0 | 144 | 464 | 0 | 0 | 80 | 160 | | | | | | |
| | globo H | 0 | 0 | 112 | 848 | 0 | 0 | 80 | 640 | | | | | | |
| | GM2 | | | | | | | | | | | | | | |
| 10. Heptavalent-KLH + 100 ug GPI100 100 ug/mice | Tn | 0 | 0 | 81920 | 320 | 0 | 0 | 51200 | 160 | 10.42% | 9.98% | 88.03% | 76.96% | 67.02% | 33.26% |
| | Tf | 0 | 0 | 10240++ | 920 | 0 | 0 | 10240++ | 320 | 10.50% | 10.01% | 87.97% | 90.19% | 64.58% | 24.15% |
| | sTn | 0 | 0 | 2240 | 1440 | 0 | 0 | 2560 | 160 | | | | | | |
| | Muc1-G5 | 0 | 0 | 4160 | 40 | 0 | 0 | 2560 | 0 | | | | | | |
| | Ley | 0 | 144 | 144 | 2640 | 0 | 160 | 80 | 320 | | | | | | |
| | globo H | 0 | 0 | 0 | 224 | 0 | 0 | 0 | 160 | | | | | | |
| | GM2 | | | | | | | | | | | | | | |

Example 2

A Preclinical Study Comparing Approaches for Augmenting the Immunogenicity of a Heptavalent KLH-Conjugate Vaccine Against Epithelial Cancers Previously using a series of monovalent vaccines, we have demonstrated that the optimal method for inducing an antibody response against cancer cell-surface antigens is covalent conjugation of the antigens to keyhole limpet hemocyanin (KLH) and the use of a saponin adjuvant. In preparation for testing a polyvalent (heptavalent)-KLH conjugate vaccine in the clinic, we have tested the impact on antibody induction against the 7 antigens of several variables described by others to augment immunogenicity. We explore here the impact of approaches for decreasing suppression of the immune response (low dose cyclophosphamide and anti-CTLA4 mAb), different saponin adjuvants (QS-21 and GPI-0100), and different methods of formulation (lyophilization and use of polysorbate 80). After two sets of experiments, these results are clear:

1) Immunization with the heptavalent-KLH conjugate vaccine induces high titers of antibodies against Tn (median ELISA titer IgM/IgG 320/10,240), sTn (640/2560), TF (320/5120), MUC1 (80/20,480) and globo H (1280/10), lower titers of antibodies against Lewis Y (160/80) and only occasional antibodies against GM2.
2) These antibodies reacted with the purified synthetic antigens by ELISA, and with naturally expressed antigens on the cancer cell surface by FACS.
3) Neither decreasing suppression with low dose cyclophosphamide or anti-CTLA4 mAb, nor changing the standard formulation by lyophilization or use of polysorbate 80 had any impact on antibody titers.
4) The two saponin adjuvants were comparably potent at our standard doses (QS-21 10 ug and GPI-0100 100 ug) but a third experiment comparing higher doses is in progress.

The high titers of antibodies against this heptavalent vaccine and the inability of these additional approaches to further augment antibody titers confirms that the combination of conjugation to KLH and use of a saponin adjuvant is sufficiently optimized for testing in the clinic.

There is a broad and expanding body of pre-clinical and clinical studies demonstrating that naturally acquired, actively induced, and passively administered antibodies are able to eliminate circulating tumor cells and micro metastases (1). Induction of antibodies against tumor antigens is more difficult than induction of antibodies against viral and bacterial antigens because most tumor antigens are normal or slightly modified auto antigens and because actively growing tumors may set in motion mechanisms which suppress the anti-cancer cell immune response. Consequently it may be necessary to overcome not only some level of tolerance but also some additional level of active suppression, making the immunization approach critical. We have previously reported that the optimal approach for induction of antibodies against gangliosides and a variety of other carbohydrate and peptide antigens is covalent attachment of the tumor antigen to an immunogenic carrier molecule (keyhole limpet hemocyanin (KLH) was optimal (2,3)) plus the use of a potent immunological adjuvant. In our previous experience saponin adjuvants such as QS-21 and GPI-0100 were the optimal adjuvants (4,5).

In preparation for clinical trials with a heptavalent KLH-conjugate vaccine we test here the impact of several variables including 1) vaccine formulation (lyophilization or the use of polysorbate 80), 2) decreasing suppression (low dose cyclophosphamide or anti-CTLA4 mAb), or 3) various doses of the two saponin adjuvants QS-21 and GPI-0100, on antibody titers against the individual antigens and tumor cells expressing these antigens.

Pathogen-free female BALB/c or C57BL/6 mice 6-10 weeks of age were obtained from the Jackson Laboratory (Bar Harbor, Me.). QS-21 was obtained from Aquila Biopharmaceuticals (Framingham, M A (now Antigenics Inc., NYC, NY)), GPI-0100 was obtained from Galenica Pharmaceuticals, Inc. (Birmingham, Ala.). Cytoxan (25 mg/kg) was purchased and injected IP one day prior to the first immunization. The hybridoma for murine monoclonal antibody CTLA-4 was obtained from Jim Allison (Berkeley, Calif.) and the mAb was prepared by Dr. Polly Gregor (MSKCC). The reactivity of mAb with CTLA-4 was confirmed. Polysorbate 80 was purchased.

Immunization of mice: groups of five mice were immunized 3 times at one week intervals with the heptavalent vaccine containing 3 mcg of each of the 7 antigens covalently conjugated to KLH and mixed with GPI-0100 or QS-21 as indicated. Vaccines were administered subcutaneously over the lower abdomen. A 4th, booster, immunization was given at week 8.

Serological Assays For the ELISA assay, glycosylated MUC1, globo H, Lewis Y or GM2, or Tn, sTn or TP conjugated to BSA, were coated on ELISA plates at an antigen dose of 0.1-0.2 mcg per well.

Phosphatase-conjugated goat anti-mouse IgG or IgM was added at a dilution of 1:200 (Southern Biotechnology Associates, Inc., Birmingham, Ala.). Antibody titer was the highest dilution yielding absorbance of 0.10 or greater.

FACS analysis: MCF-7 human breast cancer cells expressing all seven antigens but especially Lewis Y and MUC1 and sTn, and LSC expressing especially Lewis Y, sTn and Tn, were used. Single cell suspensions of $5 \times 10^7$ cells/tube were washed in PBS with 3% fetal calf serum and incubated with 20 mcl of full strength or 1/200 diluted antisera for 30 minutes on ice. 20 microliters of 1/15 goat anti-mouse IgG or IgM labeled with FITC were all added and percent positive cells and mean fluorescent intensity (MFI) of stained cells analyzed using a F ACScan (Becton Dickenson, Calif.). Pre and post vaccination sera were analyzed together and the pre-treatment percent positive cells set at 10%.

Comparison of the Immune Response after Immunization with Monovalent and Hexavalent-KLH Conjugate Vaccines Against Prostate Cancer Glycolipid and glycoprotein differentiation antigens such as GM2, Globo H, Lewis y, Tn, TF, and mucin 1 (MUC1) are over-expressed on the cell surface of many tumors. Of the many approaches to immunization we have tested, covalent conjugation of antigens such as these to keyhole limpet hemocyanin (KLH) plus the use of immunological adjuvant QS-21 has been the optimal approach for inducing IgM and IgG antibodies. Immunization of patients with monovalent vaccines containing these antigens has demonstrated the consistent immunogenicity and safety of these vaccines. However, to overcome the heterogeneous nature of tumors, and of the immune response in different individuals, we have recently vaccinated a small group of patients (prostate cancer with rising PSA, but free of detectable disease) with a hexavalent-KLH vaccine containing GM2, Globo H, Le$^y$, Tn(c), TF(c) and glycosylated MUC1 individually conjugated with KLH and mixed with immunological adjuvant QS-21. The main objective of this presentation is to compare the immune response of the six initial patients receiving hexavalent vaccine with the immune responses of patients who had previously been immunized with the respective monovalent vaccines. All patients were vaccinated six times (weeks 1, 2, 3, 7, 19 and 31) and bloods obtained pre treatment and on weeks 7 and 9 were tested at one time. RECIPRICOL MEAN PEAK ELISA TITER AFTER IMMUNIZATION IgM/IgG.

| Antigen | GM2 | Globo H | Le$^y$ | Tn | TF | MUC1 |
|---|---|---|---|---|---|---|
| Poly-valent vaccine | Pending | 160/0 | 0/0 | 640/640 | 1280/160 | 40/320 |
| Individual Vaccine | Pending | 160/0 | 0/10 | 1280/2560 | 1280/160 | 2560/320 |

Because of the low response against Le$^y$, we are continuing studies aimed at creating a more immunogenic Le$^y$ vaccine. Comparing the responses induced by monovalent and hexavalent vaccines, there was no significant difference in the antibody responses against any of the five antigens tested to date. Combination of six individual conjugates into a single vaccine does not significantly change the antibody response against the individual antigens.

Experiment 1: Median ELISA titers and FACS results after vaccination of groups of 5 Balb/c mice with Heptavalent-KLH conjugate

| | | ELISA(mean) | | | | ELISA(median) | | | |
|---|---|---|---|---|---|---|---|---|---|
| | | Pre | | Post | | Pre | | Post | |
| Group # | Antigen | IgG | IgM | IgG | IgM | IgG | IgM | IgG | IgM |
| 1. Heptavalent-KLH + 10 ug QS21 | Tn | 0 | 0 | 57440 | 640 | 0 | 0 | 25600 | 640 |
| | Tf | 0 | 0 | 10240++ | 260 | 0 | 0 | 10240+ | 160 |
| | sTn | 0 | 0 | 3520 | 580 | 0 | 0 | 1280 | 320 |
| | Muc1-G5 | 0 | 0 | 1280 | 80 | 0 | 0 | 1280 | 80 |
| | Ley | 0 | 32 | 1920 | 2560 | 0 | 0 | 1280 | 1280 |
| | globo H | 0 | 48 | 672 | 128 | 0 | 80 | 640 | 160 |
| | GM2 | | | | | | | | |
| 2. Heptavalent-KLH + 100 ug GPI100 | Tn | 0 | 0 | 19200 | 840 | 0 | 0 | 25600 | 320 |
| | Tf | 0 | 0 | 10240+ | 260 | 0 | 0 | 10240+ | 160 |
| | sTn | 0 | 0 | 720 | 360 | 0 | 0 | 320 | 80 |
| | Muc1-G5 | 0 | 0 | 1520 | 80 | 0 | 0 | 2560 | 160 |
| | Ley | 0 | 0 | 3920 | 680 | 0 | 0 | 5120 | 640 |
| | globo H | 0 | 0 | 320 | 176 | 0 | 0 | 80 | 160 |
| | GM2 | | | | | | | | |
| 3. Heptavalent-KLH + 100 ug GPI-100 (Lyophilized) | Tn | 0 | 0 | 32000 | 480 | 0 | 0 | 25600 | 320 |
| | Tf | 0 | 0 | 10240+ | 340 | 0 | 0 | 10240+ | 320 |
| | sTn | 0 | 0 | 1200 | 260 | 0 | 0 | 1280 | 320 |
| | Muc1-G5 | 0 | 0 | 1120 | 0 | 0 | 0 | 320 | 0 |
| | Ley | 0 | 0 | 320 | 720 | 0 | 0 | 480 | 640 |
| | globo H | 0 | 0 | 128 | 440 | 0 | 0 | 0 | 200 |
| | GM2 | | | | | | | | |
| 4. Heptavalent-KLH + 100 ug GPI100' + polysorbate80 | Tn | 0 | 0 | 38400 | 400 | 0 | 0 | 25600 | 160 |
| | Tf | 0 | 0 | 10240+ | 140 | 0 | 0 | 10240+ | 160 |
| | sTn | 0 | 0 | 1960 | 200 | 0 | 0 | 1280 | 320 |
| | Muc1-G5 | 0 | 0 | 4000 | 20 | 0 | 0 | 2560 | 0 |
| | Ley | 0 | 0 | 1440 | 960 | 0 | 0 | 1280 | 640 |
| | globo H | 0 | 40 | 100 | 224 | 0 | 40 | 120 | 160 |
| | GM2 | | | | | | | | |
| 5. Heptavalent-KLH + 100 ug GPI100 Cytoxan 25 mg/Kg (I.P.) Day −1 | Tn | 0 | 0 | 61400 | 808 | 0 | 0 | 25600 | 640 |
| | Tf | 0 | 0 | 10240++ | 560 | 0 | 0 | 10240++ | 640 |
| | sTn | 0 | 0 | 520 | 480 | 0 | 0 | 640 | 320 |
| | Muc1-G5 | 0 | 0 | 3840 | 0 | 0 | 0 | 2560 | 0 |
| | Ley | 0 | 0 | 480 | 200 | 0 | 0 | 0 | 80 |
| | globo H | 0 | 0 | 32 | 540 | 0 | 0 | 0 | 400 |
| | GM2 | | | | | | | | |
| 6. Heptavalent-KLH + 100 ug GPI100 mAb CTLA-4 in vaccine (100 ug/mice) Day 0 Day 7 & 14 no CTLA-4 | Tn | 0 | 0 | 32000 | 250 | 0 | 0 | 25600 | 160 |
| | Tf | 0 | 0 | 10240+ | 1040 | 0 | 0 | 10240+ | 1280 |
| | sTn | 0 | 0 | 6240 | 180 | 0 | 0 | 1280 | 200 |
| | Muc1-G5 | 0 | 0 | 1950 | 40 | 0 | 0 | 2560 | 40 |
| | Ley | 0 | 0 | 180 | 2600 | 0 | 0 | 40 | 40 |
| | globo H | 0 | 0 | 0 | 240 | 0 | 0 | 0 | 240 |
| | GM2 | | | | | | | | |
| 7. Heptavalent-KLH + 100 ug GPI100 mAb CTLA-4 in vaccine (100 ug/mice) Day 0 & 7 Day 14 no CTLA-4 | Tn | 0 | 0 | 32000 | 1600 | 0 | 0 | 25600 | 1280 |
| | Tf | 0 | 0 | 10240+ | 1920 | 0 | 0 | 10240+ | 1280 |
| | sTn | 0 | 0 | 2880 | 100 | 0 | 0 | 2560 | 80 |
| | Muc1-G5 | 0 | 0 | 6400 | 60 | 0 | 0 | 5120 | 80 |
| | Ley | 0 | 0 | 32 | 208 | 0 | 0 | 0 | 160 |
| | globo H | 0 | 0 | 32 | 220 | 0 | 0 | 0 | 240 |
| | GM2 | | | | | | | | |

-continued

Experiment 1: Median ELISA titers and FACS results after vaccination of groups of 5 Balb/c mice with Heptavalent-KLH conjugate

| Group | Antigen | | | | | | | | |
|---|---|---|---|---|---|---|---|---|---|
| 8. Heptavalent-KLH + 100 ug GPI100 mAb CTLA-4 not in vaccine I.P. day −1, 0, 1 | Tn | 0 | 0 | 85333 | 40 | 0 | 0 | 51200+ | 40 |
| | Tf | 0 | 0 | 10240++ | 370 | 0 | 0 | 10240++ | 320 |
| | sTn | 0 | 0 | 480 | 0 | 0 | 0 | 640 | 0 |
| | Muc1-G5 | 0 | 0 | 3413 | 0 | 0 | 0 | 2560 | 0 |
| | Ley | 0 | 0 | 320 | 106 | 0 | 0 | 160 | 0 |
| | globo H | 0 | 0 | 53 | 240 | 0 | 0 | 0 | 80 |
| | GM2 | | | | | | | | |
| 9. Heptavalent-KLH + 100 ug GPI100 Control mAb ROR-g2 100 ug/mice I.P. day −1, 0, 1 | Tn | 0 | 0 | 56320 | 640 | 0 | 0 | 51200 | 640 |
| | Tf | 0 | 0 | 10240+++ | 2720 | 0 | 0 | 10240+++ | 2560 |
| | sTn | 0 | 0 | 3040 | 5200 | 0 | 0 | 1280 | 320 |
| | Muc1-G5 | 0 | 0 | 10240 | 160 | 0 | 0 | 10240 | 160 |
| | Ley | 0 | 0 | 144 | 464 | 0 | 0 | 80 | 160 |
| | globo H | 0 | 0 | 112 | 848 | 0 | 0 | 80 | 640 |
| | GM2 | | | | | | | | |
| 10. Heptavalent-KLH + 100 ug GPI100 100 ug/mice | Tn | 0 | 0 | 81920 | 320 | 0 | 0 | 51200 | 160 |
| | Tf | 0 | 0 | 10240++ | 920 | 0 | 0 | 10240++ | 320 |
| | sTn | 0 | 0 | 2240 | 1440 | 0 | 0 | 2560 | 160 |
| | Muc1-G5 | 0 | 0 | 4160 | 40 | 0 | 0 | 2560 | 0 |
| | Ley | 0 | 144 | 144 | 2640 | 0 | 160 | 80 | 320 |
| | globo H | 0 | 0 | 0 | 224 | 0 | 0 | 0 | 160 |
| | GM2 | | | | | | | | |

| | | FACS | | MCF-7 | | | | | |
|---|---|---|---|---|---|---|---|---|---|
| | | Pre | | Post | | 1:200 | | | |
| Group # | Antigen | IgG | IgM | IgG | IgM | IgG | IgM | +CONTROL | |
| 1. Heptavalent-KLH + 10 ug QS21 | Tn | 10% | 10% | 96% | 78% | 78% | 16% | VK-9 | 40.08% |
| | Tf | 9% | 10% | 96% | 81% | 80% | 8% | MLS128 | 97.56% |
| | sTn | | | | | | | antiGM2 | 98.87% |
| | Muc1-G5 | | | | | | | MBr-1 | 58.06% |
| | Ley | | | | | | | | |
| | globo H | | | | | | | | |
| | GM2 | | | | | | | | |
| 2. Heptavalent-KLH + 100 ug GPI100 | Tn | 10% | 10% | 93% | 80% | 67% | 28% | | |
| | Tf | 10% | 10% | 96% | 94% | 70% | 27% | | |
| | sTn | | | | | | | | |
| | Muc1-G5 | | | | | | | | |
| | Ley | | | | | | | | |
| | globo H | | | | | | | | |
| | GM2 | | | | | | | | |
| 3. Heptavalent-KLH + 100 ug GPI-100 (Lyophilized) | Tn | 10% | 10% | 93% | 63% | 65% | 18% | | |
| | Tf | 10% | 10% | 92% | 59% | 64% | 14% | | |
| | sTn | | | | | | | | |
| | Muc1-G5 | | | | | | | | |
| | Ley | | | | | | | | |
| | globo H | | | | | | | | |
| | GM2 | | | | | | | | |
| 4. Heptavalent-KLH + 100 ug GPI100' + polysorbate80 | Tn | 10% | 10% | 91% | 57% | 71% | 7% | | |
| | Tf | 10% | 10% | 91% | 62% | 67% | 5% | | |
| | sTn | | | | | | | | |
| | Muc1-G5 | | | | | | | | |
| | Ley | | | | | | | | |
| | globo H | | | | | | | | |
| | GM2 | | | | | | | | |
| 5. Heptavalent-KLH + 100 ug GPI100 Cytoxan 25 mg/Kg (I.P.) Day −1 | Tn | 10% | 10% | 90% | 72% | 64% | 12% | | |
| | Tf | 10% | 10% | 91% | 71% | 66% | 14% | | |
| | sTn | | | | | | | | |
| | Muc1-G5 | | | | | | | | |
| | Ley | | | | | | | | |
| | globo H | | | | | | | | |
| | GM2 | | | | | | | | |

Experiment 1: Median ELISA titers and FACS results after vaccination of groups of 5 Balb/c mice with Heptavalent-KLH conjugate

| Group | Antigen | | | | | | |
|---|---|---|---|---|---|---|---|
| 6. Heptavalent-KLH + 100 ug GPI100 mAb CTLA-4 in vaccine (100 ug/mice) Day 0 Day 7 & 14 no CTLA-4 | Tn<br>Tf<br>sTn<br>Muc1-G5<br>Ley<br>globo H<br>GM2 | 10%<br>10% | 10%<br>10% | 91%<br>92% | 66%<br>63% | 62%<br>63% | 18%<br>8% |
| 7. Heptavalent-KLH + 100 ug GPI100 mAb CTLA-4 in vaccine (100 ug/mice) Day 0 & 7 Day 14 no CTLA-4 | Tn<br>Tf<br>sTn<br>Muc1-G5<br>Ley<br>globo H<br>GM2 | 10%<br>10% | 10%<br>10% | 90%<br>90% | 85%<br>86% | 67%<br>69% | 29%<br>21% |
| 8. Heptavalent-KLH + 100 ug GPI100 mAb CTLA-4 not in vaccine I.P. day −1, 0, 1 | Tn<br>Tf<br>sTn<br>Muc1-G5<br>Ley<br>globo H<br>GM2 | 10%<br>10% | 10%<br>10% | 91%<br>90% | 45%<br>45% | 63%<br>50% | 6%<br>7% |
| 9. Heptavalent-KLH + 100 ug GPI100 Control mAb ROR-g2 100 ug/mice I.P. day −1, 0, 1 | Tn<br>Tf<br>sTn<br>Muc1-G5<br>Ley<br>globo H<br>GM2 | 10%<br>10% | 10%<br>10% | 93%<br>94% | 91%<br>96% | 73%<br>77% | 46%<br>30% |
| 10. Heptavalent-KLH + 100 ug GPI100 100 ug/mice | Tn<br>Tf<br>sTn<br>Muc1-G5<br>Ley<br>globo H<br>GM2 | 10%<br>11% | 10%<br>10% | 88%<br>88% | 77%<br>90% | 67%<br>65% | 33%<br>24% |

Experiment 2: Median ELISA titers and FACS results against MCF-7 and LSC cells after vaccination groups of 5 C57BL/6 Mice with heptavalent-KLH conjugate vaccine

| | | ELISA | | | | FACS withMCF-7 | | | | | | # LSC | | FACS with LSC | | | |
|---|---|---|---|---|---|---|---|---|---|---|---|---|---|---|---|---|---|
| | | Pre | | Post | | Pre | | Post | | 1:200 | | Pre | | Post | | 1:200 | |
| Group # | Antigen | IgG | IgM | IgG | IgM | IgG | IgM | IgG | IgM | IgG | IgM | IgG | IgM | IgG | IgM | IgG | IgM |
| Heptavalent-KLH + 100 ug GPI100 (200 ul/mice) | Tn | 0 | 10 | 5120+ | 320 | 10% | 11% | 91.61% | 18.46% | 80% | 18% | 10% | 11% | 96.04% | 39.25% | 84% | 39% |
| | Tf | 0 | 10 | 5120 | 320 | | | 99% | 24% | 82% | 21% | | | | | | |
| | sTn | 0 | 0 | 2560 | 640 | | | | | | | | | | | | |
| | Muc1-G5 | 0 | 0 | 5120++ | 80 | | | | | | | | | | | | |
| | Ley | 0 | 0 | 80 | 160 | | | | | | | | | | | | |
| | globo H | 0 | 80 | 10 | 1280 | | | | | | | | | | | | |
| | GM2 | 0 | 0 | 0 | 10 | | | | | | | | | | | | |
| Heptavalent-KLH + 100 ug GPI (old batch) (200 ul/mice) | Tn | 0 | 0 | 2560 | 40 | 11% | 11% | 84.31% | 9.89% | 60% | 10% | 10% | 10% | 92.22% | 16.68% | 63% | 17% |
| | Tf | 0 | 0 | 5120 | 40 | | | | | | | | | | | | |
| | sTn | 0 | 0 | 320 | 160 | | | | | | | | | | | | |
| | Muc1-G5 | 0 | 0 | 1280 | 0 | | | | | | | | | | | | |
| | Ley | 0 | 0 | 40 | 320 | | | | | | | | | | | | |
| | globo H | 0 | 80 | 0 | 320 | | | | | | | | | | | | |
| | GM2 | 0 | 0 | 0 | 0 | | | | | | | | | | | | |

-continued

Experiment 2: Median ELISA titers and FACS results against MCF-7 and LSC cells after vaccination groups of 5 C57BL/6 Mice with heptavalent-KLH conjugate vaccine

| | | ELISA | | | | FACS withMCF-7 | | | | | | FACS with LSC | | | | | |
| | | Pre | | Post | | Pre | | Post | | 1:200 | | # LSC Pre | | Post | | 1:200 | |
| Group # | Antigen | IgG | IgM | IgG | IgM | IgG | IgM | IgG | IgM | IgG | IgM | IgG | IgM | IgG | IgM | IgG | IgM |
|---|---|---|---|---|---|---|---|---|---|---|---|---|---|---|---|---|---|
| Heptavalent-KLH + 100 ug GPI-100 + polysorbate 80 (200 ul/ mice) | Tn | 0 | 0 | 5120+ | 640 | 11% | 10% | 90.55% | 12.59% | 75% | 13% | 11% | 10% | 85.22% | 11.17% | 54% | 11% |
| | Tf | 0 | 0 | 5120 | 320 | | | | | | | | | | | | |
| | sTn | 0 | 0 | 640 | 640 | | | | | | | | | | | | |
| | Muc1-G5 | 0 | 0 | 5120 | 80 | | | | | | | | | | | | |
| | Ley | 0 | 0 | 0 | 320 | | | | | | | | | | | | |
| | globo H | 0 | 160 | 20 | 1280 | | | | | | | | | | | | |
| | GM2 | 0 | 0 | 0 | 0 | | | | | | | | | | | | |
| Heptavalent-KLH + 10 ug QS-21 (200 ul/ mice) | Tn | 0 | 20 | 5120+ | 160 | 11% | 10% | 90.96% | 4.8% | 71% | 5% | 10% | 11% | 70.28% | 8.33% | 41% | 8% |
| | Tf | 0 | 80 | 5120+ | 640 | | | | | | | | | | | | |
| | sTn | 0 | 0 | 2560 | 320 | | | | | | | | | | | | |
| | Muc1-G5 | 0 | 0 | 2560 | 160 | | | | | | | | | | | | |
| | Ley | 0 | 0 | 10 | 10 | | | | | | | | | | | | |
| | globo H | 0 | 80 | 40 | 640 | | | | | | | | | | | | |
| | GM2 | 0 | 0 | 0 | 0 | | | | | | | | | | | | |
| Heptavalent-KLH + 10 ug ER803732 (200 ul/ mice) | Tn | 0 | 20 | 160 | 160 | 11% | 11% | 60.86% | 12.60% | 16% | 13% | 11% | 10% | 45.30% | 11.86% | 6% | 12% |
| | Tf | 0 | 10 | 320 | 160 | | | | | | | | | | | | |
| | sTn | 0 | 40 | 20 | 160 | | | | | | | | | | | | |
| | Muc1-G5 | 0 | 0 | 160 | 80 | | | | | | | | | | | | |
| | Ley | 0 | 0 | 0 | 80 | | | | | | | | | | | | |
| | globo H | 20 | 80 | 80 | 320 | | | | | | | | | | | | |
| | GM2 | 0 | 0 | 0 | 0 | | | | | | | | | | | | |

Protocol 00-106:
Pilot Phas Trial: Vaccination of Patients Who Have Ovarian, Fallopian Tube or Peritoneal Cancer with A Polyvalent Vaccine-KLH Conjugate + QS-21

| | | Vaccine: | 10ug GM2 | 10ug Globo-H | 10ug LeY | 3ug Muc1G5 | 3ug Tn(c) | 3ug S-Tn(c) | 3ug TF(c) | | | | |
|---|---|---|---|---|---|---|---|---|---|---|---|---|---|
| | | | | | | | Patient Name | | | | | | |
| Patient # | Vaccination | Serology | Sera # | Muc1-IG5 IgM | IgG | Globo-H IgM | IgG | LeY IgM | IgG | GM2 IgM | Tn(c) IgM | IgG | S-Tn(c) IgM | IgG | Tf(c) IgM | IgG |
| | | | | Jun. 12, 2002 | Jun. 12, 2002 | Jun. 27, 2002 | Jun. 19, 2002 | Jun. 21, 2002 | Jun. 21, 2002 | Jun. 24, 2002 | Jun. 24, 2002 | | | Jun. 25, 2002 | Jun. 25, 2002 |
| Patient 1 | Jul. 03, 2001 | Jul. 03, 2001 | P7OVQ 2 | 0 | 0 | 0 | 0 | 0 | 0 | 0 | 0 | | | 0 | 20 |
| | Jul. 10, 2001 | Jul. 31, 2001 | P7OVQ 6 | 2560 | 640 | 40 | 0 | 0 | 0 | 0 | 0 | 20 | | 1280 | 160 |
| | Jul. 17, 2001 | Aug. 14, 2001 | P7OVQ 9 | 2560 | 640 | 40 | 0 | 0 | 0 | 0 | 0 | 20 | | 1280 | 160 |
| | Aug. 14, 2001 | Aug. 08, 2001 | P7OVQ 15 | 2560 | 320 | 40 | 0 | 0 | 0 | 0 | 0 | 20 | | 1280 | 320 |
| | | OFF TRIAL | | | | | | | | | | | | | |
| | | | (+) Control M62 | 2560 | 640 | | 2560 | | | | | | | | |
| | | | Positive control S193 (1 mg/ml) | | | | | 6400 | | | | | | | |
| | | | Positive control | | | | | | 2560 | | | | | | |
| | | | Positive control | | | | | | | 640 | | | | | |
| | | | Positive control | | | | | | | | | 2560 | | | |
| | | | Positive control | | | 2560 | | | | | | | | | |
| | | | Positive control | | | | | | | | | | | 2560 | 2560 |
| | | | | Jun. 04, 2002 | Jun. 04, 2002 | Jun. 27, 2002 | Jun. 26, 2002 | | | | | | | | |
| Patient 2 | Jul. 03, 2001 | Jul. 03, 2001 | P7OVQ 3 | 0 | 0 | 0 | 0 | | | | | | | | |
| | Jul. 10, 2001 | Jul. 31, 2001 | P7OVQ 7 | 80 | 20 | 0 | 0 | | | | | | | | |
| | Jul. 17, 2001 | Aug. 14, 2001 | P7OVQ 10 | 40 | 20 | 0 | 0 | | | | | | | | |
| | Aug. 14, 2001 | Aug. 28, 2001 | P7OVQ 13 | 20 | 40 | 0 | 0 | | | | | | | | |
| | Oct. 09, 2001 | Sep. 25, 2001 | P7OVQ 20 | 20 | 20 | 0 | 0 | | | | | | | | |
| | | Oct. 09, 2001 | P7OVQ 24 | 20 | 20 | 0 | 0 | | | | | | | | |
| | | Oct. 23, 2001 | P7OVQ 30 | 20 | 20 | 0 | 0 | | | | | | | | |
| | | Jan. 11, 2002 | P7OVQ 49 | 0 | 0 | 0 | 0 | | | | | | | | |
| | | Jun. 07, 2002 | P7OVQ 65 | | | | | | | | | | | | |
| | | | (+) Control | | | | | | | | | | | | |
| | | | Positive control | 2560 | 640 | 640 | 2560 | | | | | | | | |
| | | | Positive control | | | | | | | | | | | | |
| | | | Positive control | | | | | | | | | | | | |

Protocol 00-106:
Pilot Phas Trial: Vaccination of Patients Who Have Ovarian, Fallopian Tube or Peritoneal Cancer with A Polyvalent Vaccine-KLH Conjugate + QS-21

| | | Vaccine: | 10ug GM2 | 10ug Globo-H | 10ug LeY | 3ug MucIG5 | 3ug Tn(c) | 3ug S-Tn(c) | 3ug TF(c) | | | | |
|---|---|---|---|---|---|---|---|---|---|---|---|---|---|
| | | | | | | | | | | | | | Patient Name |
| | | | Muc1-IG5 | Globo-H | | | LeY | | GM2 | | Tn(c) | STn(c) | Tf | |
| | | | IgM | IgG | IgM | IgG | IgM | IgG | IgM | IgG | IgM | IgG | IgM | IgG | IgM | IgG |
| Medical # | Vaccination | Serology | Sera # | | | | | | | | | | | | |
| Patient 3 | Jul. 10, 2001 | Jul. 10, 2001 | P7OVQ 4 | | | Jun. 07, 2002 | | Jun. 27, 2002 | | Jun. 26, 2002 | | | | | |
| | Jul. 17, 2001 | Aug. 07, 2001 | P7OVQ 8 | 1280 | 160 | 20 | 0 | | | | | | | | |
| | Jul. 24, 2001 | Aug. 21, 2001 | P7OVQ 12 | 320 | 40 | 160 | 0 | | | | | | | | |
| | Aug. 21, 2001 | Sep. 04, 2001 | P7OVQ 18 | 160 | 80 | 80 | 0 | | | | | | | | |
| | | Oct. 02, 2001 | P7OVQ 22 | 80 | 40 | 80 | 0 | | | | | | | | |
| | | Oct. 16, 2001 | P7OVQ 26 | 40 | 80 | 40 | 0 | | | | | | | | |
| | Oct. 16, 2001 | Oct. 30, 2001 | P7OVQ 33 | 80 | 80 | 40 | 0 | | | | | | | | |
| | | Oct. 08, 2002 | P7OVQ 47 | 40 | 40 | 80 | 0 | | | | | | | | |
| | | | (+) Control M62 | 2560 | 1280 | 1280 | 2560 | | | | | | | | |
| | | | Positive control | | | | | | | | | | | | |
| | | | Positive control | | | | | | | | | | | | |
| patient 4 | Jul. 24, 2001 | Jul. 24, 2001 | P7OVQ 5 | 0 | 0 | Jun. 10, 2002 | | | | | | | | | |
| | Jul. 31, 2001 | Aug. 21, 2001 | P7OVQ 14 | 1280 | 80 | 80 | 0 | | | | | | | | |
| | Aug. 07, 2001 | Sep. 04, 2001 | P7OVQ 17 | 1280 | 40 | 40 | 0 | | | | | | | | |
| | Sep. 04, 2001 | Sep. 18, 2001 | P7OVQ 23 | 160 | 20 | 20 | 0 | | | | | | | | |
| | | Oct. 16, 2001 | P7OVQ 27 | 160 | 20 | 20 | 0 | | | | | | | | |
| | Oct. 30, 2001 | Oct. 30, 2001 | P7OVQ 32 | 60 | 40 | 40 | 0 | | | | | | | | |
| | | Nov. 13, 2001 | P7OVQ 36 | 20 | 20 | 20 | 0 | | | | | | | | |
| | | Jan. 22, 2002 | P7OVQ 52 | 20 | 20 | 20 | 0 | | | | | | | | |
| | | Mar. 26, 2002 | P7OVQ 63 | 20 | 20 | | | | | | | | | | |
| | | | (+) Control M62 | 1280 | 640 | | | | | | | | | | |
| | | | | Jun. 12, 2002 | Jun. 12, 2002 | Jun. 27, 2002 | Jun. 19, 2002 | Jun. 21, 2002 | Jun. 21, 2002 | Jun. 24, 2002 | Jun. 24, 2002 | | | Jun. 25, 2002 | Jun. 25, 2002 |
| patient 5 | Aug. 16, 2001 | Aug. 16, 2001 | P7OVQ 11 | 0 | 0 | 0 | 0 | 0 | 0 | 0 | 0 | | | 0 | 0 |
| | Aug. 23, 2001 | Sep. 27, 2001 | P7OVQ 21 | 80 | 80 | 0 | 0 | 0 | 0 | 0 | 0 | | | 40 | 160 |
| | Aug. 30, 2001 | Oct. 11, 2001 | P7OVQ 25 | 40 | 80 | 0 | 0 | 0 | 0 | 0 | 0 | | | 0 | 160 |
| | Sep. 27, 2001 | OFF TRIAL | | | | | | | | | | | | | |
| | | | (+) Control M62 | 2560 | 640 | | 2560 | 6400 | 2560 | | | | | | |
| | | | Positive control S193 (1 mg/ml) | | | | | | | | | | | | |
| | | | Positive control | | | | | | | | | | | | |

-continued

Protocol 00-106:
Pilot Phas Trial: Vaccination of Patients Who Have Ovarian, Fallopian Tube or Peritoneal Cancer with A Polyvalent Vaccine-KLH Conjugate + QS-21

| | Vaccine: | 10ug GM2 | 10ug Globo-H | 10ug LeY | 3ug MucIG5 | 3ug Tn(c) | 3ug S-Tn(c) | 3ug TF(c) |
|---|---|---|---|---|---|---|---|---|
| | | Positive control | | | | | | |
| | | Positive control | | 2560 | | | | |
| | | Positive control | | | | | 640 | |
| | | Positive control | | | | | | 2560 |
| | | | Jun. 17, 2002 | Jun. 17, 2002 | | | | |
| patient 6 | Aug. 30, 2001 | P7OVQ 18 | 0 | | | | | |
| | Sep. 06, 2001 | P7OVQ 19 | 160 | 20 | | | | |
| | Sep. 13, 2001 | P7OVQ 31 | 40 | 20 | | | | |
| | Oct. 25, 2001 | P7OVQ 39 | 20 | 0 | | | | |
| | Nov. 22, 2001 | P7OVQ 41 | 20 | 20 | | | | |
| | Oct. 11, 2001 | P7OVQ 44 | 20 | 20 | | | | |
| | Dec. 06, 2001 | P7OVQ 62 | 20 | 20 | | | | |
| | Dec. 20, 2001 | (+) Control | | | | | | |
| | Mar. 08, 2002 | M62 | 2560 | 320 | | | | 2560 |
| | | | Jun. 13, 2002 | Jun. 13, 2002 | Jun. 19, 2002 | Jun. 27, 2002 | Jun. 21, 2002 | Jun. 21, 2002 | Jun. 24, 2002 | Jun. 24, 2002 |
| patient 7 | Oct. 19, 2001 | P7OVQ 28 | 0 | 0 | (re-do) | 0 | 0 | 0 | 0 |
| | Oct. 26, 2001 | P7OVQ 35 | 640 | 40 | (re-do) | 0 | 0 | 0 | 0 |
| | Nov. 16, 2001 | P7OVQ 42 | 80 | 20 | (re-do) | 0 | 0 | 0 | 20 |
| | Dec. 14, 2001 | P7OVQ 48 | 80 | 20 | (re-do) | 0 | 0 | 0 | 20 |
| | Nov. 02, 2001 | P7OVQ 53 | 80 | 20 | (re-do) | 0 | 0 | 0 | 20 |
| | Nov. 30, 2001 | P7OVQ 56 | 80 | 20 | (re-do) | 0 | 0 | 0 | 20 |
| | Jan. 11, 2002 | (+) Control | | | | | | | |
| | Jan. 25, 2002 | M62 | 2560 | 160 | 2560 | | 6400 | 2560 | 640 |
| | Feb. 08, 2002 | Positive control S193 (1 mg/ml) | | | | | | | |
| | Apr. 19, 2002 | Positive control | | | | | | | |
| | | Positive control | | | | 2560 | | | |
| | | Positive control | | | | | | | 2560 |
| | | Positive control | | | | | | | |
| | | | Jun. 18, 2002 | Jun. 18, 2002 | | | | | |
| Patient 8 | Oct. 23, 2001 | P7OVQ 29 | 0 | 0 | | | | | |
| | Oct. 30, 2001 | P7OVQ 38 | 0 | 0 | | | | | |
| | Nov. 06, 2001 | P7OVQ 43 | 0 | 0 | | | | | |

| | Jun. 25, 2002 | Jun. 25, 2002 |
|---|---|---|
| | 2560 | 2560 |
| | 20 | 0 |
| | 160 | 160 |
| | 80 | 160 |
| | 80 | 80 |
| | 80 | 40 |
| | 80 | 80 |
| | 2560 | 2560 |

Protocol 00-106:
Pilot Phas Trial: Vaccination of Patients Who Have Ovarian, Fallopian Tube or Peritoneal Cancer with A Polyvalent Vaccine-KLH Conjugate + QS-21

| | | Vaccine: | 10ug GM2 | 10ug Globo-H | 10ug LeY | 3ug MucIG5 | 3ug Tn(c) | 3ug S-Tn(c) | 3ug TF(c) |
|---|---|---|---|---|---|---|---|---|---|
| | Dec. 04, 2001 | P7OVQ 51 | 0 | 0 | | | | | |
| | Jan. 29, 2002 | P7OVQ 54 | 40 | 0 | | | | | |
| | | OFF TRIAL | | | | | | | |
| | | (+) Control M62 | 2560 | 640 | | | | | |
| | | | Jun. 18, 2002 | Jun. 18, 2002 | | | | | |
| Patient 9 | Nov. 06, 2001 | P7OVQ 34 | 0 | 0 | | | | | |
| | Nov. 13, 2001 | P7OVQ 40 | 1280 | 80 | | | | | |
| | Nov. 20, 2001 | P7OVQ 45 | 320 | 80 | | | | | |
| | Dec. 18, 2001 | P7OVQ 55 | 320 | 40 | | | | | |
| | Jan. 29, 2002 | P7OVQ 58 | 160 | 80 | | | | | |
| | Feb. 12, 2002 | P7OVQ 60 | 160 | 80 | | | | | |
| | Feb. 26, 2002 | P7OVQ 64 | 40 | 80 | | | | | |
| | May 09, 2002 | (+) Control M62 | 2560 | 320 | | | | | |
| | | | Jun. 13, 2002 | Jun. 13, 2002 | Jun. 27, 2002 | Jun. 19, 2002 | Jun. 21, 2002 | Jun. 21, 2002 | Jun. 24, 2002 |
| Patient 10 | Nov. 20, 2001 | P7OVQ 37 | 0 | 0 | 0 | (re-do) | 0 | 0 | 0 |
| | Nov. 27, 2001 | P7OVQ 46 | 320 | 60 | 320 | (re-do) | 0 | 20 | 20 |
| | Dec. 04, 2001 | P7OVQ 50 | 320 | 320 | 320 | (re-do) | 0 | 20 | 20 |
| | Jan. 01, 2002 | pt no show | — | — | — | — | — | — | — |
| | Feb. 12, 2002 | P7OVQ 59 | 40 | 160 | 80 | (re-do) | 0 | 20 | 20 |
| | Mar. 12, 2002 | pt no show | — | — | — | — | — | — | — |
| | May 21, 2002 | pt no show | — | — | — | — | — | — | — |
| | | (+) Control M62 | 2560 | 160 | | 2560 | 6400 | 2560 | 2560 |
| | | Positive control S193 (1 mg/ml) | | | 1280 | | | | |
| | | Positive control | | | | | | 640 | |
| | | Positive control | | | | | | | 2560 |
| | | | | | | | Jun. 25, 2002 | Jun. 25, 2002 | |
| | | Positive control | | | | | 0 | 0 | |
| | | Positive control | | | | | 160 | 80 | |
| | | Positive control | | | | | 80 | 640 | |
| | | Positive control | | | | | 40 | 320 | |
| | | Positive control | | | | | — | — | |
| | | Positive control | | | | | 2560 | 2560 | |

Protocol 00-106:
Pilot Phas Trial: Vaccination of Patients Who Have Ovarian, Fallopian Tube or Peritoneal Cancer with A Polyvalent Vaccine-KLH Conjugate + QS-21

| | Vaccine: | 10ug GM2 | 10ug Globo-H | 10ug LeY | 3ug MucIG5 | 3ug Tn(c) | 3ug S-Tn(c) | 3ug TF(c) | | |
|---|---|---|---|---|---|---|---|---|---|---|
| | | Jun. 12, 2002 | Jun. 12, 2002 | Jun. 27, 2002 | Jun. 19, 2002 | Jun. 21, 2002 | Jun. 24, 2002 | Jun. 24, 2002 | Jun. 25, 2002 | Jun. 25, 2002 |
| Patient 11 Mar. 07, 2001 | P7OVQ 1 | 0 | 0 | 0 | 0 | 0 | 0 | 20 | 20 | 0 |
| Feb. 05, 2002 | P7OVQ 57 | 0 | 0 | 0 | 0 | 0 | 0 | 0 | 20 | 0 |
| Mar. 05, 2002 | P7OVQ 61 | 0 | 20 | 0 | 0 | 0 | 0 | 0 | 40 | 60 |
| Feb. 19, 2002 | OFF TRIAL | | | | | | | | | |
| Mar. 19, 2002 | | | | | | | | | | |
| | (+) Control M62 | 2560 | | | | | | | | |
| | Positive control S193 (1 mg/ml) | | 640 | | | | | | | |
| | Positive control | | | 2560 | | | | | | |
| | Positive control | | | | 2560 | | | | | |
| | Positive control | | | | | 6400 | | | | |
| | Positive control | | | | | | 2560 | | | |
| | Positive control | | | | | | | 640 | | |
| | Positive control | | | | | | | 2560 | 2560 | 2560 |

* Patient received one vaccine before protocol hold, restarted-1 year later

| | | | ELISA GM2 (10 mcg) (March 2002) | | ELISA MUC-1-1 5G (3 mcg) (March 2002) | | ELISA LeY Ceramide (10 mcg) (April 2002) | | ELISA Globo H Ceramide (10 mcg) (May 2002) | | ELISA Tf (3 mcg) (May 2002) | | ELISA dOSM for Tn (3 mcg) (August 2002) | | ELISA sTn (3 mcg) | |
|---|---|---|---|---|---|---|---|---|---|---|---|---|---|---|---|---|
| Patient # | Vaccine Date | Sample Date | Serology Top | IgG | IgM | IgG | IgM | IgG | IgM | IgG | IgM | IgG | IgM | IgG | IgM | IgG | IgM |
| Patient 1 | Jan. 16, 2002 | Jan. 16, 2002 | P7BRQ4 | 20 | 0 | 0 | 0 | 0 | 0 | 0 | 0 | 0 | 20 | | | | |
| | Jan. 23, 2002 | Jan. 23, 2002 | P7BRQ9 | 0 | 0 | 0 | 0 | 0 | 0 | 0 | 0 | 0 | 40 | | | | |
| | Jan. 30, 2002 | Jan. 30, 2002 | P7BRQ11 | 0 | 0 | 0 | 0 | 0 | 0 | 0 | 20 | 0 | 40 | | | | |
| | Feb. 13, 2002 | Feb. 13, 2002 | P7BRQ19 | 0 | 0 | 40 | 80 | 0 | 0 | 0 | 20 | 320 | 640 | | | | |
| | Feb. 27, 2002 | Feb. 27, 2002 | P7BRQ28 | 0 | 0 | 20 | 80 | 0 | 0 | 0 | 0 | 80 | 1280 | | | | |
| | | Mar. 13, 2002 | P7BRQ37 | 0 | 40 | 40 | 80 | 0 | 0 | 0 | 20 | 160 | 1280 | | | | |
| | | Apr. 10, 2002 | P7BRQ44 | 0 | | 80 | 320 | 0 | 0 | 0 | 20 | 80 | 1280 | | | | |
| | May 22, 2002 | May 22, 2002 | P7BRQ62 | | | | | | | | | 40 | 640 | | | | |
| | | Jun. 05, 2002 | P7BRQ67 | | | | | | | | | | | | | | |
| Controls | | | (M62) | 320 | >2560 | | | | | | | | | | | | |
| | | | (MCG170) | | | 320 | 2560 | | | | | | | | | | |
| | | | (LeYM12) | | | 160 | 2560 | 20 | 80/160 | | | | | | | | |
| | | | Mono Ab (S193) | | | | | 1280 | | | | | | | | | |
| | | | (GB81) | | | | | | | 0 | 320 | | | | | | |
| | | | Mono Ab (VK9) | | | | | | | 5120 | | | | | | | |
| | | | (P7BRQ17) | | | | | | | | | 320 | >2560 | | | | |
| | | | (slovin lab wk7) | | | | | | | | | | | | | | |
| Patient 2 | Jan. 16, 2002 | Jan. 16, 2002 | P7BRQ5 | 0 | 0 | 0 | 0 | 0 | 0 | 0 | 0 | 20 | 20 | | | | |
| | Jan. 23, 2002 | Jan. 23, 2002 | P7BRQ8 | 0 | 0 | 0 | 0 | 0 | 0 | 0 | 40 | 0 | 40 | | | | |
| | Jan. 30, 2002 | Jan. 30, 2002 | P7BRQ12 | 0 | 0 | 80 | 160 | 0 | 0 | 0 | 2560 | 160 | 640 | | | | |
| | Feb. 13, 2002 | Feb. 13, 2002 | P7BRQ20 | 0 | 80 | 40 | 20 | 0 | 0 | 0 | 640 | 160 | 1280 | | | | |
| | Feb. 27, 2002 | Feb. 27, 2002 | P7BRQ27 | 0 | 160 | 80 | 20 | 0 | 0 | 0 | 640 | 160 | 1280 | | | | |
| | | Mar. 13, 2002 | P7BRQ36 | | | 80 | 80 | 0 | 0 | 0 | 320 | 320 | 640 | | | | |
| | | Apr. 10, 2002 | P7BRQ46 | | | | | | | | 80 | 160 | 640 | | | | |
| | May 22, 2002 | May 22, 2002 | P7BRQ61 | | | | | | | | | 160 | 640 | | | | |
| | | Jun. 05, 2002 | P7BRQ68 | | | | | | | | | | | | | | |
| Controls | | | (P7BRQ17) (hexavalent) | 320 | >2560 | | | | | | | | | | | | |
| | | | (P7BRQ16) | | | 80 | >2560 | | | | | | | | | | |
| | | | (LeYM12) | | | 640 | 320 | 0 | 150 | | | | | | | | |
| | | | Mono Ab (S193) | | | | | 1280 | | | | | | | | | |
| | | | (GB81) | | | | | | | 0 | 320 | | | | | | |
| | | | Mono Ab (VK9) | | | | | | | 5120 | | | | | | | |
| | | | (P7BRQ17) | | | | | | | | | 320 | >2560 | | | | |
| | | | (slovin lab wk7) | | | | | | | | | | | | | | |

Protocol # 01-019: Serological analysis of Breast cancer patient vaccinated with hexavalent vaccine Protocol # 01-019: Serological analysis of Breast cancer patient vaccinated with hexavalent vaccine

| Patient Name | Vaccine Date | Sample Date | Serology Top | ELISA GM2 (10 mcg) (March 2002) IgG | IgM | ELISA MUC-1-1 5G (3 mcg) (March 2002) IgG | IgM | ELISA LeY Ceramide (10 mcg) (April 2002) IgG | IgM | ELISA Globo H Ceramide (10 mcg) (May 2002) IgG | IgM | ELISA Tf (10 mcg) (May 2002) IgG | IgM | ELISA dOSM for Tn (3 mcg) (June 2002) IgG | IgM | ELISA sTn (3 mcg) IgG | IgM |
|---|---|---|---|---|---|---|---|---|---|---|---|---|---|---|---|---|---|
| Patient 3 | Jan. 07, 2002 | Jan. 07, 2002 | P7BRQ1 | 0 | 0 | 0 | 0 | 0 | 0 | 0 | 0 | 0 | 0 | 0 | 40 | | |
| | Jan. 14, 2002 | Jan. 14, 2002 | P7BRQ3 | 0 | 0 | 0 | 0 | 0 | 0 | 0 | 0 | 0 | 0 | 0 | 20 | | |
| | Jan. 21, 2002 | Jan. 21, 2002 | P7BRQ7 | 0 | 20 | 80 | 320 | 20 | 0 | 20 | 320 | 0 | 320 | 80 | 160 | | |
| | Feb. 04, 2002 | Feb. 04, 2002 | P7BRQ17 | 0 | 0 | 80 | 2560 | 40 | 0 | 640 | 640 | 320 | 2560 | 320 | 320 | | |
| | Feb. 18, 2002 | Feb. 18, 2002 | P7BRQ23 | | | 80 | 640 | 20 | 0 | 320 | 320 | 1280 | 1280 | 640 | 160 | | |
| | | Mar. 04, 2002 | P7BRQ30 | | | 80 | 320 | 0 | 0 | 320 | 1280 | 1280 | 640 | 160 | 160 | | |
| | | Apr. 01, 2002 | P7BRQ41 | | | | 80 | 0 | 0 | 80 | 320 | 320 | 320 | | | | |
| | May 13, 2002 | May 13, 2002 | P7BRQ57 | | | | | 0 | 0 | 20 | 20 | 160 | | | | | |
| | | May 27, 2002 | P7BRQ63 | | | | | 0 | 0 | 20 | | | | | | | |
| Controls | | | (P7BRQ17) (hexavalent) | 320 | | | | | | | | | | | | | |
| | | | (P7BRQ16) (LeYM12) | | >2560 | | | 1280 | 160 | | | | | | | | |
| | | | Mono Ab (SJ93) (GB81) | | | 160 | 1280 | | | | | | | | | | |
| | | | Mono Ab (VK9) (P7BRQ17) | | | 320 | 2560 | | | 0 | 320/640 | | | | | | |
| | | | (slovin lab wk7) | | | | | | | 0 | 1280/2560 | 320 | 320 | | | | |
| | May 13, 2002 | | | | | | | | | | | | 2560 | | | | |

| Patient Name | Vaccine Date | Sample Date | Serology Top | ELISA GM2 (10 mcg) (March 2002) IgG | IgM | ELISA MUC-1-1 5G (3 mcg) (March 2002) IgG | IgM | ELISA LeY Ceramide (10 mcg) (April 2002) IgG | IgM | ELISA Globo H Ceramide (10 mcg) (May 2002) IgG | IgM | ELISA Tf (10 mcg) (May 2002) IgG | IgM | ELISA dOSM for Tn (3 mcg) (June 2002) IgG | IgM | ELISA sTn (3 mcg) IgG | IgM |
|---|---|---|---|---|---|---|---|---|---|---|---|---|---|---|---|---|---|
| Patient 4 | Jan. 14, 2002 | Jan. 14, 2002 | P7BRQ2 | 0 | 0 | 0 | 0 | 0 | 40 | 0 | 20 | 0 | 0 | 40 | | | |
| | Jan. 21, 2002 | Jan. 21, 2002 | P7BRQ6 | 0 | 0 | 0 | 0 | 0 | 20 | 20 | 80 | 0 | 0 | 20 | | | |
| did not come in | Jan. 28, 2002 | Jan. 28, 2002 | P7BRQ10 | 0 | 0 | 80 | 0 | 0 | 40 | 0 | 320 | 20 | 20 | 160 | | | |
| | | Feb. 11, 2002 | P7BRQ16 | 0 | 0 | 640 | 320 | 0 | 1280 | 0 | 640/1280 | 40 | 40 | 320 | | | |
| | Feb. 25, 2002 | Feb. 25, 2002 | P7BRQ26 | 0 | 0 | 160 | 40 | 0 | 320 | 0 | 320 | 40 | 160 | 640 | | | |
| | | Mar. 11, 2002 | P7BRQ34 | 0 | 0 | 160 | 20 | 0 | 640 | 80 | 320 | 160 | 160 | 160 | | | |
| | | Apr. 08, 2002 | | | | | | | | | | | | | | | |
| | | Apr. 15, 2002 | P7BRQ47 | | | 320 | 80 | 0 | 320 | 0 | 160 | 160 | 160 | 160 | | | |
| | May 20, 2002 | May 20, 2002 | P7BRQ58 | | | | | | | 80 | 40 | 320 | | | | | |
| | | Jun. 03, 2002 | P7BRQ65 | | | | | | | | 40 | | | | | | |
| Controls | | | (P7BRQ17) (hexavalent) | 320 | | | | | | | | | | | | | |
| | | | (P7BRQ16) (LeYM12) | | >2560 | | | | 160 | | | | | | | | |
| | | | Mono Ab (SJ93) (GB81) | | | 320 | >2560 | | | | | | | | | | |
| | | | Mono Ab (VK9) (P7BRQ17) | | | 160 | >2560 | | | 20 | 320/640 | | | | | | |
| | | | (slovin lab wk7) | | | | | | | 0 | 1280/2560 | 320 | 320 | >2560 | | | |

Protocol # 01-019: Serological analysis of Breast cancer patient vaccinated with hexavalent vaccine

| | | | ELISA GM2 (10 mcg) (April 2002) | | ELISA MUC-1-1 5G (3 mcg) (April 2002) | | ELISA LeY Ceramide (10 mcg) (April 2002) | | ELISA Globo H Ceramide (10 mcg) (May 2002) | | ELISA Tf (10 mcg) (May 2002) | | ELISA dOSM for Tn (3 mcg) (June 2002) | | ELISA sTn (3 mcg) | |
|---|---|---|---|---|---|---|---|---|---|---|---|---|---|---|---|---|
| | | Serology Top | IgG | IgM | IgG | IgM | IgG | IgM | IgG | IgM | IgG | IgM | IgG | IgM | IgG | IgM |
| Patient 5 | Feb. 06, 2002 | P7BRQ15 | 0 | 0 | 0 | 0 | 0 | 0 | 0 | 0 | 0 | 0 | 0 | 0 | | |
| | Feb. 13, 2002 | P7BRQ22 | 0 | 0 | 0 | 20 | 0 | 0 | 0 | 0 | 0 | 0 | 0 | 0 | | |
| | Feb. 20, 2002 | P7BRQ25 | 0 | 0 | 0 | 0 | 0 | 0 | 0 | 0 | 0 | 20 | 0 | 40 | | |
| | Mar. 06, 2002 | P7BRQ33 | 0 | 0 | 40 | 40 | 0 | 0 | 0 | 0 | 20 | 0 | 0 | 40 | | |
| | Mar. 20, 2002 | P7BRQ38 | 0 | 0 | 20 | 40 | 0 | 0 | 0 | 0 | 0 | 0 | 0 | 40 | | |
| | Apr. 03, 2002 | P7BRQ42 | 0 | 0 | 160 | 40 | 0 | 0 | 0 | 0 | 0 | 40 | 40 | 40 | | |
| | May 01, 2002 | P7BRQ51 | | | | | | | | | | 20 | | 20 | | |
| | Jun. 12, 2002 | P7BRQ71 | | | | | | | | | | | | | | |
| | Jun. 26, 2002 | | | | | | | | | | | | | | | |
| Controls | | (P7BRQ17) (hexavalent) | 320 | >2560 | 80 | 160 | 20 | | | | | | | | | |
| | | (P7BRQ16) (LeYM12) | | | 640 | 320 | 1280 | | | | | | | | | |
| | | Mono Ab (SJ93) (GB81) | | | | | | 160 | 320/640 | | | | | | | |
| | | Mono Ab (VK9) (P7BRQ17) | | | | | | | 1280/2560 | | 320 | 320 | >2560 | | | |
| | | (solvin tab wk7) | | | | | | | | | 320 | 320 | 1280 | | | |
| Patient 6 | Feb. 06, 2002 | P7BRQ14 | 0 | 20 | 0 | 0 | 20 | 0 | 0 | 0 | 0 | 0 | 0 | 0 | | |
| | Feb. 13, 2002 | P7BRQ18 | 0 | 20 | 0 | 0 | 0 | 0 | 0 | 0 | 0 | 0 | 0 | 0 | | |
| | Feb. 20, 2002 | P7BRQ24 | 0 | 40 | 80 | 80 | 0 | 0 | 0 | 160 | 160 | 160 | 80 | | | |
| | Mar. 06, 2002 | P7BRQ31 | 0 | 20 | 320 | 320 | 0 | 0 | 0 | 160 | 160 | 160 | 320 | 320 | | |
| | Mar. 20, 2002 | P7BRQ39 | 0 | 20 | 160 | 320 | 0 | 0 | 0 | 80 | 40 | 40 | 160 | 160 | | |
| | Apr. 03, 2002 | P7BRQ43 | | | 320 | 40 | 0 | | | 40 | 40 | 160 | 160 | | | |
| | May 01, 2002 | P7BRQ52 | | | | | | | | 40 | 40 | 320 | 320 | | | |
| | Jun. 12, 2002 | P7BRQ70 | | | | | | | | | | | | | | |
| | Jun. 26, 2002 | | | | | | | | | | | | | | | |
| Controls | | (P7BRQ17) (hexavalent) | 320 | >2560 | 80 | 640 | 0 | | | | | | | | | |
| | | (P7BRQ16) (LeYM12) | | | 640 | 320 | 1280 | | | | | | | | | |
| | | Mono Ab (SJ93) (GB81) | | | | | | 80/160 | 320/640 | | | | | | | |
| | | Mono Ab (VK9) (P7BRQ17) | | | | | | | 1280/2560 | | 320 | 320 | 2560 | | | |
| | | (solvin tab wk7) | | | | | | | | | 320 | 320 | 1280 | | | |

| Patient Name | Vaccine Date | Sample Date | Serology Top | IgG | IgM | IgG | IgM | IgG | IgM | IgG | IgM | IgG | IgM | IgG | IgM | IgG | IgM |
|---|---|---|---|---|---|---|---|---|---|---|---|---|---|---|---|---|---|
| Patient 7 | Feb. 27, 2002 | Feb. 27, 2002 | P7BRQ29 | 0 | 0 | 0 | 0 | 0 | 0 | 0 | 0 | 0 | 0 | 20 | 20 | | |
| | Mar. 06, 2002 | Mar. 06, 2002 | P7BRQ32 | 0 | 0 | 0 | 0 | 0 | 0 | 0 | 0 | 0 | 0 | 0 | 0 | | |
| | Mar. 13, 2002 | Mar. 13, 2002 | P7BRQ35 | 0 | 20 | 20 | 320 | 0 | 0 | 0 | 0 | 320 | 320 | 160 | 160 | | |
| | | Mar. 27, 2002 | P7BRQ40 | 0 | 40 | 320 | 320 | 0 | 0 | 0 | 0 | 640/1280 | | 160 | 160 | | |

TABLE -continued

Protocol # 01-019: Serological analysis of Breast cancer patient vaccinated with hexavalent vaccine

|  | Date | Sample | | | | | | | |
|---|---|---|---|---|---|---|---|---|---|
|  | Apr. 10, 2002 | P7BRQ45 | 0 | 80 | 320 | 640 | 0 | 0 | 640 | 80 |
|  | Apr. 24, 2002 | P7BRQ49 | 0 | 60 | 160 | 320 | 0 | 0 | 1280 | 80 |
|  | May 22, 2002 | P7BRQ60 | | | | | 0 | 0 | 640 | 80 |
| Controls | Jul. 03, 2002 | | 320 | >2560 | | | | | | |
|  |  | (P7BRQ17) (hexavalent) |  |  | 80 | 640 | 0 | 1280 |  |  |
|  |  | (P7BRQ16) (LeYM12) |  |  | 640 | 320 | 0 | 160 |  |  |
|  |  | Mono Ab (SJ93) (GB81) |  |  |  |  | 1280 |  |  |  |
|  |  | Mono Ab (VK9) (P7BRQ17) |  |  |  |  | 20 | 320 | 640 | 2560 |
|  |  | (slovin tab wk7) |  |  |  |  | 0 | 1280/2560 | 640 | 1280 |
| Patient 8 | Apr. 22, 2002 | P7BRQ48 | (June 2002) | | | | | | | |
|  | Apr. 29, 2002 | P7BRQ53 | | | | | | | | |
|  | May 06, 2002 | P7BRQ54 | | | | | | | | |
|  | May 20, 2002 | P7BRQ59 | | | | | | | | |
|  | Jun. 03, 2002 | P7BRQ85 | | | | | | | | |
|  | Jun. 17, 2002 | P7BRQ72 | | | | | | | | |
|  | Jul. 15, 2002 | | | | | | | | | |
|  | Aug. 26, 2002 | | (June 2002) | | | (July 2002) | | (July 2002) | | |
| Controls | Sep. 09, 2002 | | | | | | | | | |
|  |  | (P7BRQ17) (hexavalent) | | | | | | | | |
|  |  | (P7BRQ16) (LeYM12) | | | | | | | | |
|  |  | Mono Ab (SJ93) (GB81) | | | | | | | | |
|  |  | Mono Ab (VK9) (P7BRQ17) | | | | | | | | |
|  |  | (slovin tab wk7) | | | | | | | | |
| Patient 9 | Apr. 29, 2002 | P7BRQ50 | | | | | | | | |
|  | May 06, 2002 | P7BRQ55 | | | | | | | | |
|  | May 13, 2002 | P7BRQ56 | | | | | | | | |
|  | May 27, 2002 | P7BRQ64 | | | | | | | | |
|  | Jun. 10, 2002 | P7BRQ69 | | | | | | | | |
|  | Jun. 24, 2002 | | | | | | | | | |
|  | Jul. 22, 2002 | | | | | | | | | |
|  | Sep. 02, 2002 | | | | | | | | | |
|  | Sep. 16, 2002 | | | | | | | | | |

-continued

Protocol # 01-019: Serological analysis of Breast cancer patient vaccinated with hexavalent vaccine Controls
*(P7BRQ17)*
*(hexavalent)*
*(P7BRQ16)*
*(LeTM12)*
*Mono Ab (S193)*
*(GB81)*
*Mono Ab (VK9)*
*(P7BRQ17)*
*(slovin tab wk7)*

Notes
Monoclonals:
Dilutions VK9 1:200; S193 1:400
DOSM
Tested positive by ELISA with Monoclonals 5F4 and HB-TN1.
OSM
Tested positive by ELISA with Monoclonals 5F4, B72.3, and HB-TN1.
Shaded region denotes Pre sera (week 1)
All samples were tested in duplicate.
for patients Lewis and Smith, Lewis Y plates were coated at 0.3, future plates will be coated at 0.2,
Italics controls previously tested as positive.

| Hexavalent Pilot study, protocol number #00-64, ELISA tested against TF(c)-HSA | | | | | | | | | | | |
|---|---|---|---|---|---|---|---|---|---|---|---|
| | | | Vaccination | | | | | | | | |
| Ag | Patient | Ab | 1 wk1 | 2 2 | 3 3 | 4 7 | 12 | 19 | 5 21 | 31 | 33 |
| TFc HSA | 1 | IgM | 40 | 40 | 40 | 40 | >1280 | 40 | 40 | 40 | 40 |
| | | IgG | 20 | 20 | >1280 | 320 | 80 | 80 | 80 | 160 | 320 |
| | 2 | IgM | NMA | 80 | 160 | 160 | 80 | 40 | 40 | 20 | 20 |
| | | IgG | 10 | NMA | 10 | 40 | 80 | NMA | NMA | 20 | 40 |
| | 3 | IgM | | 40 | | | | | | | |
| | | IgG | | NMA | | | | | | | |
| | 4 | IgM | 40 | 20 | 320 | 80 | 60 | 80 | NMA | | |
| | | IgG | NMA | NMA | 640 | 80 | 40 | 160 | 320 | | |
| | 5 | IgM | NMA | 20 | 160 | 20 | | | | | |
| | | IgG | 10 | NMA | 10 | 20 | | | | | |
| | 6 | IgM | | 40 | 640 | 640 | 640 | 160 | 80 | 80 | 160 |
| | | IgG | | 640 | >1280 | >1280 | >1280 | >1280 | >1280 | >1280 | >1280 |
| | 7 | IgM | NMA | 40 | 80 | 640 | 160 | 60 | 40 | 80 | 80 |
| | | IgG | 10 | 320 | NMA | NMA | 40 | 20 | 80 | 20 | 80 |
| | 8 | IgM | NMA | NMA | 160 | 160 | | | | | |
| | | IgG | NMA | NMA | 10 | 80 | | | | | |
| | 9 | IgM | NMA | NMA | NMA | 20 | NMA | NMA | NMA | NMA | |
| | | IgG | NMA | NMA | 40 | NMA | 640 | 80 | >1280 | 160 | |
| | 10 | IgM | NMA | 10 | 160 | 160 | | | | | |
| | | IgG | NMA | NMA | 40 | 20 | | | | | |
| | 11 | IgM | | 20 | | | | | | | |
| | | IgG | | NMA | | | | | | | |
| | 12 | IgM | 10 | 40 | 160 | >1280 | 80 | 640 | 80 | 20 | 160 |
| | | IgG | NMA | NMA | NMA | NMA | >640 | 20 | 40 | 40 | 80 |
| | 13 | IgM | | NMA | | | | | | | |
| | | IgG | | NMA | | | | | | | |
| | 14 | IgM | 20 | 80 | 40 | 80 | 80 | 40 | 40 | 160 | 160 |
| | | IgG | NMA | 40 | 160 | >1280 | 640 | 80 | 80 | 80 | 160 |
| | 15 | IgM | NMA | NMA | 20 | 80 | 40 | 40 | | | |
| | | IgG | NMA | NMA | 10 | 40 | 40 | 40 | | | |
| | 16 | IgM | 20 | 80 | >1280 | | | | | | |
| | | IgG | 10 | 10 | 80 | | | | | | |
| | 17 | IgM | NMA | 10 | NMA | 40 | 40 | 40 | 40 | 40 | 160 |
| | | IgG | NMA | NMA | | 40 | 40 | 80 | 40 | 20 | 40 |
| | 18 | IgM | 40 | 20 | 80 | 640 | 40 | 80 | 80 | 20 | 80 |
| | | IgG | NMA | NMA | NMA | 40 | 160 | 40 | 640 | 40 | 40 |

Positive Controls: IgM (19) 1:1280
IgG (7) 1:640
(−) Human AB Serum

As from Oct. 19, 2001 end pt. Titers: (+) IgM: 640
IgG: 640
(−) IgM: NMA
IgG: NMA

| Hexavalent Pilot study, protocol # 00-64 ELISA against glycosylated MUC1-1 (5 sites) | | | | | | | | | | | |
|---|---|---|---|---|---|---|---|---|---|---|---|
| | Vaccination | | | 1 | 2 | 3 | 4 | | 5 | | |
| Ag | Patient | Number | Ab | wk1 | 2 | 3 | 7 | 12 | 19 | 21 | 31 |
| MUC 1-1G5 32mer | | 1 | IgM | NMA | 40 | >1280 | >1280 | >1280 | >1280 | >1280 | >1280 |
| | | | IgG | NMA | NMA | 80 | 160 | >1280 | 640 | >1280 | >1280 |
| | | 2 | IgM | NMA | NMA | | 640 | 10 | NMA | 10 | 20 |
| | | | IgG | NMA | NMA | 10 | 40 | 40 | 20.00 | 40 | 160 |
| | | 3 | IgM | | 20 | 640 | | | | | |
| | | | IgG | | NMA | 40 | | | | | |
| | | 4 | IgM | NMA | NMA | 320.00 | >1280 | >1280 | >1280 | 640 | 640 |
| | | | IgG | NMA | NMA | 10 | 320 | 160 | >1280 | >1280 | >1280 |
| | | 5 | IgM | 10 | 40 | >1280 | | >1280 | | | |
| | | | IgG | NMA | NMA | 160 | | >1280 | | | |
| | | 6 | IgM | | NMA | 320 | >1280 | 320 | 320 | 160 | 80 |
| | | | IgG | | NMA | 160 | >1280 | 320 | 160 | 160 | 160 |
| | | 7 | IgM | NMA | NMA | 40 | 640 | 640 | 80 | 80 | 40 |
| | | | IgG | NMA | NMA | 640 | >1280 | >1280 | >1280 | >1280 | >1280 |
| | | 8 | IgM | NMA | NMA | 160 | | | | | |
| | | | IgG | NMA | NMA | 10 | | | | | |
| | | 9 | IgM | NMA | NMA | 40 | 160 | 80 | 20 | 20 | 10 |
| | | | IgG | NMA | NMA | NMA | 40 | 20 | 10 | 80 | 40 |
| | | 10 | IgM | NMA | NMA | | | | | | |
| | | | IgG | NMA | NMA | | | | | | |

-continued

| | | | | | | | | | |
|---|---|---|---|---|---|---|---|---|---|
| 11 | IgM | NMA | NMA | 10 | 40 | 20 | 160 | 160 | 80 |
| | IgG | NMA | NMA | 10 | 320 | 160 | 40 | 40 | 20 |
| 12 | Igm | 40 | 40 | | | | | | |
| | IgG | NMA | NMA | | | | | | |
| 13 | Igm | NMA | NMA | 20 | 80 | 80 | 320 | 320 | 160 |
| | IgG | NMA | NMA | 20 | 20 | 40 | 320 | 320 | 160 |
| 14 | Igm | 80 | 20 | 160 | 160 | 40 | 40 | | |
| | IgG | NMA | NMA | NMA | NMA | 40 | 20 | | |
| 15 | Igm | NMA | NMA | 640 | 640 | 640 | 10 | 10 | 10 |
| | IgG | NMA | NMA | 640 | 640 | 640 | 160 | 80 | 80 |
| 16 | Igm | NMA | 20 | | | | | | |
| | IgG | NMA | 20 | | | | | | |
| 17 | IgM | NMA | 20 | 320 | 160 | 40 | 640 | 320 | 80 |
| | IgG | NMA | NMA | 10 | 80 | 640 | 40 | 640 | 160 |

Positive Controls: (7) IgM 1: 2560
IgG 1: 2560    Oct. 22, 2001
(−) AB Sera

Controls as of Oct. 15, 2001:
(+) Igm: >1280
IgG: >1280
(−) IgM: NMA
IgG: NMA

Fourth Series of Experiments

Polyvalent Conjugate Vaccine for Cancer

Preliminary Data of Vaccination of High Risk Breast Cancer (BC) Patients (Pts) with a Heptavalent Antigen—Keyhole Limpet Hemocyanin (KLH) Conjugate Plus the Immunologic Adjuvant QS-21.

We have previously shown that following vaccination with single antigen (Ag)-KLH conjugates plus QS-21, the majority of BC pts generate specific antibody (AB) titers. (Clin Ca Res 6:1693, 2000; PNAS 98(6):3270, 2001; Proc ASCO 16:439a, 1997, 18:439a, 1999, 20:271a, 2001) Single Ag's tested have included MUC-1 (various peptide lengths), sTn clustered (c), GloboH and GM2. In an effort to improve and broaden the immune response, we treated BC pts with seven Ag's: 10 mcg each of GM2, GloboH, Lewis$^y$; and 3 mcg each of TF(c), sTn(c), Tn(c) and glycosylated MUC-1, (32 amino acid (aa) sequence, glycosylated at 5 sites per 20 aa tandem repeat). Each Ag was conjugated to KLH and mixed with 100 mcg of QS-21. Heptavalent vaccines were administered subcutaneously during weeks 1, 2, 3, 7, and 19. We treated ten patients: median age 48 years (range 43-63 yrs); Stage 1V=3, Stage 2 with ≧4 positive nodes=7. Nine pts have completed immunization. Toxicity was limited to transient grade 2 local skin reactions and grade 1-2 flu-like symptoms. IgM and IgG AB titers were considered positive for each antigen if there was at least an eightfold increase above baseline more than once, during weeks 1-19. Antibody responses are tabulated. (table) MUC1 and TF(c) seem most immunogenic. Flow cytometric analysis (FACS) was obtained pre and post therapy to detect binding of IgM and IgG AB against MCF-7 tumor cells. A positive FACS was defined as at least a threefold increase above baseline and was observed in 6/9 patients for IgM and 0/9 for IgG. Further analyses are ongoing. Our next cohort will evaluate the same antigens conjugated to KLH but with GP-100 as the immunologic adjuvant.

Number of pts with positive AB response/Number of pts evaluable

| Ag | GM2 | Ley | MUC1 | TF(c) | sTn(c) | Tn(c) | GloboH |
|---|---|---|---|---|---|---|---|
| IgM | 2/9 | 1/9 | 8/9 | 8/9 | 4/9 | 7/9 | 6/9 |
| IgG | 0/9 | 1/9 | 8/9 | 8/9 | 1/9 | 0/9 | 0/9 |

Objectives
  Determine immune response against seven antigens and cell lines expressing these antigens
  Evaluate toxicity
Background
  Preclinical data demonstrates that conjugation of an antigen with keyhole limpet hemocyanin (KLH) and addition of the immune adjuvant QS-21 augments immunogenicity (Cancer Immunol Immunother 41:185, 1985; Cancer Res 56:3315, 1996)
  Following vaccination with single antigen-KLH conjugates plus QS-21, most breast cancer patients generated IgM and IgG antibodies against the immunizing antigens (Clin Ca Res 6:1693, 2000; PNAS 98(6):3270, 2001; Proc ASCO 16:439a, 1997, 18:439a. 1999, 20:271a, 2001)
  These single antigens have included MUC-1 (various peptide lengths), sTn clustered (c), GloboH and GM2
  To broaden the immune response, seven antigens were individually conjugated to KLH and mixed with QS-21 to construct this heptavalent vaccine
Vaccine Components
  Antigens
    Protein: glycosylated MUC-1 (32aa peptide)
    Gangliosides: GM2, GloboH
    Carbohydrates: LewisY, sTn(c), Tn(c), TF(c)
  Immunogenic protein carrier
    KLH (by the following methods of conjugation):
      MBS (m-maleimidobenzoyl-N-hydroxysuccinimide ester) linker for TF(c), sTn(c), Tn(c), and MUC-1
      MMCCH (4-[4-N-maleimidomethyl] cyclohexane-1-carboxyl hydrazide) linker for GloboH and Le$^y$
      Direct reductive amination for GM2
  Immunologic Adjuvant
    QS-21 (purified saponin fraction of tree bark)
Vaccine Components

| Antigens* | Doses |
|---|---|
| GM2 | 10 mcg |
| MUC-1 | 3 mcg |
| LewisY | 10 mcg |
| GloboH | 10 mcg |

-continued

| | Doses |
|---|---|
| TF(c) | 3 mcg |
| Tn(c) | 3 mcg |
| sTn(c) | 3 mcg |
| Adjuvant | |
| QS-21 | 100 mcg |

*(each conjugated to KLH)

Treatment and Evaluation Plan

| | WEEK # | | | | | | | | |
|---|---|---|---|---|---|---|---|---|---|
| | 1 | 2 | 3 | 5 | 7 | 9 | 13 | 19 | 21 | (q 3 months) |
| VACCINE | 1 | 2 | 3 | | 4 | | | 5 | | |
| Blood Samples for Immune Response | ✓ | ✓ | ✓ | ✓ | ✓ | ✓ | ✓ | ✓ | ✓ | ✓ |

Eligibility Criteria
  Breast cancer patients with any one of the following features:
    Stage IV (stable on hormone therapy [tx])
    Stage IV (no evidence of disease [NED])
    Stage III
    Stage II (≧4 positive nodes)
    Ipsilateral breast or axillary recurrence
    Rising CA15-3 or CEA levels and NED
Patient Characteristics
  Total number of patients treated: 10
  Total number of vaccinations completed: 50
    (One patient was delayed for unrelated issues)
  Median age: 48 years (range 43-63 years)
  Stage

| | | |
|---|---|---|
| II (with ≧4+ nodes): | 7 | |
| IV (NED): | 2 | |
| IV (stable on hormone tx): | 1 | |
| | n = 10 | |

Common Toxicities
  Grade 1-2 injection site skin reactions
  Grade 1-2-flu-like symptoms
  No significant laboratory abnormalities
  No definite autoimmune reactions
Response Criteria: ELISA
  Serologic Response by ELISA (Enzyme-Linked Immunosorbent Assay)
    IgM and IgG antibody titers were considered positive for each antigen if there was a ≧eightfold increase above baseline more than once, during weeks 1-19
  Immunologic Response
  Patient was considered a responder if there was a serologic response to at least 3 of the 7 antigens
Response Criteria: FACS and CDC
  Response by FACS (flourescence activated cell sorter) was considered positive if there was the following increase above baseline:
    ≧3-fold increase in percent gated positivity, AND
    ≧1.5-fold increase on MFI (mean flourescence intensity)
  Response by CDC (complement-dependent cytotoxicity) was considered positive if there was a 20% increase above baseline

| | IMMUNE RESPONSE DATA ELISA | | | | | | | | | | | | | |
|---|---|---|---|---|---|---|---|---|---|---|---|---|---|---|
| | GM2 | | MUC-1 | | Lewisy | | GLOBOH | | TF | | Tn | | sTn | |
| | IgM | IgG | IgM | IgG | IgM | IgG | IgM | IgG | IgM | IgG | IgM | IgG | IgM | IgG |
| 1 | − | − | + | + | − | − | − | − | + | + | − | − | − | − |
| 2 | + | − | + | + | − | − | + | − | + | + | + | − | + | − |
| 3 | + | − | + | + | − | − | + | − | + | + | + | − | + | − |
| 4 | − | − | + | + | + | − | + | + | + | + | + | − | − | − |
| 5 | − | − | − | + | − | − | − | − | − | − | − | − | − | − |
| 6 | − | − | + | + | − | − | + | − | + | + | + | − | + | − |
| 7 | + | − | + | + | − | − | − | − | + | + | + | − | − | − |
| 8 | − | − | + | + | − | − | + | − | + | + | − | − | + | − |
| 9 | − | − | + | + | − | − | + | − | + | + | − | − | − | + |
| 10 | − | − | + | + | − | − | + | − | + | + | − | − | + | − |
| •SUM | 3 | 0 | 9 | 10 | 1 | 0 | 7 | 1 | 9 | 9 | 5 | 0 | 5 | 1 |

| IMMUNE RESPONSE DATA FACS and CDC | | | | | |
|---|---|---|---|---|---|
| | FACS (IgM) | | | CDC | |
| Patient | MCF-7 | LSC | Du-175 | MCF-7 | LSC |
| 1 | + | + | + | − | − |
| 2 | − | + | − | + | + |
| 3 | + | − | − | − | − |
| 4 | + | + | + | + | + |
| 5 | − | − | − | − | − |
| 6 | + | + | − | + | − |
| 7 | + | + | − | − | + |
| 8 | − | + | − | + | − |
| 9 | + | + | + | − | − |
| 10 | − | − | − | + | − |
| •SUM | 6 | 7 | 3 | 5 | 3 |

CONCLUSION

Vaccination with a heptavalent antigen-KLH conjugate plus QS-21 is well tolerated in breast cancer patients IgM and IgG antibody responses (to at least 3 of 7 antigens) were observed in 8 patients and 2 patients respectively MUC1 and TF(c) to be appear the most immunogenic of the seven antigens in this vaccine IgM antibody binding to tumor cells (MCF-7, LSC, Du-145) by FACS analysis was observed in 6 patients, 7 patients, and 3 patients respectively There was no consistent evidence of IgG antibody binding to tumor cells by FACS There was evidence of CDC with the MCF-7 and LSC tumor cell lines in 5 patients and 3 patients respectively Our next cohort will evaluate the same antigens conjugated to KLH but with GP-100 as the immunologic adjuvant

What is claimed is:

1. A method for inducing antibody production in a subject comprising administering an immunogenic composition comprising an adjuvant and antigens comprising GloboH, GM2, MUC-1, Tn and TF(c), wherein the antigens are individually conjugated to a carrier.

2. The method of claim 1, wherein MUC-1 is a 32-mer.

3. The method of claim 2, wherein MUC-1-32-mer is glycosylated.

4. The method of claim 1, wherein MUC-1 is provided as MUC-1-G5.

5. The method of claim 1, wherein Tn is provided as Tn(c).

6. The method of claim 1, wherein Tn is provided as sTn(c).

7. The method of claim 1, further comprising an antigen selected from the group consisting of MUC-2, MUC-16, $Le^Y$, sialyl $Le^a$, GM1, GD2, and GD3.

8. An immunogenic composition comprising an adjuvant and antigens comprising GloboH, GM2, MUC-1, Tn and TF(c), wherein the antigens are individually conjugated to a carrier.

9. The immunogenic composition of claim 8, wherein MUC-1 is a 32-mer.

10. The immunogenic composition of claim 9, wherein MUC-1-32-mer is glycosylated.

11. The immunogenic composition of claim 8, wherein MUC-1 is provided as MUC-1-G5.

12. The immunogenic composition of claim 8, wherein Tn is provided as Tn(c).

13. The immunogenic composition of claim 8, wherein Tn is provided as sTn(c).

14. The immunogenic composition of claim 8, further comprising an antigen selected from the group consisting of MUC-2, MUC-16, $Le^Y$, sialyl $Le^a$, GM1, GD2, and GD3.

15. The immunogenic composition of claim 10, wherein MUC-1-32-mer is glycosylated with Tn.

16. The immunogenic composition of claim 15, wherein said glycosylated MUC-1-32-mer is further conjugated to KLH.

17. An immunogenic composition comprising an adjuvant and antigens comprising MUC1-Tn conjugate, GloboH and TF(c), wherein said conjugate and each of said GloboH and TF(c) antigens are individually conjugated to a carrier.

18. The immunogenic composition of claim 17 further comprising GM2 antigen.

19. The immunogenic composition of claim 17 further comprising the STn antigen.

20. The immunogenic composition of claim 17, wherein the Muc1-Tn conjugate antigen is conjugated to KLH.

21. An immunogenic composition comprising an adjuvant and at least two antigens individually conjugated to a carrier, wherein one of the said two antigens is the MUC1-Tn conjugate.

\* \* \* \* \*

UNITED STATES PATENT AND TRADEMARK OFFICE
CERTIFICATE OF CORRECTION

PATENT NO. : 8,092,780 B2
APPLICATION NO. : 12/262729
DATED : January 10, 2012
INVENTOR(S) : Philip O. Livingston, Govindaswami Ragupathi and Samuel J. Danishefsky It is certified that error appears in the above-identified patent and that said Letters Patent is hereby corrected as shown below:

On Title page 1, Item (56) Ref. Cited in 2nd column, the 10th reference, "Livingston et al. (Journal of Clinical Oncology, 2000, vol. 20, pp. 85-93)." should be -- Livingston et al. (Journal of Clinical Immunology, 2000, vol. 20, pp. 85-93). --

In column 94, claim 19, "The immunogenic composition of claim 17 further comprising the STn antigen." should be -- The immunogenic composition of claim 17 further comprising STn antigen. --

Signed and Sealed this
Thirteenth Day of March, 2012

David J. Kappos
*Director of the United States Patent and Trademark Office*

UNITED STATES PATENT AND TRADEMARK OFFICE
CERTIFICATE OF CORRECTION

PATENT NO. : 8,092,780 B2  
APPLICATION NO. : 12/262729  
DATED : January 10, 2012  
INVENTOR(S) : Philip O. Livingston, Govindaswami Ragupathi and Samuel J. Danishefsky Page 1 of 1

It is certified that error appears in the above-identified patent and that said Letters Patent is hereby corrected as shown below:

On Title page 1, Item (56) Ref. Cited in 2nd column, the 10th reference, "Livingston et al. (Journal of Clinical Oncology, 2000, vol. 20, pp. 85-93)." should be -- Livingston et al. (Journal of Clinical Immunology, 2000, vol. 20, pp. 85-93). --

In column 94, lines 26-27, claim 19, "The immunogenic composition of claim 17 further comprising the STn antigen." should be -- The immunogenic composition of claim 17 further comprising STn antigen. --

This certificate supersedes the Certificate of Correction issued March 13, 2012.

Signed and Sealed this  
Third Day of April, 2012

David J. Kappos  
*Director of the United States Patent and Trademark Office*